United States Patent
Enlow et al.

(10) Patent No.: US 11,713,323 B2
(45) Date of Patent: *Aug. 1, 2023

(54) CRYSTALLINE FORMS OF THERAPEUTIC COMPOUNDS AND USES THEREOF

(71) Applicant: Kala Pharmaceuticals, Inc., Watertown, MA (US)

(72) Inventors: Elizabeth Enlow, Waltham, MA (US); Minh Ngoc Nguyen, Dorchester, MA (US); Winston Z. Ong, Stoneham, MA (US)

(73) Assignee: Kala Pharmaceuticals, Inc., Arlington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/197,702

(22) Filed: Mar. 10, 2021

(65) Prior Publication Data

US 2021/0355133 A1   Nov. 18, 2021

Related U.S. Application Data

(60) Continuation of application No. 16/806,819, filed on Mar. 2, 2020, now Pat. No. 10,975,090, which is a continuation of application No. 16/184,760, filed on Nov. 8, 2018, now Pat. No. 10,618,906, which is a continuation of application No. 15/712,645, filed on Sep. 22, 2017, now Pat. No. 10,160,765, which is a continuation of application No. 14/981,105, filed on Dec. 28, 2015, now Pat. No. 9,790,232, which is a division of application No. 14/530,092, filed on Oct. 31, 2014, now Pat. No. 9,458,169.

(60) Provisional application No. 62/039,177, filed on Aug. 19, 2014, provisional application No. 62/039,192, filed on Aug. 19, 2014, provisional application No. 61/898,741, filed on Nov. 1, 2013.

(51) Int. Cl.

| | |
|---|---|
| *C07D 491/107* | (2006.01) |
| *A61K 9/00* | (2006.01) |
| *A61K 9/10* | (2006.01) |
| *A61K 9/14* | (2006.01) |
| *A61K 47/10* | (2017.01) |
| *A61K 9/50* | (2006.01) |
| *A61K 31/517* | (2006.01) |

(52) U.S. Cl.
CPC ........ *C07D 491/107* (2013.01); *A61K 9/0048* (2013.01); *A61K 9/10* (2013.01); *A61K 9/14* (2013.01); *A61K 9/146* (2013.01); *A61K 9/5021* (2013.01); *A61K 31/517* (2013.01); *A61K 47/10* (2013.01); *A61K 9/0034* (2013.01); *C07B 2200/13* (2013.01)

(58) Field of Classification Search
CPC ................................................. C07D 491/107
See application file for complete search history.

(56) References Cited

U.S. PATENT DOCUMENTS

| | | | |
|---|---|---|---|
| 4,910,225 A | 3/1990 | Ogawa et al. | |
| 4,996,335 A | 2/1991 | Bodor | |
| 5,190,956 A | 3/1993 | Afonso et al. | |
| 5,364,884 A | 11/1994 | Varma et al. | |
| 5,442,039 A | 8/1995 | Hefner, Jr. et al. | |
| 5,486,512 A | 1/1996 | Gregor | |
| 5,518,187 A | 5/1996 | Bruno et al. | |
| 5,534,259 A | 7/1996 | Zalipsky et al. | |
| 5,580,870 A | 12/1996 | Barker et al. | |
| 5,718,388 A | 2/1998 | Czekai et al. | |
| 5,747,061 A | 5/1998 | Aselem et al. | |
| 5,773,476 A | 6/1998 | Chen et al. | |
| 5,862,999 A | 1/1999 | Czekai et al. | |
| 5,922,357 A | 7/1999 | Coombes et al. | |
| 6,046,208 A | 4/2000 | Adams et al. | |
| 6,106,819 A | 8/2000 | Sucher | |
| 6,153,607 A | 11/2000 | Pflugfelder et al. | |
| 6,153,617 A | 11/2000 | Bridges | |
| 6,165,509 A | 12/2000 | Hoffman et al. | |
| 6,197,346 B1 | 3/2001 | Mathiowitz et al. | |
| 6,217,908 B1 | 4/2001 | Mathiowitz et al. | |
| 6,235,313 B1 | 5/2001 | Mathiowitz et al. | |
| 6,264,981 B1 | 7/2001 | Zhang et al. | |
| 6,288,082 B1 | 9/2001 | Wissner et al. | |
| 6,365,187 B2 | 4/2002 | Mathiowitz et al. | |
| 6,372,246 B1 | 4/2002 | Wei et al. | |
| 6,627,228 B1 | 9/2003 | Milstein et al. | |
| 6,706,289 B2 | 3/2004 | Lewis et al. | |
| 7,153,524 B2 | 12/2006 | Yoshihara et al. | |
| 7,262,201 B1 | 8/2007 | Hennequin et al. | |
| 7,534,449 B2 | 5/2009 | Saltzman et al. | |
| 7,550,441 B2 | 6/2009 | Farokhzad et al. | |
| 7,795,237 B2 | 9/2010 | Ahmed et al. | |
| 7,842,232 B2 | 11/2010 | Bosch et al. | |
| 7,906,136 B2 | 3/2011 | Wong et al. | |
| 9,458,169 B2 | 10/2016 | Enlow et al. | |
| 10,160,765 B2 * | 12/2018 | Enlow ................... | A61K 9/0048 |
| 10,618,906 B2 * | 4/2020 | Enlow ..................... | A61P 43/00 |

(Continued)

FOREIGN PATENT DOCUMENTS

| | | |
|---|---|---|
| AU | 2006220411 A1 | 10/2006 |
| CA | 2 564 982 A1 | 11/2005 |

(Continued)

OTHER PUBLICATIONS

Albertsson et al., "Synthesis, Characterization and Degradation of Aliphatic Polyanhydrides", British Polymer Journal, (1990), vol. 23, No. 3, pp. 205-212.

(Continued)

*Primary Examiner* — Paul V Ward
(74) *Attorney, Agent, or Firm* — K&L Gates LLP; Louis C. Cullman; Michelle Glasky Bergman

(57) ABSTRACT

Described herein are certain crystalline forms of Compound 3, as well as pharmaceutical compositions employing the crystalline forms. Also provided are particles (e.g., nanoparticles) comprising such crystalline forms or pharmaceutical compositions. In certain examples, the particles are mucus penetrating particles (MPPs). The present invention further relates to methods of treating or preventing diseases using crystalline forms or pharmaceutical compositions.

10 Claims, 9 Drawing Sheets

(56) References Cited

U.S. PATENT DOCUMENTS

| | | |
|---|---|---|
| 2001/0000521 A1 | 4/2001 | Bigg et al. |
| 2002/0013322 A1 | 1/2002 | Smith et al. |
| 2002/0026052 A1 | 2/2002 | Boschelli et al. |
| 2002/0107392 A1 | 8/2002 | Ren et al. |
| 2002/0147205 A1 | 10/2002 | Carter et al. |
| 2003/0032624 A1 | 2/2003 | Yang |
| 2003/0055049 A1 | 3/2003 | Kath et al. |
| 2003/0092721 A1 | 5/2003 | Pitts et al. |
| 2003/0092908 A1 | 5/2003 | Pitts et al. |
| 2003/0100573 A1 | 5/2003 | Wang et al. |
| 2003/0114452 A1 | 6/2003 | Adams et al. |
| 2003/0114486 A1 | 6/2003 | Metcalf et al. |
| 2003/0181472 A1 | 9/2003 | Clark et al. |
| 2003/0199491 A1 | 10/2003 | Hennequin |
| 2003/0212276 A1 | 11/2003 | Boschelli et al. |
| 2004/0063955 A1 | 4/2004 | Biediger et al. |
| 2004/0092535 A1 | 5/2004 | Barsanti et al. |
| 2004/0235848 A1 | 11/2004 | Okuzumi et al. |
| 2005/0009809 A1 | 1/2005 | Gerlach et al. |
| 2005/0009815 A1 | 1/2005 | Devita et al. |
| 2005/0026915 A1 | 2/2005 | Devita et al. |
| 2005/0038050 A1 | 2/2005 | Moore et al. |
| 2005/0054662 A1 | 3/2005 | Hennequin et al. |
| 2005/0058603 A1 | 3/2005 | Gao et al. |
| 2005/0085465 A1 | 4/2005 | Hennequin et al. |
| 2005/0101617 A1 | 5/2005 | Wallace et al. |
| 2005/0124562 A1 | 6/2005 | Guiles et al. |
| 2005/0137399 A1 | 6/2005 | Cai et al. |
| 2005/0148607 A1 | 7/2005 | Suzuki et al. |
| 2005/0187247 A1 | 8/2005 | Berger et al. |
| 2005/0191359 A1 | 9/2005 | Goldshtein et al. |
| 2005/0239825 A1 | 10/2005 | Heise et al. |
| 2005/0245547 A1 | 11/2005 | Kim et al. |
| 2005/0256157 A1 | 11/2005 | Gesner et al. |
| 2005/0261307 A1 | 11/2005 | Cai et al. |
| 2005/0266067 A1 | 12/2005 | Sengupta et al. |
| 2005/0266090 A1 | 12/2005 | Prokop et al. |
| 2005/0282802 A1 | 12/2005 | Kostik et al. |
| 2006/0004017 A1 | 1/2006 | Stokes et al. |
| 2006/0025406 A1 | 2/2006 | Zembower et al. |
| 2006/0058325 A1 | 3/2006 | Mortlock |
| 2006/0058523 A1 | 3/2006 | Mortlock et al. |
| 2006/0079515 A1 | 4/2006 | Frost |
| 2006/0116357 A1 | 6/2006 | Heron et al. |
| 2006/0167026 A1 | 7/2006 | Nawa et al. |
| 2006/0223783 A1 | 10/2006 | Xu et al. |
| 2006/0241115 A1 | 10/2006 | Potashman et al. |
| 2006/0252777 A1 | 11/2006 | Kim et al. |
| 2006/0257487 A1 | 11/2006 | Owen et al. |
| 2006/0264460 A1 | 11/2006 | Green et al. |
| 2006/0270668 A1 | 11/2006 | Chew et al. |
| 2006/0270669 A1 | 11/2006 | Chew et al. |
| 2007/0032518 A1 | 2/2007 | Norman et al. |
| 2007/0054916 A1 | 3/2007 | Patel et al. |
| 2007/0059552 A1 | 3/2007 | Takeda et al. |
| 2007/0060608 A1 | 3/2007 | Vanderslice et al. |
| 2007/0060613 A1 | 3/2007 | Kim |
| 2007/0093432 A1 | 4/2007 | Yang |
| 2007/0129387 A1 | 6/2007 | McCabe |
| 2007/0149480 A1 | 6/2007 | Ghosh et al. |
| 2007/0149523 A1 | 6/2007 | Ehlert et al. |
| 2007/0178051 A1 | 8/2007 | Pruitt et al. |
| 2007/0196860 A1 | 8/2007 | Gee et al. |
| 2007/0213319 A1 | 9/2007 | Zembower et al. |
| 2007/0231821 A1 | 10/2007 | Bupp et al. |
| 2007/0299044 A1 | 12/2007 | Farng et al. |
| 2008/0027099 A1 | 1/2008 | Govek et al. |
| 2008/0096193 A1 | 4/2008 | Bupp et al. |
| 2008/0125448 A1 | 5/2008 | Qian et al. |
| 2008/0153799 A1 | 6/2008 | Laurent et al. |
| 2008/0159984 A1 | 7/2008 | Ben-Sasson |
| 2008/0175887 A1 | 7/2008 | Wang |
| 2008/0194468 A1 | 8/2008 | Bodor |
| 2008/0200464 A1 | 8/2008 | Bellon et al. |
| 2008/0221161 A1 | 9/2008 | Pinkerton et al. |
| 2008/0248125 A1 | 10/2008 | Irache Garreta et al. |
| 2008/0267876 A1 | 10/2008 | Benita et al. |
| 2008/0280917 A1 | 11/2008 | Albrecht et al. |
| 2008/0306053 A1 | 12/2008 | Tachdjian et al. |
| 2008/0312232 A1 | 12/2008 | Kim et al. |
| 2008/0318943 A1 | 12/2008 | Chang et al. |
| 2009/0036474 A1 | 2/2009 | Pie et al. |
| 2009/0047244 A1 | 2/2009 | Parsy et al. |
| 2009/0062279 A1 | 3/2009 | Marsais et al. |
| 2009/0062337 A1 | 3/2009 | Schwan et al. |
| 2009/0076044 A1 | 3/2009 | Qian et al. |
| 2009/0087493 A1 | 4/2009 | Dai et al. |
| 2009/0105211 A1 | 4/2009 | Bahceci et al. |
| 2009/0131461 A1 | 5/2009 | Davidson et al. |
| 2009/0221591 A1 | 9/2009 | Hartmann et al. |
| 2009/0253148 A1 | 10/2009 | Piper et al. |
| 2010/0015136 A1 | 1/2010 | Michel et al. |
| 2010/0048447 A1 | 2/2010 | Haetzelt et al. |
| 2010/0056506 A1 | 3/2010 | Huang et al. |
| 2010/0076045 A1 | 3/2010 | Castillo et al. |
| 2010/0093727 A1 | 4/2010 | Ning et al. |
| 2010/0168149 A1 | 7/2010 | Lavielle et al. |
| 2010/0204234 A1 | 8/2010 | Hartmann et al. |
| 2010/0222308 A1 | 9/2010 | Zhang et al. |
| 2010/0226931 A1 | 9/2010 | Valiante et al. |
| 2010/0290983 A1 | 11/2010 | Rabinow et al. |
| 2011/0053931 A1 | 3/2011 | Gaudino et al. |
| 2011/0104161 A1 | 5/2011 | Burgess et al. |
| 2011/0166168 A1 | 7/2011 | Buchmann et al. |
| 2011/0172186 A1 | 7/2011 | Behnke et al. |
| 2011/0275643 A1 | 11/2011 | Liou et al. |
| 2011/0306572 A1 | 12/2011 | Estok et al. |
| 2011/0319403 A1 | 12/2011 | Zhou et al. |
| 2012/0021897 A1 | 1/2012 | Iwata et al. |
| 2012/0121718 A1 | 5/2012 | Lai et al. |
| 2012/0214803 A1 | 8/2012 | Buhr et al. |
| 2012/0225875 A1 | 9/2012 | Jonczyk et al. |
| 2012/0232110 A1 | 9/2012 | Moy et al. |
| 2012/0252756 A1 | 10/2012 | Coffey et al. |
| 2012/0264715 A1 | 10/2012 | Takeuchi et al. |
| 2012/0264730 A1 | 10/2012 | Takeuchi et al. |
| 2012/0264732 A1 | 10/2012 | Takeuchi et al. |
| 2012/0289486 A1 | 11/2012 | Bodor |
| 2012/0292571 A1 | 11/2012 | Buesing et al. |
| 2012/0305852 A1 | 12/2012 | Anemian et al. |
| 2013/0102603 A1 | 4/2013 | Dorsch et al. |
| 2013/0109713 A1 | 5/2013 | Lavoie et al. |
| 2013/0116279 A1 | 5/2013 | Govek et al. |
| 2013/0123344 A1 | 5/2013 | Kristie et al. |
| 2013/0210844 A1 | 8/2013 | Gharat et al. |
| 2013/0245032 A1 | 9/2013 | Chen et al. |
| 2013/0281402 A1 | 10/2013 | Chen et al. |
| 2013/0324570 A1 | 12/2013 | Hansen et al. |
| 2013/0344165 A1 | 12/2013 | Boden et al. |
| 2014/0024661 A1 | 1/2014 | Zhou et al. |
| 2014/0142137 A1 | 5/2014 | Cohen et al. |
| 2014/0163037 A1 | 6/2014 | Guenther et al. |
| 2014/0228361 A1 | 8/2014 | Zhang et al. |
| 2014/0235548 A1 | 8/2014 | Zhou et al. |
| 2014/0235657 A1 | 8/2014 | Ong et al. |
| 2014/0239281 A1 | 8/2014 | Ise et al. |
| 2014/0294764 A1 | 10/2014 | Yoon et al. |
| 2014/0294973 A1 | 10/2014 | Kan et al. |
| 2014/0296136 A1 | 10/2014 | Rudd et al. |
| 2014/0315886 A1 | 10/2014 | Suzuki et al. |
| 2015/0125535 A1 | 5/2015 | Enlow et al. |

FOREIGN PATENT DOCUMENTS

| | | |
|---|---|---|
| CN | 1724521 A | 1/2006 |
| CN | 1955183 A | 5/2007 |
| CN | 101012224 A | 8/2007 |
| CN | 101012225 A | 8/2007 |
| CN | 101108846 A | 1/2008 |
| CN | 101747306 B | 8/2012 |
| CN | 103304572 A | 9/2013 |
| CN | 103804292 A | 5/2014 |
| CN | 103102342 B | 10/2014 |

(56) References Cited

FOREIGN PATENT DOCUMENTS

| | | |
|---|---|---|
| CN | 103102345 B | 6/2015 |
| DE | 102005009705 A1 | 9/2006 |
| DE | 102008012435 A1 | 9/2009 |
| EP | 0837063 A1 | 4/1998 |
| EP | 0 692 510 B1 | 12/2004 |
| EP | 1785420 A1 | 5/2007 |
| EP | 1 744 759 B1 | 9/2009 |
| EP | 2 127 655 A1 | 12/2009 |
| EP | 2335686 | 6/2011 |
| GB | 2345486 A | 7/2000 |
| JP | 2008214323 A | 9/2008 |
| JP | 2011178753 A | 9/2011 |
| KR | 20140072295 A | 6/2014 |
| KR | 20140103391 A | 8/2014 |
| KR | 20140105634 A | 9/2014 |
| WO | 95/03356 A1 | 2/1995 |
| WO | 95/22318 A1 | 8/1995 |
| WO | 1997/003069 A1 | 1/1997 |
| WO | 97/20578 A1 | 6/1997 |
| WO | 97144013 A1 | 11/1997 |
| WO | 98/29097 A1 | 7/1998 |
| WO | 98/31346 A1 | 7/1998 |
| WO | 1998/030545 A1 | 7/1998 |
| WO | 99/01498 A1 | 1/1999 |
| WO | 2000/018761 A1 | 4/2000 |
| WO | 2000/042026 A1 | 7/2000 |
| WO | 00/46147 A2 | 8/2000 |
| WO | 0051991 A1 | 9/2000 |
| WO | 0055141 A1 | 9/2000 |
| WO | 0068199 A1 | 11/2000 |
| WO | 0068200 A1 | 11/2000 |
| WO | 2001/072711 A1 | 10/2001 |
| WO | 0194341 A1 | 12/2001 |
| WO | 0218372 A1 | 3/2002 |
| WO | 0222618 A1 | 3/2002 |
| WO | 02/38127 A2 | 5/2002 |
| WO | 02/053189 A2 | 7/2002 |
| WO | 2002/060868 A2 | 8/2002 |
| WO | 02076976 A2 | 10/2002 |
| WO | 02092571 A1 | 11/2002 |
| WO | 02100874 A1 | 12/2002 |
| WO | 03/000237 A2 | 1/2003 |
| WO | 03051906 A3 | 11/2003 |
| WO | 2004/046101 A2 | 6/2004 |
| WO | 2005007643 A1 | 1/2005 |
| WO | 2005035521 A1 | 4/2005 |
| WO | 2005/072710 A2 | 8/2005 |
| WO | 2005/094836 A2 | 10/2005 |
| WO | 2005105146 A1 | 11/2005 |
| WO | 2005097134 A3 | 1/2006 |
| WO | 2005097137 A3 | 2/2006 |
| WO | 2006030941 A1 | 3/2006 |
| WO | 2006/035203 A1 | 4/2006 |
| WO | 2006/044660 A2 | 4/2006 |
| WO | 2006/063249 A2 | 6/2006 |
| WO | 2006/089150 A2 | 8/2006 |
| WO | 2006094808 | 9/2006 |
| WO | 2006117570 A1 | 11/2006 |
| WO | 2007015569 A1 | 2/2007 |
| WO | 2007015578 A1 | 2/2007 |
| WO | 2007104696 A1 | 9/2007 |
| WO | 2007107318 A1 | 9/2007 |
| WO | 2007/119046 A1 | 10/2007 |
| WO | 2007/133211 A1 | 11/2007 |
| WO | 2007/133808 A2 | 11/2007 |
| WO | 2008001956 A1 | 1/2008 |
| WO | 2008/030557 A2 | 3/2008 |
| WO | 2008/033924 A2 | 3/2008 |
| WO | 2008020302 A3 | 4/2008 |
| WO | 2008/056148 A1 | 5/2008 |
| WO | 2008113161 A1 | 9/2008 |
| WO | 2008/124632 A1 | 10/2008 |
| WO | 2008053221 A3 | 12/2008 |
| WO | 2009030224 A2 | 3/2009 |
| WO | 2008041960 A3 | 5/2009 |
| WO | 2009/089851 A1 | 7/2009 |
| WO | 2009094211 A1 | 7/2009 |
| WO | 2010021918 A1 | 2/2010 |
| WO | 2010056758 A1 | 5/2010 |
| WO | 2010/102811 A1 | 9/2010 |
| WO | 2011/106168 A1 | 9/2011 |
| WO | 2011106702 | 9/2011 |
| WO | 2011/157428 A2 | 12/2011 |
| WO | 2011/159328 A1 | 12/2011 |
| WO | 2012/013884 A1 | 2/2012 |
| WO | 2012/014114 A1 | 2/2012 |
| WO | 2012/025237 A1 | 3/2012 |
| WO | 2012/038942 A1 | 3/2012 |
| WO | 2012/038943 A1 | 3/2012 |
| WO | 2012/038944 A1 | 3/2012 |
| WO | 2012/039979 A2 | 3/2012 |
| WO | 2012054923 | 4/2012 |
| WO | 2012/059158 A1 | 5/2012 |
| WO | 2012/061703 A1 | 5/2012 |
| WO | 2012/071042 A1 | 5/2012 |
| WO | 2012040499 A3 | 5/2012 |
| WO | 2012/074980 A2 | 6/2012 |
| WO | 2012/088431 A1 | 6/2012 |
| WO | 2012/088469 A1 | 6/2012 |
| WO | 2012/093117 A1 | 7/2012 |
| WO | 2012/109363 A2 | 8/2012 |
| WO | 2012/127506 A1 | 9/2012 |
| WO | 2012/149228 A1 | 11/2012 |
| WO | 2012/155062 A1 | 11/2012 |
| WO | 2012/162698 A1 | 11/2012 |
| WO | 2013013614 A1 | 1/2013 |
| WO | 2013/040347 A1 | 3/2013 |
| WO | 2013/061269 A1 | 5/2013 |
| WO | 2013/065028 A1 | 5/2013 |
| WO | 2013/090804 A2 | 6/2013 |
| WO | 2013097753 A1 | 7/2013 |
| WO | 2013120057 A1 | 8/2013 |
| WO | 2013158928 A3 | 12/2013 |
| WO | 2013179144 A3 | 3/2014 |
| WO | 2013188813 A3 | 3/2014 |
| WO | 2014074517 A1 | 5/2014 |
| WO | 2014074848 A1 | 5/2014 |
| WO | 2014074926 A1 | 5/2014 |
| WO | 2014086284 A1 | 6/2014 |
| WO | 2014/130612 A1 | 8/2014 |
| WO | 2014094962 A3 | 9/2014 |
| WO | 2014134705 A1 | 9/2014 |
| WO | 2014147611 A1 | 9/2014 |
| WO | 2014159837 A1 | 10/2014 |
| WO | 2014111269 A3 | 11/2014 |
| WO | 2014182954 A1 | 11/2014 |
| WO | 2014186398 A1 | 11/2014 |
| WO | 2014141057 A3 | 2/2015 |
| WO | 2014141110 A3 | 4/2015 |
| WO | 2015/0066482 A1 | 5/2015 |

OTHER PUBLICATIONS

Apgar et al., "Multiple-Particle Tracking Measurements of the Heterogeneities in Solutions of Actin Filaments and Actin Bundles", Biophysical Journal, (Aug. 2000), vol. 79, No. 2, pp. 1095-1106.
Batrakove et al., "Pluronic Block Copolymers: Evolution of Drug Delivery Concept from Inert Nanocarriers to Biological Response Modifiers", J. Control Release, (Sep. 10, 2008), vol. 130, No. 2, 25 pages.
Bhalla, "Microtubule-targeted anticancer agents and apoptosis", Oncogene, (2003), vol. 22, pp. 9075-9086.
Boskey et al., "A Self-Sampling Method to Obtain Large Volumes of Undiluted Cervicovaginal Secretions", Sexually Transmitted Diseases, (Feb. 2003), vol. 30, No. 2, pp. 107-109.
Boylan et al., "Enhancement of airway gene transfer by DNA nanoparticles using a pH-responsive block copolymer glycol and poly-L-lysine", Biomaterials, (2012) vol. 33, pp. 2361-2371.
Boylan et al., "Highly compacted DNA nanoparticles with low MW PEG coatings: In vitro, ex vivo and in vivo evaluation", Journal of Controlled Release, (2012), vol. 157, pp. 72-79.

(56) References Cited

OTHER PUBLICATIONS

Brorson et al., "Mutational Analysis of Avidity and Fine Specificity of Anti-Levan Antibodies", The Journal of Immunology, (1999), pp. 6694-6701.
Brummell et al., "Probing the Combining Site of an Anti-Carbohydrate Antibody by Saturation-Mutagenesis: Role of the Heavy-Chain CDR3 Residues", Biochemistry, (1993), vol. 32, No. 4, pp. 1180-1187.
Bures et al., "Surface modifications and molecular imprinting of polymers in medical and pharmaceutical applications", Journal of Controlled Release, (2001), vol. 72, pp. 25-33.
Burks et al., "In vitro scanning saturation mutagenesis of an antibody binding pocket", Proc. Natl. Acad. Sci. USA, (Jan. 1997), vol. 94, pp. 412-417.
Chan et al., "Phase behavior and miscibility in blends of poly(sebacic anhydride)/poly(ethylene glycol)", Biomaterials, (2002), vol. 23, pp. 2353-2358.
Bin Choy et al., "Mucoadhesive Microparticles Engineered for Ophthalmic Drug Delivery", J. Phys. Chem Solids, (May 2008), vol. 69, No. 5-6, 8 pages.
Colman, "Effects of amino acid sequence changes on antibody-antigen interactions", Research in Immunology, (1994), vol. 145, pp. 33-36.
Cone, "Barrier properties of mucus", Advanced Drug Delivery Reviews, (2009), vol. 61, pp. 75-85.
Cone, "Mucus", Mucosal Immunology, (1999), Section Edition, Chapter 4, pp. 43-64.
Cu et al., "Controlled surface modification with poly(ethylene)glycol enhances diffusion of PLGA nanoparticles in human cervical mucus". Mol Pharm., (2009), vol. 6, No. 1, 18 pages.
Dawson et al., "Transport of Polymeric Nanoparticle Gene Carriers in Gastric Mucus", Biotechnol. Prog., (2004), vol. 20, No. 3, pp. 851-857.
Dawson et al., "Enhanced Viscoelasticity of Human Cystic Fibrotic Sputum Correlates with Increasing Microheterogeneity in Particle Transport", The Journal of Biological Chemistry, (2003), vol. 278, No. 50, pp. 50393-50401.
Dawson et al., "Primary parenteral transmission of bovine spongiform encephalopathy to the pig", The Veterinary Record, (Sep. 29, 1990), 1 page.
De Campos et al., "The effect of a PEG versus a chitosan coating on the interaction of drug colloidal carriers with the ocular mucosa", European Journal of Pharmaceutical Sciences, (2003), vol. 20, pp. 73-81.
Delgado et al., "Radiolabelled biodegradable microspheres for lung imaging", European Journal of Pharmaceutics and Biopharmaceutics, (2000), vol. 50, pp. 227-236.
Denis-Mize et al., "Plasmid DNA adsorbed onto cationic microparticles mediates target gene expression and antigen presentation by dendritic cells", Gene Therapy, (2000), vol. 7, pp. 2105-2112.
Donaldson et al., "A placebo-controlled multi-centred evaluation of an anaesthetic gel (Oraqix®) for periodontal therapy", Journal of Clinical Peridontology, (2003), vol. 30, pp. 171-175.
Dufner et al., "Harnessing phage and ribosome display for antibody optimisation", Trends in Biotechnology, (2006), vol. 24, No. 11, pp. 523-529.
Dumortier et al., "A Review of Poloxamer 407 Pharmaceutical and Pharmacological Characteristics", Pharmaceutical Research, (Dec. 2006), vol. 23, No. 12, pp. 2709-2728.
Ehrhardt et al., "Drug Absorption by the Respiratory Mucosa: Cell Culture Models and Particulate Drug Carriers", Journal of Aerosol Medicine, (2002), vol. 15, No. 2, pp. 131-139.
Emanuele, "Flocor™: a new anti-adhesive, rheologic agent", Expert Opinion on Investigational Drugs, (1998), vol. 7, No. 7, pp. 1193-1200.
Ensign et al., "Oral drug delivery with polymeric nanoparticles: The gastrointestinal mucus barriers", Advanced Drug Delivery Reviews, (2012), vol. 64, pp. 557-570.
Ensign et al., "Mucus Penetrating Nanoparticles: Biophysical Tool and Method of Drug and Gene Delivery", Advanced Materials, (2012), vol. 24, pp. 3887-3894.
Ensign et al., "Enhanced vaginal drug delivery through the use of hypotonic formulations that induce fluid uptake", Biomaterials, (2013), vol. 34, pp. 6922-6929.
Ensign et al., "Ex Vivo Characterization of Particle Transport in Mucus Secretions Coating Freshly Excised Mucosal fissues", Molecular Pharmaceutics, (2013), vol. 10, pp. 2176-2182.
Ensign et al., "Mucus-Penetrating Nanoparticles for Vaginal Drug Deliver Protect Against Herpes Simplex Virus", Science Translational Medicine, (2012), vol. 4, Issue 138, pp. 1-10.
Escobar-Chávez et al., "Application of Thermo-Reversible Pluronic F-127 Gels in Pharmaceutical Formulations", J. Pharm. Pharmaceut. Sci., (2006), vol. 9, No. 3, pp. 339-358.
Farokhzad et al., "Targeted nanoparticle-aptamer bioconjugates for cancer chemotherapy in vivo", PNAS, (Apr. 18, 2006), vol. 103, No. 16, pp. 6315-6320.
Fresta et al., "Ocular Tolerability and In Vivo Bioavailability of Poly(ethylene glycol) (PEG)-Coated Polyethyl-2-Cyanoacrylate Nanosphere-Encapsulated Acyclovir", Journal of Pharmaceutical Science, (Mar. 2001), vol. 90, No. 3, pp. 288-297.
Fu et al., "New polymeric carriers for controlled drug delivery following inhalation or injection", Biomaterials, (2002), vol. 23, pp. 4425-4433.
Giannavola et al., "Influence of Preparation Conditions on Acyclovir-Loaded Poly-d,I-Lactic Acid Nanospheres and Effect of PEG Coating on Ocular Drug Bioavailability", Pharmaceutical Research, (Apr. 2003), vol. 20, No. 4, pp. 584-590.
Giunchedi et al., "Emulsion Spray-Drying for the Preparation of Albumin-Loaded PLGA Microspheres", Drug Development and Industrial Pharmacy, (2001), vol. 27, No. 7, pp. 745-750.
Hida et al., "Common Gene Therapy Viral Vectors Do Not Efficiently Penetrate Sputum from Cystic Fibrosis Patients", PLoS ONE, (May 2011), vol. 6, Issue 5, pp. 1-6.
Huang et al., "Molecular aspects of muco- and bioadhesion: Tethered structures and site-specific surfaces", Journal of Controlled Release, (2000), vol. 65, pp. 63-71.
Jachak et al., "Transport of metal oxide nanoparticles and single walled carbon nanotubes in human mucus", Nanotoxicology, (Sep. 2012), vol. 6, No. 6, pp. 614-622.
Jang et al., "The structural basis for DNA binding by an anti-DNA autoantibody", Molecular Immunology, (1998), vol. 35, pp. 1207-1217.
Jiang et al., "Pulsatile protein release from a laminated device comprising of polyanhydrides and pH-sensitive complexes", International Journal of Pharmaceutics, (2000), vol. 194, pp. 51-60.
Jiang et al., Preparation, characterization and degradation characteristics of polyanhydrides contained poly(ethylene glycol), Polymer International, (1999), vol. 48, pp. 47-52.
Kim et al., "Use of Single-Site-Functionalized PEG Dendrons To Prepare Gene Vectors that Penetrate Human Mucus Barriers", Angewandte Chemie International Edition, (2013), vol. 52, pp. 3985-3988.
Kim et al., "Comparison of the pharmacokinetic profiles of two locally administered doxycycline gels in crevicular fluid and saliva", Journal of Clinical Periodontology, (2004), vol. 31, pp. 286-292.
Knowles et al., "Mucus clearance as primary innate defense mechanism for mammalian airways", The Journal of Clinical Investigation, (Mar. 2002), vol. 109, No. 5, pp. 571-577.
Kobayashi et al., "Tryptophan H33 plays an important role in pyrimidine (6-4) pyrimidone photoproduct binding by a high-affinity antibody", Protein Engineering, (1999), vol. 12, No. 10, pp. 879-884.
Lai et al., "Micro- and macrorheology of mucus", Advanced Drug Delivery Reviews, (2009), vol. 61, pp. 86-100.
Lai et al., "Mucus-penetrating nanoparticles for drug and gene delivery to mucosal tissues", Adv. Drug Deliv. Rev., (Feb. 27, 2009), vol. 61, No. 2, 36 pages.
Lai et al., "Drug carrier nanoparticles that penetrate human chronic rhinosinusitis mucus", Biomaterials, (2011), vol. 32, pp. 6285-6290.
Lai et al., "Altering Mucus Rheology to "Solidify" Human Mucus at the Nanoscale", PLoS One, (Jan. 2009), vol. 4, Issue 1, pp. 1-6.

(56) References Cited

OTHER PUBLICATIONS

Lai et al., "Rapid transport of large polymeric nanoparticles in fresh undiluted human mucus", PNAS, (Jan. 30, 2007), vol. 104, No. 5, pp. 1482-1487.
Lai et al., "Nanoparticles reveal that human cervicovaginal mucus is riddled with pores larger than viruses", PNAS, (Jan. 12, 2010), vol. 107, No. 2, pp. 598-603.
Lipman et al., "Monoclonal Versus Polyclonal Antibodies: Distinguishing Characteristics, Applications, and Information Resources", ILAR Journal, (2005), vol. 46, No. 3, pp. 258-268.
Lo et al., "Formulation design and pharmaceutical development of a novel controlled release form of azithromycin for single-dose therapy", Drug Development and Industrial Pharmacy, (2009), vol. 35, No. 12, pp. 1522-1529.
Qiu et al., "Compatibility and degradation of new polyphosphazene/polyanhydride blend", CAPLUS, (2001), No. 5, Abstract Only.
Abelson et al., "Loteprednol Etabonate in the Management of Dry Eye Inflammation", Refractive eyecare for ophthalmologists, (Nov. 2000), vol. 4, No. 11, pp. 4-7.
Mert et al., "A poly(ethylene glycol)-based surfactant for formulation of drug-loaded mucus penetrating particles", Journal of Controlled Release, (2012), vol. 157, pp. 455-460.
Mu et al., "Vitamin E TPGS used as emulsifier in the solvent evaporation/extraction technique for fabrication of polymeric nanospheres for controlled release of paclitaxel (Taxol®)", Journal of Controlled Release, (2002), vol. 80, pp. 129-144.
Nance et al., "A Dense Poly(Ethylene Glycol) Coating Improves Penetration of Large Polymeric Nanoparticles Within Brain Tissue", Science Translational Medicine, (Aug. 29, 2012), vol. 4, Issue 149, pp. 1-8.
Newman et al., "Uptake of poly(D,L-lactic-co-glycolic acid) microspheres by antigen-presenting cells in vivo", Journal of Biomedical Materials Research, (Jun. 5, 2002), vol. 60, Issue 3, pp. 480-486.
Norris et al., "Effect of Size, Surface Charge, and Hydrophobicity on the Translocation of Polystyrene microspheres Through Gastrointestinal Mucin", Journal of Applied Polymer Science, (Mar. 14, 1997), vol. 63, Issue 11, pp. 1481-1492.
Norris et al., "The Uptake and Translocation of Microparticles through GI Mucin", Pharma. Res., (1995), vol. 12, pp. S233 abstract only.
Peppas et al., "Ultrapure poly(vinyl alcohol) hydrogels with mucoadhesive drug delivery characteristics", European Journal of Pharmaceutics and Biopharmaceutics, (1997), vol. 43, pp. 51-58.
Peppas et al., "Poly(ethylene glycol)-containing hydrogels in drug delivery", Journal of Controlled Release, (1999), vol. 62, pp. 81-87.
Peracchia et al., "PEG-coated nanospheres from amphiphilic diblock and multiblock copolymers: Investigation of their drug encapsulation and release characteristics", Journal of Controlled Release, (1997), vol. 46, pp. 223-231.
Perry, "Sorbent Materials and Sorption-Process Analysis", Perry's Chemical Engineers' Handbook, (1984), vol. 6, pp. 16-5-16-6.
Pillai et al., "Polymers in drug delivery", Current Opinion in Chemical Biology, (2001), vol. 5, pp. 447-451.
Prasad et al., "Confocal microscopy of colloids", Journal of Physics Condensed Matter, (2007), vol. 19, pp. 1-25.
Prego et al., "The potential of chitosan for the oral administration of peptides", Expert Opinion Drug Deliver, (2005), vol. 2, No. 5, pp. 843-854.
Pui, "Rasburicase: a potent uricolytic agent", Expert Opin. Pharmacother., (2002), vol. 3, No. 4, pp. 433-452.
Qiu et al., "Design of a core-shelled polymer cylinder for potential programmable drug delivery", International Journal of Pharmaceutics, (2001), vol. 219, pp. 151-160.
Rodeheaver et al., "Pluronic F-68: A Promising New Skin Wound Cleanser", Ann Emerg Med, (Nov. 1980), vol. 9, No. 11, pp. 572-576.
Rolland et al., "Direct Fabrication and Harvesting of Monodisperse, Shape-Specific Nanobiomaterials", J. Am. Chem. Soc., (2005), vol. 127, No. 28, pp. 10096-10100.
Schuster et al., "Nanoparticle diffusion in respiratory mucus from humans without lung disease", Biomaterials, (2013), vol. 34, pp. 3439-3446.
Serra et al., "Engineering Design and Molecular Dynamics of Mucoadhesive Drug Delivery Systems as Targeting Agents", Eur. J Pharm. Biopharm., (Mar. 2009), vol. 71, No. 3, 24 pages.
Serra et al., "Design of poly(ethylene glycol)-tethered copolymers as novel mucoadhesive drug delivery systems", European Journal of Pharmaceutics and Biopharmaceutics, (2006), vol. 63, pp. 11-18.
Shakesheff et al., "The Adsorption of Poly(vinyl alcohol) to Biodegradable Microparticles Studied by X-Ray Photoelectron Spectroscopy (XPS)", Journal of Colloid and Interface Science, (1997), vol. 185, pp. 538-547.
Singh et al., "Cationic microparticles: A potent delivery system for DNA vaccines", PNAS, (Jan. 18, 2000), vol. 97, No. 2, pp. 811-816.
Singla et al., "Paclitaxel and its formulations", International Journal of Pharmaceutics, (2002), vol. 235, pp. 179-192.
Suh et al., "Real-time multiple-particle tracking: applications to drug and gene delivery", Advanced Drug Delivery Reviews, (2005), vol. 57, pp. 63-78.
Suh et al., "PEGylation of nanoparticles improves their cytoplasmic transport", International Journal of Nanomedicine, (2007), vol. 2, No. 4, pp. 735-741.
Suk et al., "The penetration of fresh undiluted sputum expectorated by cystic fibrosis patients by non-adhesive polymer nanoparticles", Biomaterials, (2009), vol. 30, pp. 2591-2597.
Suk et al., "N-acetylcysteine Enhances Cystic Fibrosis Sputum Penetration and Airway Gene Transfer by Highly Compacted DNA Nanoparticles", Molecular Therapy, (Nov. 2011), vol. 19, No. 11, pp. 1981-1989.
Suk et al., "Rabid transport of muco-inert nanoparticles in cystic fibrosis sputum treated with N-acetyl cysteine", Nanomedicine, (2011), vol. 6, No. 2, pp. 365-375.
Tang et al., "Biodegradable polymer nanoparticles that rapidly penetrate the human mucus barrier", PNAS, (Nov. 17, 2009), vol. 106, No. 46, pp. 19268-19273.
Vila et al., "Transport of PLA-PEG particles across the nasal mucosa: effect of particle size and PEG coating density", Journal of Controlled Release, (2004), vol. 98, pp. 231 244.
Whaley et al., "Novel Approaches to Vaginal Delivery and Safety of Microbicides: Biopharmaceuticals, Nanoparticles, and Vaccines", Antiviral Research, (2010), vol. 885, pp. S55-S66.
Wang et al., "Mucoadhesive Nanoparticles May Disrupt the Protective Human Mucus Barrier by Altering Its Microstructure", PLoS One, (Jun. 2011), vol. 6, Issue 6, pp. 1-7.
Wang et al., "Addressing the PEG Mucoadhesivity Paradox to Engineer Nanoparticles that "Slip" through the Human Mucus Barrier", Angew. Chem. Int. Ed., (2008), vol. 47, pp. 1-5.
Wu et al., "Novel Nanoparticles Formed via Self-Assembly of Poly(ethylene glycol-b-sebacic anhydride) and Their Degradation in Water", Macromolecules, (2000), vol. 33, pp. 9040-9043.
Xu et al., "Nanoparticle diffusion in, and microrheology of, the bovine vitreous ex vivo", Journal of Controlled Release, (2013), vol. 167, pp. 76-84.
Xu et al., "Scalable method to produce biodegradable nanoparticles that rapidly penetrate human mucus", Journal of Controlled Release, (2013), vol. 170, pp. 279-286.
Yang et al., "Biodegradable Nanoparticles Composed Entirely of Safe Materials that Rapible Penetrate Human Mucus", Angew. Chem. Int. Ed., (2011), vol. 50, pp. 2597-2600.
Yoncheva et al., "Bioadhesive properties of pegylated nanoparticles", Expert Opin. Drug Deliv., (2005), vol. 2, No. 2, pp. 205-218.
Yoncheva et al., "Evaluation of bioadhesive potential and intestinal transport of pegylated poly(anhydride) nanoparticles", International Journal of Pharmaceutics, (2007), vol. 334, pp. 156-165.
Yoo et al., "Biodegradable Nanoparticles Containing Doxorubicin-PLGA Conjugate for Sustained Release", Pharmaceutical Research, (1999), vol. 16, No. 7, pp. 1114-1118.
Yu et al., "Biodegradable mucus-penetrating nanoparticles composed of diblock copolymers of polyethylene glycol anti poly(lactic-co-glycolic acid)", Drug Deliv. and Transl Res., (2012), vol. 2, pp. 124-128.

(56) References Cited

OTHER PUBLICATIONS

Declaration of Dr. Alexey Popov executed Feb. 21, 2013 with Curriculum vitae.
Shuai et al., "Synthesis and characterization of several degradable aliphatic polyanhydrides", Journal of Beijing Institute of Technology (English Edition), (1996), vol. 5, No. 2, pp. 130-136 abstract only.
Webster's Ninth New Collegiate Dictionary, (1988), pp. 58.
International Search Report (Form PCT/ISA/210) dated Mar. 12, 2008, by the International Bureau of WIPO in corresponding International Patent Application No. PCT/US2007/019522. (5 pages).
Hancock et al., "What is the True Solubility Advantage for Amorphous Pharmaceuticals?", Pharmaceutical Research, (Nov. 4, 2000), vol. 17, No. 4, pp. 397-404.
"Lutrol® L and Lutrol F-Grades", Pharma Ingredients & Services, (Apr. 2010), 8 pages.
Kapin et al., "Inflammation-Mediated Retinal Edema in the Rabbit Is Inhibited by Topical Nepafenac", Inflammation, (Oct. 2003), vol. 27, No. 5, pp. 281-291.
Lin et al., "Carbopol.pluronic phase change solutions for ophthalmic drug delivery", Journal of Controlled Release, (2000), vol. 69, pp. 379-388.
Alexandridis, "Poly(ethylene oxide)/poly(propylene oxide) block copolymer surfactants", Current Opinion in Colloid & Interface Science, (Oct. 1997), vol. 2, Issue 5, pp. 478-489.
Yamagata et al., Improvement of the Oral Drug Absorption of Topotecan through the Inhibition of Intestinal Xenobiotic Efflux Transporter, Breast Cancer Resistance Protein, by Excipients, 35(7) Drug Metabolism and Disposition 1142-1148 (2007).
International Search Report dated Oct. 17, 2013, in PCT/US2013/039540.
International Search Report dated Aug. 26, 2013, in PCT/US2013/039499.
Rowbottom MV, et al. "Identification of 1-(3-(6,7-dimethoxyquinazolin-4-yloxy)phenyl)-3-(5-(1,1,1-trifluoro-2-methylpropan-2-yl)isoxazol-3-yl)urea hydrochloride (CEP-32496), a highly potent and orally efficacious inhibitor of V-RAF murine sarcoma oncogene homologue B1 (BRAF) V600E," J. Med. Chem. 55:1082-1105, 2012.
McMahon, "VEGF Receptor Signaling in Tumor Angiogenesis," The Oncologist, 2000, 5(suppl 1):3-10.
Pinedo et al., "Translational Research: The Role of VEGF in Tumor Andiogenesis," The Oncologist, 2000, 5(suppl 1):1-2.
International Search Report and Written Opinion dated Feb. 23, 2015, in PCT Application, PCT/US2014/063444.

\* cited by examiner

CRYSTALLINE FORMS OF THERAPEUTIC COMPOUNDS AND USES THEREOF

CROSS-REFERENCE TO RELATED APPLICATION

This application is a continuation of U.S. patent application Ser. No. 16/806,819, filed Mar. 2, 2020, now U.S. Pat. No. 10,975,090, which is a continuation of U.S. patent application Ser. No. 16/184,760 filed Nov. 8, 2018, now U.S. Pat. No. 10,618,960, which is a continuation of U.S. patent application Ser. No. 15/712,645 filed Sep. 22, 2107, now U.S. Pat. No. 10,160,765, which is a continuation of U.S. patent application Ser. No. 14/981,105, filed Dec. 28, 2015, now U.S. Pat. No. 9,790,232, which is a division of U.S. patent application Ser. No. 14/530,092 filed Oct. 31, 2014, now U.S. Pat. No. 9,458,169, which claims the benefit of U.S. Provisional Patent applications 61/898,741 filed Nov. 1, 2013, 62/039,177 filed Aug. 19, 2014, and 62/039,192 filed Aug. 19, 2014. The entire contents of all of these applications are incorporated by reference herein.

FIELD OF THE INVENTION

This invention relates to crystalline forms of a therapeutic compound useful for treating diseases, including proliferative diseases and diseases associated with angiogenesis, such as cancer and macular degeneration.

BACKGROUND OF THE INVENTION

Growth factors play an important role in angiogenesis, lymphangiogenesis, and vasculogenesis. Growth factors regulate angiogenesis in a variety of processes including embryonic development, wound healing, and several aspects of female reproductive function. Undesirable or pathological angiogenesis is associated with diseases including diabetic retinopathy, psoriasis, cancer, rheumatoid arthritis, atheroma, Kaposi's sarcoma, and hemangioma (Fan et al., 1995, *Trends Pharmacol. Sci.* 16: 57 66; Folkman, 1995, *Nature Medicine* 1: 27 31). Angiogenic ocular conditions represent the leading cause of irreversible vision loss in developed countries. In the United States, for example, retinopathy of prematurity, diabetic retinopathy, and age-related macular degeneration are the principal causes of blindness in infants, working age adults, and the elderly, respectively. Efforts have been developed to inhibit angiogenesis in the treatment of these conditions (R. Roskoski Jr., *Critical Reviews in Oncology/Hematology*, 62 (2007), 179-213).

Therefore, there is a need for new therapeutic compounds for the treatment of diseases associated with the aberrant signaling of growth factors and diseases associated with angiogenesis, such as cancer, macular degeneration, and diabetic retinopathy.

SUMMARY OF THE INVENTION

In one aspect, the present invention relates to crystalline forms of compound 7-(3-(4-(4-fluoro-2-methyl-1H-indol-5-yloxy)-6-methoxyquinazolin-7-yloxy)propyl)-2-oxa-7-azaspiro[3.5]nonane, referred to herein as Compound 3 and shown below:

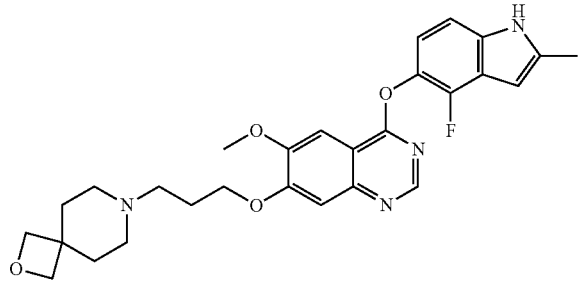 [SMILES: COc1cc2c(Oc3ccc4[nH]c(C)cc4c3F)ncnc2cc1OCCCN1CCC2(CC1)COC2]

(Compound 3)

In one embodiment, the present invention is Compound 3 depicted above, 7-(3-(4-(4-fluoro-2-methyl-1H-indol-5-yloxy)-6-methoxyquinazolin-7-yloxy)propyl)-2-oxa-7-azaspiro[3.5] nonane, in crystalline Form A. In certain embodiments, the crystalline form is crystalline Form A having an X-Ray Powder Diffraction (XRPD) pattern with peaks at about 6.11, 9.63, 16.41, 18.60, 20.36 and 23.01±0.3 degrees two theta or 14.45, 9.17, 5.40, 4.77, 4.36 and 3.86±0.3 Å in d-spacing. In further embodiments, crystalline Form A further has XRPD peaks at about 11.46, 12.26, 18.16, 19.51, 21.12 and 25.71±0.3 degrees two theta or 7.71, 7.22, 4.88, 4.55, 4.20 and 3.46±0.3 Å in d-spacing. In further embodiments, crystalline Form A further has XRPD peaks at about 11.10, 15.66, 17.54, 22.31, 24.79 and 28.90±0.3 degrees two theta or 7.96, 5.65, 5.05, 3.98, 3.59 and 3.09±0.3 Å in d-spacing. In still further embodiments, crystalline Form A has an XRPD pattern with peaks at about 6.11, 9.63, 11.10, 11.46, 12.26, 15.66, 16.41, 17.54, 18.16, 18.60, 19.51, 20.36, 21.12, 22.31, 23.01, 24.79, 25.71 and 28.90±0.3 degrees two theta or 14.45, 9.17, 7.96, 7.71, 7.22, 5.65, 5.40, 5.05, 4.88, 4.77, 4.55, 4.36, 4.20, 3.98, 3.86, 3.59, 3.46 and 3.09±0.3 Å in d-spacing.

In other embodiments, the present invention provides 7-(3-(4-(4-fluoro-2-methyl-1H-indol-5-yloxy)-6-methoxy-quinazolin-7-yloxy)propyl)-2-oxa-7-azaspiro[3.5]nonane, in crystalline Form B. In certain embodiments, the crystalline form is crystalline Form B having an X-Ray Powder Diffraction (XRPD) pattern with peaks at about 7.70, 13.53, 17.27, 18.44, 19.73, 23.10 and 26.07±0.3 degrees two theta or 11.47, 6.54, 5.13, 4.81, 4.50, 3.85 and 3.41±0.3 Å in d-spacing. In further embodiments, crystalline Form B further has XRPD peaks at about 9.87, 12.88, 14.40, 15.45, 21.14 and 26.84±0.3 degrees two theta or 8.96, 6.87, 6.14, 5.73, 4.20 and 3.32±0.3 Å in d-spacing. In further embodiments, crystalline Form B further has XRPD peaks at about 10.69, 16.42, 18.90, 22.56, and 29.12±0.3 degrees two theta or 8.27, 5.39, 4.69, 3.94 and 3.06±0.3 Å in d-spacing. In still further embodiments, crystalline Form B has an XRPD pattern with peaks at about 7.70, 9.87, 10.69, 12.88, 13.53, 14.40, 15.45, 16.42, 17.27, 18.44, 18.90, 19.73, 21.14, 22.56, 23.10, 26.07, 26.84 and 29.12±0.3 degrees two theta or 11.47, 8.96, 8.27, 6.87, 6.54, 6.14, 5.73, 5.39, 5.13, 4.81, 4.69, 4.50, 4.20, 3.94, 3.85, 3.41, 3.32 and 3.06±0.3 Å in d-spacing.

In one aspect, the present invention relates to a compound having the formula

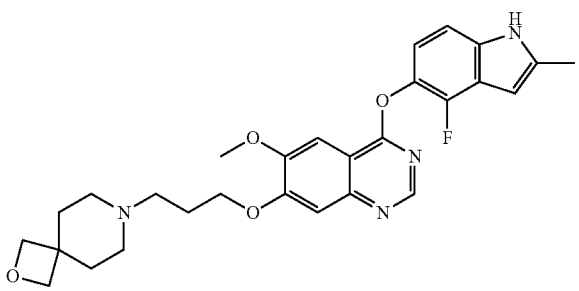

in crystalline Form A.

In another aspect, the present invention relates to a crystalline form of a compound having the formula

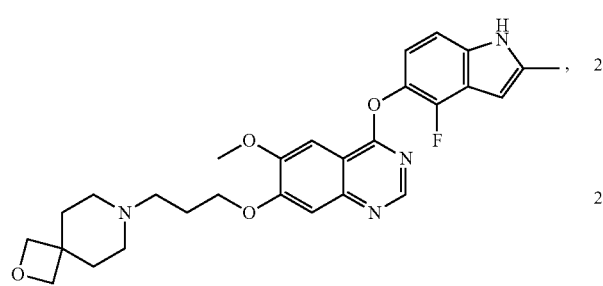

wherein said crystalline form is crystalline Form A having an X-ray powder diffraction (XRPD) pattern with peaks at about 6.11, 9.63, 16.41, 18.60, 20.36 and 23.01±0.3 degrees two theta, or 14.45, 9.17, 5.40, 4.77, 4.36 and 3.86±0.3 Å in d-spacing.

In another embodiment, the present invention relates to a compound having the formula

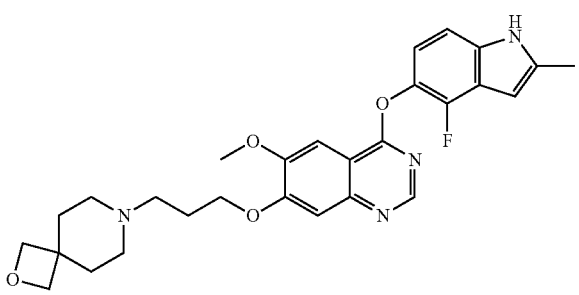 [SMILES: COc1cc2c(Oc3ccc4[nH]c(C)cc4c3F)ncnc2cc1OCCCN1CCC2(CC1)COC2]

in crystalline Form B.

In another embodiment, the present invention relates to a crystalline form of a compound having the formula

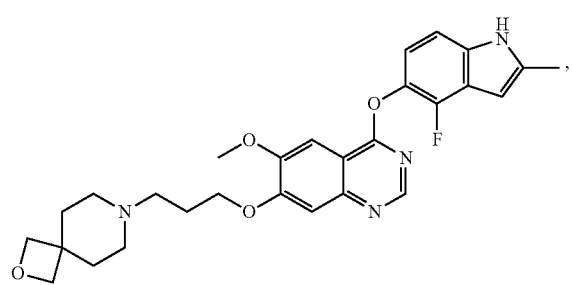 [SMILES: COc1cc2c(Oc3ccc4[nH]c(C)cc4c3F)ncnc2cc1OCCCN1CCC2(CC1)COC2]

wherein said crystalline form is crystalline Form B having an X-Ray Powder Diffraction (XRPD) pattern with peaks at about 7.70, 13.53, 17.27, 18.44, 19.73, 23.10 and 26.07±0.3 degrees two theta or 11.47, 6.54, 5.13, 4.81, 4.50, 3.85 and 3.41±0.3 Å in d-spacing.

In another aspect, the present invention relates to a process for preparing a crystalline form of Compound 3. In certain embodiments, the present invention relates to a method for preparing crystalline Form A of Compound 3. In additional embodiments, the method of preparing crystalline Form A comprises wet-milling a slurry comprising an amorphous form of Compound 3 and a non-ionic surfactant to obtain nanoparticles of the compound. In further embodiments, the resulting nanoparticles of crystalline Form A have an XRPD pattern with peaks at about 6.11, 9.63, 16.41, 18.60, 20.36 and 23.01±0.3 degrees two theta or 14.45, 9.17, 5.40, 4.77, 4.36 and 3.86±0.3 Å in d-spacing. In further embodiments, crystalline Form A further has XRPD peaks at about 11.46, 12.26, 18.16, 19.51, 21.12 and 25.71±0.3 degrees two theta or 7.71, 7.22, 4.88, 4.55, 4.20 and 3.46±0.3 Å in d-spacing. In further embodiments, crystalline Form A further has XRPD peaks at about 11.10, 15.66, 17.54, 22.31, 24.79 and 28.90±0.3 degrees two theta or 7.96, 5.65, 5.05, 3.98, 3.59 and 3.09±0.3 Å in d-spacing. In still further embodiments, crystalline Form A has an XRPD pattern with peaks at about 6.11, 9.63, 11.10, 11.46, 12.26, 15.66, 16.41, 17.54, 18.16, 18.60, 19.51, 20.36, 21.12, 22.31, 23.01, 24.79, 25.71 and 28.90±0.3 degrees two theta or 14.45, 9.17, 7.96, 7.71, 7.22, 5.65, 5.40, 5.05, 4.88, 4.77, 4.55, 4.36, 4.20, 3.98, 3.86, 3.59, 3.46 and 3.09±0.3 Å in d-spacing.

In other embodiments, the present invention relates to a method for preparing crystalline Form B of Compound 3. In certain embodiments, the method of preparing crystalline Form B comprises a) dissolving the amorphous form of Compound 3 in water and acetone; b) crystallizing Compound 3 from a solvent mixture comprising water and acetone; and c) isolating the crystalline Form B of Compound 3 from the solvent mixture. In certain embodiments, the starting Compound 3 is amorphous. In particular embodiments, the method of preparing crystalline Form B utilizes a solvent mixture consisting of 4:1 acetone:water. In other embodiments, the method of preparing crystalline Form B further comprises the step of heating the solvent mixture to dissolve the compound and/or cooling the solvent mixture to allow crystal formation. In some embodiments, the resulting crystalline Form B has an XRPD pattern with peaks at about 7.70, 13.53, 17.27, 18.44, 19.73, 23.10 and 26.07±0.3 degrees two theta or 11.47, 6.54, 5.13, 4.81, 4.50, 3.85 and 3.41±0.3 Å in d-spacing. In further embodiments, crystalline Form B further has XRPD peaks at about 9.87, 12.88, 14.40, 15.45, 21.14 and 26.84±0.3 degrees two theta or 8.96, 6.87, 6.14, 5.73, 4.20 and 3.32±0.3 Å in d-spacing. In further embodiments, crystalline Form B further has XRPD peaks at about 10.69, 16.42, 18.90, 22.56, and 29.12±0.3 degrees two theta or 8.27, 5.39, 4.69, 3.94 and 3.06±0.3 Å in d-spacing. In still further embodiments, crystalline Form B has an XRPD pattern with peaks at about 7.70, 9.87, 10.69, 12.88, 13.53, 14.40, 15.45, 16.42, 17.27, 18.44, 18.90, 19.73, 21.14, 22.56, 23.10, 26.07, 26.84 and 29.12±0.3 degrees two theta or 11.47, 8.96, 8.27, 6.87, 6.54, 6.14, 5.73, 5.39, 5.13, 4.81, 4.69, 4.50, 4.20, 3.94, 3.85, 3.41, 3.32 and 3.06±0.3 Å in d-spacing.

In yet another aspect, the present invention relates to pharmaceutical compositions and kits to treat diseases, including proliferative diseases, ocular diseases, dermatological diseases, inflammatory diseases, autoimmune diseases, auto-inflammatory diseases, and metabolic diseases comprising a crystalline form of Compound 3. In a further aspect, the present invention provides methods of using a crystalline form of Compound 3 to study the inhibition of growth factor signaling and/or to treat and/or prevent proliferative diseases, ocular diseases, dermatological diseases, inflammatory diseases, autoimmune diseases, auto-inflammatory diseases, and metabolic diseases. In certain particular aspects, a crystalline form of Compound 3 is used in treating diseases associated with angiogenesis.

In another aspect, the present invention provides pharmaceutical compositions comprising crystalline forms of Compound 3, wherein the pharmaceutical compositions optionally comprise a pharmaceutically acceptable carrier. In certain embodiments, the pharmaceutical compositions described herein include a therapeutically effective amount of a crystalline form of Compound 3. In certain embodiments, the pharmaceutical composition may be useful for treating proliferative diseases (e.g., cancers, benign neoplasms, inflammatory diseases, autoimmune diseases) and/or ocular diseases (e.g., macular degeneration, glaucoma, diabetic retinopathy, retinoblastoma, edema, uveitis, dry eye, blepharitis, and post-surgical inflammation) in a subject in need thereof. The pharmaceutical composition may also be useful for inhibiting abnormal angiogenesis and/or aberrant signaling of a growth factor in a subject or cell.

In some embodiments, the crystalline forms of Compound 3 may be intended for delivery in a subject's tissues having mucus (e.g., eye, respiratory tract, gastrointestinal tract, genito-urinary tract), which is a viscoelastic and adhesive substance that traps most foreign objects (e.g., microorganisms, particles, dust). Compound or particles that are immobilized in the mucus are quickly eliminated by mucus clearance mechanisms; therefore, they are not able to effectively deliver the intended therapeutic effect. In these tissues, for the compound to effective, it must quickly penetrate the mucus and/or avoid mucus clearance mechanisms. Accordingly, modifying mucoadhesive compounds or particles containing compounds with a coating to reduce the mucoadhesiveness, and decreasing the size of the particles of compound may allow for efficient delivery and therapeutic effect.

In one aspect of the invention, the crystalline forms of Compound 3 of the invention are formulated into mucus penetrating particles or mucus penetrating crystals (collectively, MPPs) suitable for administration (e.g., topical, inhalation, injection) to tissues of the subject having mucus (e.g., eye, respiratory tract, gastrointestinal tract, genito-urinary tract). In certain embodiments, the particles comprising a crystalline form of Compound 3 (e.g., crystalline Form B) are mucus penetrating. The MPPs may include a coating surrounding a core. The core may contain primarily a crystalline form of Compound 3, or the core may be a polymeric core with the crystalline form of Compound 3 encapsulated in the polymer. In certain embodiments, the MPPs are nanoparticles (e.g., particles having an average diameter of at least about 10 nm and less than about 1 µm). The MPPs may be useful in delivering the pharmaceutical agent to a subject. In certain embodiments, the MPPs are capable of delivering the crystalline form of Compound 3 in or through mucus of a subject.

Another aspect of the invention relates to pharmaceutical compositions comprising particles comprising crystalline forms of Compound 3. In one particular embodiment, the particles comprise crystalline Form B of Compound 3. In another embodiment, the particles comprise crystalline Form A of Compound 3. In certain embodiments, the pharmaceutical compositions are useful in delivering crystalline forms of Compound 3 to a subject.

In another aspect of the invention, the present invention provides pharmaceutical compositions comprising a plurality of particles comprising (i) a core comprising a crystalline form of Compound 3, and (ii) a coating of a surface altering agent surrounding the core, wherein the surface altering agent is present on the outer surface of the core at a density of at least 0.01 surface altering agent per $nm^2$, and optionally, at least one pharmaceutically acceptable excipient. In some embodiments, the surface altering agent is a triblock copolymer of the structure (hydrophilic block)-(hydrophobic block)-(hydrophilic block). In some aspects, the triblock copolymer is a PLURONIC® or poloxamer. In other aspects, the surface altering agent is a poly(vinyl alcohol) or a polysorbate. In one preferred aspect, the core comprises crystalline Form B of Compound 3. In another, the core comprises crystalline Form A of Compound 3

In certain embodiments, the compound, particle, or pharmaceutical composition is formulated to be mucus penetrating.

Another aspect of the present invention relates to methods of treating and/or preventing a disease associated with abnormal angiogenesis in a subject in need thereof.

Another aspect of the present invention relates to methods of treating and/or preventing a disease associated with aberrant signaling of a growth factor signaling pathway in a subject in need thereof.

In another aspect, the present invention provides methods of inhibiting angiogenesis in a subject in need thereof.

In another aspect, the present invention provides methods of inhibiting aberrant signaling of a growth factor signaling pathway in a subject or cell. In certain embodiments, the growth factor is associated with angiogenesis. In certain embodiments, the growth factor is VEGF.

The methods of the present invention include administering to a subject an effective amount of a crystalline form of Compound 3 or pharmaceutical compositions thereof of the invention. The diseases include proliferative diseases, ocular diseases, dermatological diseases, inflammatory diseases, autoimmune diseases, autoinflammatory diseases, and metabolic diseases. In certain embodiments, the effective amount is a prophylactically effective amount.

In another aspect, the present invention provides kits comprising a crystalline form of Compound 3. The kits of the invention may include a single dose or multiple doses of a crystalline form of Compound 3, or pharmaceutical compositions thereof. The provided kits may be useful for the treatment of proliferative diseases, ocular diseases, dermatological diseases, inflammatory diseases, autoimmune diseases, autoinflammatory diseases, and metabolic diseases. In certain embodiments, the kits described herein may be useful in treating and/or preventing a disease associated with abnormal angiogenesis and/or with aberrant signaling of a growth factor in a subject in need thereof. The kits may also be useful for inhibiting abnormal angiogenesis and/or aberrant signaling of a growth factor signaling pathway in a subject in need thereof. In certain embodiments, the kit further includes instructions for administering crystalline forms of Compound 3 of the invention. The kits may also include packaging information describing the use or prescribing information for the subject or a health care professional. Such information may be required by a regulatory agency such as the U.S. Food and Drug Administration (FDA). The kit may also optionally include a device for administration of Compound 3 crystalline forms or composition thereof, for example, a dropper for ocular administration or a syringe for parenteral administration.

The details of one or more embodiments of the invention are set forth herein. Other features, objects, and advantages of the invention will be apparent from the Detailed Description, the Figures, the Examples, and the Claims.

DEFINITIONS

Figure 1:
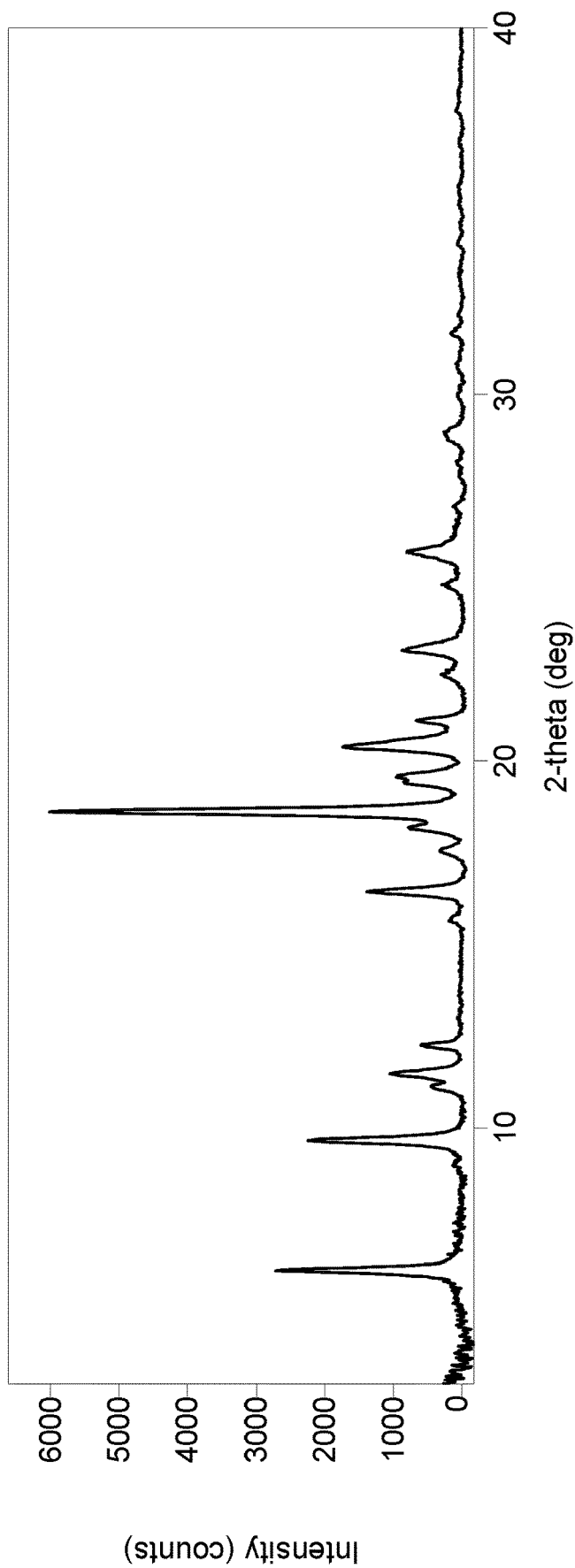
FIG. 1 provides a representative X-Ray Powder Diffraction (XRPD) pattern for crystalline Form A of Compound 3.

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

As used herein, when referring to X-Ray Powder Diffraction (XRPD) peak positions, "about" means ±0.3, preferably ±0.2, more preferably ±0.1, more preferably ±0.05, and still more preferably ±0.02

OTHER DEFINITIONS

The following definitions are more general terms used throughout the present application.

The term "polymorphs" refers to a crystalline form of a compound (or a salt, hydrate, or solvate thereof) in a particular crystal packing arrangement. All polymorphs have the same elemental composition. Different crystalline forms usually have different X-ray diffraction patterns (e.g., XRPD patterns), infrared spectra, melting points, density, hardness, crystal shape, optical and electrical properties, stability, and/or solubility. Recrystallization solvent, rate of crystallization, storage temperature, and other factors may cause one crystal form to dominate. One particular method for characterizing different crystalline forms of a compound is X-Ray Powder Diffraction (XRPD) analysis, which is a technique that is well-known in the art. Various polymorphs of a compound can be prepared by crystallization under different conditions. As used herein, the term "crystal form" or "crystalline form" refers to one particular polymorph of a compound that possesses one or more particular identifying characteristics, for example, a particular X-ray diffraction or XRPD pattern.

A "subject" to which administration is contemplated includes, but is not limited to, humans (i.e., a male or female of any age group, e.g., a pediatric subject (e.g., infant, child, adolescent) or adult subject (e.g., young adult, middle-aged adult, or senior adult)) and/or other non-human animals, for example, mammals (e.g., primates (e.g., cynomolgus monkeys, rhesus monkeys); commercially relevant mammals such as cattle, pigs, horses, sheep, goats, cats, and/or dogs) and birds (e.g., commercially relevant birds such as chickens, ducks, geese, and/or turkeys). In certain embodiments, the animal is a mammal. The animal may be a male or female at any stage of development. The animal may be a transgenic animal or genetically engineered animal. In certain embodiments, the subject is a non-human animal. In certain embodiments, the animal is fish. A "patient" refers to a human subject in need of treatment of a disease.

The terms "administer," "administering," or "administration," as used herein, refer to implanting, absorbing, ingesting, injecting, inhaling, or otherwise introducing a crystalline form of Compound 3, or a pharmaceutical composition thereof, in or on a subject.

As used herein, the terms "treatment," "treat," and "treating" refer to reversing, alleviating, delaying the onset of, or inhibiting the progress of a disease described herein. In some embodiments, treatment may be administered after one or more signs or symptoms of the disease have developed or have been observed. In other embodiments, treatment may be administered in the absence of signs or symptoms of the disease. For example, treatment may be administered to a susceptible subject prior to the onset of symptoms (e.g., in light of a history of symptoms and/or in light of genetic or other susceptibility factors) or exposure to a pathogen). Treatment may also be continued after symptoms have resolved, for example, to delay or prevent recurrence.

As used herein, the terms "condition," "disease," and "disorder" are used interchangeably.

An "effective amount" of a Compound 3 crystalline form described herein refers to an amount sufficient to elicit a desired biological response, i.e., treating the condition. As will be appreciated by those of ordinary skill in this art, the effective amount of a crystalline form of Compound 3 described herein may vary depending on such factors as the desired biological endpoint, the pharmacokinetics of the Compound 3 crystalline form, the condition being treated, the mode of administration, and the age and health of the subject. An effective amount encompasses therapeutic and prophylactic treatment. For example, in treating cancer, an effective amount of a Compound 3 crystalline form described herein may reduce the tumor burden or stop the growth or spread of a tumor. In treating macular degeneration, an effective amount of a Compound 3 crystalline form described herein may improve sight, reduce the risk of vision loss, or prevent central vision loss from worsening.

A "therapeutically effective amount" of a Compound 3 crystalline form described herein is an amount sufficient to provide a therapeutic benefit in the treatment of a condition or to delay or minimize one or more symptoms associated with the condition. A therapeutically effective amount of a Compound 3 crystalline form described herein means an amount of a crystalline form of Compound 3, alone or in combination with other therapies, which provides a therapeutic benefit in the treatment of the condition. The term "therapeutically effective amount" can encompass an amount that improves overall therapy, reduces or avoids symptoms, signs, or causes of the condition, and/or enhances the therapeutic efficacy of another therapeutic agent. In certain embodiments, a "therapeutically effective amount" of crystalline form of Compound 3 or composition thereof is the amount needed to inhibit angiogenesis in a subject.

A "prophylactically effective amount" of a Compound 3 crystalline form described herein is an amount sufficient to prevent a condition, or one or more symptoms associated with the condition or prevent its recurrence. A prophylactically effective amount of a Compound 3 crystalline form described herein means an amount of a crystalline form of Compound 3, alone or in combination with other agents, which provides a prophylactic benefit in the prevention of the condition. The term "prophylactically effective amount" can encompass an amount that improves overall prophylaxis or enhances the prophylactic efficacy of another prophylactic agent.

As used herein, the term "growth factor" refers to a naturally occurring substance (e.g., a protein or a steroid hormone) capable of stimulating cellular growth, proliferation, and/or cellular differentiation. Growth factors may act as signaling molecules between cells and/or promote cell differentiation and maturation.

A "proliferative disease" refers to a disease that occurs due to abnormal growth or extension by the multiplication of cells (Walker, *Cambridge Dictionary of Biology*; Cambridge University Press: Cambridge, UK, 1990). A proliferative disease may be associated with: 1) the pathological proliferation of normally quiescent cells; 2) the pathological migration of cells from their normal location (e.g., metastasis of neoplastic cells); 3) the pathological expression of proteolytic enzymes such as the matrix metalloproteinases (e.g., collagenases, gelatinases, and elastases); or 4) the pathological angiogenesis as in proliferative retinopathy and tumor metastasis. Exemplary proliferative diseases include cancers (i.e., "malignant neoplasms"), benign neoplasms, angiogenesis, inflammatory diseases, and autoimmune diseases.

As used herein, the term "angiogenesis" refers to the physiological process through which new blood vessels form from pre-existing vessels. Angiogenesis is distinct from vasculogenesis, which is the de novo formation of endothelial cells from mesoderm cell precursors. The first vessels in a developing embryo form through vasculogenesis, after which angiogenesis is responsible for most blood vessel growth during normal or abnormal development. Angiogenesis is a vital process in growth and development, as well as in wound healing and in the formation of granulation tissue. However, angiogenesis is also a fundamental step in the transition of tumors from a benign state to a malignant one, leading to the use of angiogenesis inhibitors in the treatment of cancer. Angiogenesis may be chemically stimulated by angiogenic proteins, such as growth factors (e.g., VEGF).

The terms "neoplasm" and "tumor" are used herein interchangeably and refer to an abnormal mass of tissue wherein the growth of the mass surpasses and is not coordinated with the growth of a normal tissue. A neoplasm or tumor may be "benign" or "malignant," depending on the following characteristics: degree of cellular differentiation (including morphology and functionality), rate of growth, local invasion, and metastasis. A "benign neoplasm" is generally well differentiated, has characteristically slower growth than a malignant neoplasm, and remains localized to the site of origin. In addition, a benign neoplasm does not have the capacity to infiltrate, invade, or metastasize to distant sites. Exemplary benign neoplasms include, but are not limited to, lipoma, chondroma, adenomas, acrochordon, senile angiomas, seborrheic keratoses, lentigos, and sebaceous hyperplasias. In some cases, certain "benign" tumors may later give rise to malignant neoplasms, which may result from additional genetic changes in a subpopulation of the tumor's neoplastic cells, and these tumors are referred to as "pre-malignant neoplasms." An exemplary pre-malignant neoplasm is a teratoma. In contrast, a "malignant neoplasm" is generally poorly differentiated (anaplasia) and has characteristically rapid growth accompanied by progressive infiltration, invasion, and destruction of the surrounding tissue. Furthermore, a malignant neoplasm generally has the capacity to metastasize to distant sites. The term "metastasis," "metastatic," or "metastasize" refers to the spread or migration of cancerous cells from a primary or original tumor to another organ or tissue and is typically identifiable by the presence of a "secondary tumor" or "secondary cell mass" of the tissue type of the primary or original tumor and not of that of the organ or tissue in which the secondary (metastatic) tumor is located. For example, a prostate cancer that has migrated to bone is said to be metastasized prostate cancer and includes cancerous prostate cancer cells growing in bone tissue.

As used herein, the term "cancer" refers to a malignant neoplasm (*Stedman's Medical Dictionary*, 25th ed.; Hensyl ed.; Williams & Wilkins: Philadelphia, 1990). Exemplary cancers include, but are not limited to: acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma); choriocarcinoma; chordoma; craniopharyngioma; colorectal cancer (e.g., colon cancer, rectal cancer, colorectal adenocarcinoma); connective tissue cancer; epithelial carcinoma; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarcinoma); Ewing's sarcoma; ocular cancer (e.g., intraocular melanoma, retinoblastoma); familiar hypereosinophilia; gall bladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); hematopoietic cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL)); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., Waldenström's macroglobulinemia), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungiodes, Sezary syndrome), angioimmunoblastic T-cell lymphoma, extranodal natural killer T-cell lymphoma, enteropathy type T-cell lymphoma, subcutaneous panniculitis-like T-cell lymphoma, and anaplastic large cell lymphoma); a mixture of one or more leukemia/lymphoma as described above; and multiple myeloma (MM)), heavy chain disease (e.g., alpha chain disease, gamma chain disease, mu chain disease); hemangioblastoma; hypopharynx cancer; inflammatory myofibroblastic tumors; immunocytic amyloidosis; kidney cancer (e.g., nephroblastoma a.k.a. Wilms' tumor, renal cell carcinoma); liver cancer (e.g., hepatocellular cancer (HCC), malignant hepatoma); lung cancer (e.g., bronchogenic carcinoma, small cell lung cancer (SCLC), non-small cell lung cancer (NSCLC), adenocarcinoma of the lung); leiomyosarcoma (LMS); mastocytosis (e.g., systemic mastocytosis); muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendoctrine tumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic andenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva).

As used herein, the term "inflammatory disease" or "inflammation" refers to a disease caused by, resulting from, or resulting in inflammation. The term "inflammatory disease" may also refer to a dysregulated inflammatory reaction that causes an exaggerated response by macrophages, granulocytes, and/or T-lymphocytes leading to abnormal tissue damage and/or cell death. An inflammatory disease can be either an acute or chronic inflammatory condition and can result from infections or non-infectious causes. Inflammatory diseases include, without limitation, atherosclerosis, arteriosclerosis, autoimmune disorders, multiple sclerosis, systemic lupus erythematosus, polymyalgia rheumatica (PMR), gouty arthritis, degenerative arthritis, tendonitis, bursitis, psoriasis, cystic fibrosis, arthrosteitis, rheumatoid arthritis, inflammatory arthritis, Sjogren's syndrome, giant cell arteritis, progressive systemic sclerosis (scleroderma), ankylosing spondylitis, polymyositis, dermatomyosifis, pemphigus, pemphigoid, diabetes (e.g., Type I), myasthenia gravis, Hashimoto's thyroditis, Graves' disease, Goodpasture's disease, mixed connective tissue disease, sclerosing cholangitis, inflammatory bowel disease, Crohn's disease, ulcerative colitis, pernicious anemia, inflammatory dermatoses, usual interstitial pneumonitis (UIP), asbestosis, silicosis, bronchiectasis, berylliosis, talcosis, pneumoconiosis, sarcoidosis, desquamative interstitial pneumonia, lymphoid interstitial pneumonia, giant cell interstitial pneumonia, cellular interstitial pneumonia, extrinsic allergic alveolitis, Wegener's granulomatosis and related forms of angiitis (temporal arteritis and polyarteritis nodosa), inflammatory dermatoses, hepatitis, delayed-type hypersensitivity reactions (e.g., poison ivy dermatitis), pneumonia, respiratory tract inflammation, Adult Respiratory Distress Syndrome (ARDS), encephalitis, immediate hypersensitivity reactions, asthma, hayfever, allergies, acute anaphylaxis, rheumatic fever, glomerulonephritis, pyelonephritis, cellulitis, cystitis, chronic cholecystitis, ischemia (ischemic injury), reperfusion injury, allograft rejection, host-versus-graft rejection, appendicitis, arteritis, blepharitis, bronchiolitis, bronchitis, cervicitis, cholangitis, chorioamnionitis, conjunctivitis, dacryoadenitis, dermatomyositis, endocarditis, endometritis, enteritis, enterocolitis, epicondylitis, epididymitis, fasciitis, fibrositis, gastritis, gastroenteritis, gingivitis, ileitis, iritis, laryngitis, myelitis, myocarditis, nephritis, omphalitis, oophoritis, orchitis, osteitis, otitis, pancreatitis, parotitis, pericarditis, pharyngitis, pleuritis, phlebitis, pneumonitis, proctitis, prostatitis, rhinitis, salpingitis, sinusitis, stomatitis, synovitis, testitis, tonsillitis, urethritis, urocystitis, uveitis, vaginitis, vasculitis, vulvitis, vulvovaginitis, angitis, chronic bronchitis, osteomylitis, optic neuritis, temporal arteritis, transverse myelitis, necrotizing fasciitis, and necrotizing enterocolitis. Ocular inflammatory diseases include, but are not limited to, allergy of the eye, uveitis (e.g., anterior uveitis, intermediate uveitis, and posterior uveitis), conjunctivitis, panuveitis, cyclitis, scleritis, episcleritis, optic neuritis, retrobulbar optic neuritis, keratitis (e.g., immune keratitis and infectious keratitis), blepharitis, meibomian gland disease or dysfunction, corneal ulcer, conjunctival ulcer and symptoms caused by them, ocular inflammatory diseases caused by ocular disorders, ocular inflammatory diseases caused by a physical injury, post-surgical inflammation, and dry eye (e.g., dry eye syndrome).

As used herein, an "autoimmune disease" refers to a disease arising from an inappropriate immune response of the body of a subject against substances and tissues normally present in the body. In other words, the immune system mistakes some part of the body as a pathogen and attacks its own cells. This may be restricted to certain organs (e.g., in autoimmune thyroiditis) or involve a particular tissue in different places (e.g., Goodpasture's disease which may affect the basement membrane in both the lung and kidney). The treatment of autoimmune diseases is typically with immunosuppressants, e.g., medications that decrease the immune response. Exemplary autoimmune diseases include, but are not limited to, glomerulonephritis, Goodpasture's syndrome, necrotizing vasculitis, lymphadenitis, peri-arteritis nodosa, systemic lupus erythematosis, rheumatoid, arthritis, psoriatic arthritis, systemic lupus erythematosis, psoriasis, ulcerative colitis, systemic sclerosis, dermatomyositis/polymyositis, anti-phospholipid antibody syndrome, scleroderma, perphigus vulgaris, ANCA-associated vasculitis (e.g., Wegener's granulomatosis, microscopic polyangiitis), urveitis, Sjogren's syndrome, Crohn's disease, Reiter's syndrome, ankylosing spondylitis, Lyme arthritis, Guillain-Barre syndrome, Hashimoto's thyroiditis, and cardiomyopathy.

The term "autoinflammatory disease" refers to a category of diseases that are similar but different from autoimmune diseases. Autoinflammatory and autoimmune diseases share common characteristics in that both groups of disorders result from the immune system attacking a subject's own tissues and result in increased inflammation. In autoinflammatory diseases, a subject's innate immune system causes inflammation for unknown reasons. The innate immune system reacts even though it has never encountered autoantibodies or antigens in the subject. Autoinflammatory disorders are characterized by intense episodes of inflammation that result in such symptoms as fever, rash, or joint swelling. These diseases also carry the risk of amyloidosis, a potentially fatal buildup of a blood protein in vital organs. Autoinflammatory diseases include, but are not limited to, familial Mediterranean fever (FMF), neonatal onset multisystem inflammatory disease (NOMID), tumor necrosis factor (TNF) receptor-associated periodic syndrome (TRAPS), deficiency of the interleukin-1 receptor antagonist (DIRA), and Behçet's disease.

The term "biological sample" refers to any sample including tissue samples (such as tissue sections and needle biopsies of a tissue); cell samples (e.g., cytological smears (such as Pap or blood smears) or samples of cells obtained by microdissection); samples of whole organisms (such as samples of yeasts or bacteria); or cell fractions, fragments or organelles (such as obtained by lysing cells and separating the components thereof by centrifugation or otherwise). Other examples of biological samples include blood, serum, urine, semen, fecal matter, cerebrospinal fluid, interstitial fluid, mucus, tears, sweat, pus, biopsied tissue (e.g., obtained by a surgical biopsy or needle biopsy), nipple aspirates, milk, vaginal fluid, saliva, swabs (such as buccal swabs), or any material containing biomolecules that is derived from a first biological sample. Biological samples also include those biological samples that are transgenic, such as transgenic oocyte, sperm cell, blastocyst, embryo, fetus, donor cell, or cell nucleus.

The term "ocular disease" or "ocular disorder" refers to any eye disease and/or disorder. For example, ocular diseases can be disorders of the eyelid, lacrimal system and orbit, disorders of conjunctiva, disorders of sclera, cornea, iris and ciliary body, disorders of choroid, disorders of retina, glaucoma, disorders of optic nerve and visual pathways, ocular neovascularization diseases or disorders, ocular inflammatory diseases, or disorders of ocular muscles. Additionally, ocular disease can also refer to discomfort following injury, surgery, or laser treatment. Diseases and disorders of the eye or ocular diseases include, but are not limited to, retinopathy, diabetic retinopathy, retinal vein occlusion, macular degeneration, age-related macular degeneration, dry eye syndrome, blepharitis, inflammatory meibomian gland disease, uveitis, allergic conjunctivitis, glaucoma, macular edema, diabetic macular edema, cystoid macular edema, and rosacea (of the eye). Dry eye syndrome (DES), otherwise known as keratoconjunctivitis sicca (KCS), keratitis sicca, sicca syndrome, or xerophthalmia, is an eye disease caused by decreased tear production or increased tear film evaporation commonly found in humans and some animals.

The term "age-related macular degeneration" or "AMD" is an ocular disease which usually affects older adults and results in a loss of vision in the center of the visual field (the macula) because of damage to the retina. It occurs in "dry" and "wet" forms. It is a major cause of blindness and visual impairment in older adults (>50 years).

Macular degeneration can make it difficult or impossible to read or recognize faces, although enough peripheral vision remains to allow other activities of daily life. The macula is the central area of the retina, which provides the most detailed central vision. In the dry (nonexudative) form, cellular debris called drusen accumulate between the retina and the choroid, and the retina can become detached. In the wet (exudative) form, which is more severe, blood vessels grow up from the choroid behind the retina, and the retina can also become detached. It can be treated with laser coagulation, and with medication that stops and sometimes reverses the growth of blood vessels. Macular degeneration includes some macular dystrophies affecting younger subjects as well as age-related macular degeneration (AMD or ARMD), which is more commonly known. AMD begins with characteristic yellow deposits (drusen) in the macula, between the retinal pigment epithelium and the underlying choroid. Most patients with these early changes (referred to as age-related maculopathy) have good vision. Patients with drusen can go on to develop advanced AMD. The risk is considerably higher when the drusen are large and numerous and associated with disturbance in the pigmented cell layer under the macula. Recent research suggests that large and soft drusen are related to elevated cholesterol deposits and may respond to cholesterol-lowering agents.

The term "macular edema" refers to the ocular diseases cystoid macular edema (CME) or diabetic macular edema (DME). CME is an ocular disease which affects the central retina or macula of the eye. When this condition is present, multiple cyst-like (cystoid) areas of fluid appear in the macula and cause retinal swelling or edema. CME may accompany a variety of diseases such as retinal vein occlusion, uveitis, and/or diabetes. CME commonly occurs after cataract surgery. DME occurs when blood vessels in the retina of patients with diabetes begin to leak into the macula. These leaks cause the macula to thicken and swell, progressively distorting acute vision. While the swelling may not lead to blindness, the effect can cause a severe loss in central vision.

The term "glaucoma" refers to an ocular disease in which the optic nerve is damaged in a characteristic pattern. This can permanently damage vision in the affected eye and lead to blindness if left untreated. It is normally associated with increased fluid pressure in the eye (aqueous humor). The term ocular hypertension is used for patients with consistently raised intraocular pressure (IOP) without any associated optic nerve damage. Conversely, the term normal tension or low tension glaucoma is used for those with optic nerve damage and associated visual field loss but normal or low IOP. The nerve damage involves loss of retinal ganglion cells in a characteristic pattern. There are many different subtypes of glaucoma, but they can all be considered to be a type of optic neuropathy. Raised intraocular pressure (e.g., above 21 mmHg or 2.8 kPa) is the most important and only modifiable risk factor for glaucoma. However, some may have high eye pressure for years and never develop damage, while others can develop nerve damage at a relatively low pressure. Untreated glaucoma can lead to permanent damage of the optic nerve and resultant visual field loss, which over time can progress to blindness.

The term "uveitis" refers to an inflammatory disease of the uvea, the vascular layer of the eye sandwiched between the retina and the white of the eye (sclera). The uvea extends toward the front of the eye and consists of the iris, choroid layer and ciliary body. Uveitis includes anterior uveitis, intermediate uveitis, and posterior uveitis. A most common type of uveitis is an inflammation of the iris called iritis (anterior uveitis). Uveitis may also occur at the posterior segment of the eye (e.g., at the choroid). Inflammation of the uvea can be recurring and can cause serious problems such as blindness if left untreated (accounts for 10% of blindness globally). Early diagnosis and treatment are important to prevent the complications of uveitis.

The term "dry eye" or "dry eyes" refers to an ocular disease in which there are insufficient tears to lubricate and nourish the eye. Tears are necessary for maintaining the health of the front surface of the eye and for providing clear vision. Patients with dry eyes either do not produce enough tears or have a poor quality of tears. Dry eye is a common and often chronic problem, particularly in older adults. With each blink of the eyelids, tears are spread across the front surface of the eye, known as the cornea. Tears provide lubrication, reduce the risk of eye infection, wash away foreign matter in the eye, and keep the surface of the eyes smooth and clear. Excess tears in the eyes flow into small drainage ducts, in the inner corners of the eyelids, which drain in the back of the nose. Tears are produced by several glands (e.g., lacrimal gland) in and around the eyelids. Tear production tends to diminish with age, with various medical conditions, or as a side effect of certain medicines. Environmental conditions such as wind and dry climates can also affect tear volume by increasing tear evaporation. When the normal amount of tear production decreases or tears evaporate too quickly from the eyes, symptoms of dry eye can develop. The most common form of dry eyes is due to an inadequate amount of the water layer of tears. This condition, called keratoconjunctivitis sicca (KCS), is also referred to as "dry eye syndrome."

The term "diabetic retinopathy" refers to retinopathy (i.e., a disease of the retina) caused by complications of diabetes, which can eventually lead to blindness. Diabetic retinopathy may cause no symptoms, mild vision problems, or even blindness. Diabetic retinopathy is the result of microvascular retinal changes. Hyperglycemia-induced intramural pericyte death and thickening of the basement membrane lead to incompetence of the vascular walls. These damages change the formation of the blood-retinal barrier and also make the retinal blood vessels become more permeable. The pericyte death is caused when hyperglycemia persistently activates protein kinase C-δ (PKC-δ, encoded by Prkcd) and p38 mitogen-activated protein kinase (MAPK) to increase the expression of a previously unknown target of PKC-δ signaling, Src homology-2 domain-containing phosphatase-1 (SHP-1), a protein tyrosine phosphatase. This signaling cascade leads to PDGF receptor-dephosphorylation and a reduction in downstream signaling from this receptor, resulting in pericyte apoptosis. Small blood vessels, such as those in the eye, are especially vulnerable to poor control over blood sugar. An overaccumulation of glucose and/or fructose damages the tiny blood vessels in the retina. During the initial stage, called "nonproliferative diabetic retinopathy" (NPDR), most patients do not notice any change in their vision. Early changes that are reversible and do not threaten central vision are sometimes termed simplex retinopathy or background retinopathy. As the disease progresses, severe nonproliferative diabetic retinopathy enters an advanced, "proliferative diabetic retinopathy" (PDR) stage when blood vessels proliferate. The lack of oxygen in the retina causes fragile, new, blood vessels to grow along the retina and in the clear, gel-like vitreous humor that fills the inside of the eye, which may result in bleeding, cloudy vision, retina damage, or tractional retinal detachment.

The term "VEGF" is used interchangeably with vascular endothelial growth factor herein. VEGF includes, but is not limited to, VEGF-related proteins such as placenta growth factor (PlGF), VEGF-A, VEGF-B, VEGF-C, VEGF-D, VEGF-E, and VEGF-F. The term VEGF also covers a number of proteins from two families that result from alternate splicing of mRNA from a single, 8-exon, VEGF gene. The two different families are referred to according to their terminal exon (exon 8) splice site—the proximal splice site (denoted $VEGF_{xxx}$) or distal splice site ($VEGF_{xxxb}$). In addition, alternate splicing of exon 6 and 7 alters their heparin-binding affinity, and amino acid number (in humans: $VEGF_{121}$, $VEGF_{121b}$, $VEGF_{145}$, $VEGF_{165}$, $VEGF_{165b}$, $VEGF_{189}$, $VEGF_{206}$; the rodent orthologs of these proteins contain one fewer amino acid). These domains have important functional consequences for the VEGF splice variants, as the terminal (exon 8) splice site determines whether the proteins are pro-angiogenic (proximal splice site, expressed during angiogenesis) or anti-angiogenic (distal splice site, expressed in normal tissues). In addition, inclusion or exclusion of exons 6 and 7 mediate interactions with heparan sulfate proteoglycans (HSPGs) and neuropilin co-receptors on the cell surface, enhancing their ability to bind and activate the VEGF receptors (VEGFRs). The term "VEGF" also encompasses VEGF receptors. There are three main subtypes of VEGFR, numbered 1, 2 and 3. Also, they may be membrane-bound (mbVEGFR) or soluble (sVEGFR), depending on alternative splicing.

The term "particle" refers to a small object, fragment, or piece of a substance that may be a single element, inorganic material, organic material, or mixture thereof. Examples of particles include polymeric particles, single-emulsion particles, double-emulsion particles, coacervates, liposomes, microparticles, nanoparticles, macroscopic particles, pellets, crystals (e.g., crystalline forms of compounds or active pharmaceutical agent), aggregates, composites, pulverized, milled, or otherwise disrupted matrices, and cross-linked protein or polysaccharide particles, each of which have an average characteristic dimension of about less than about 1 mm and at least 1 nm, where the characteristic dimension, or "critical dimension," of the particle is the smallest cross-sectional dimension of the particle. A particle may be composed of a single substance or multiple substances. In certain embodiments, the particle is not a viral particle. In other embodiments, the particle is not a liposome. In certain embodiments, the particle is not a micelle. In certain embodiments, the particle is substantially solid throughout. In certain embodiments, the particle is a nanoparticle. In certain embodiments, the particle is a microparticle.

The term "nanoparticle" refers to a particle having a characteristic dimension of less than about 1 micrometer and at least about 1 nanometer, where the characteristic dimension of the particle is the smallest cross-sectional dimension of the particle. A crystalline nanoparticle is referred to as a "nanocrystal."

The term "microparticle" refers to a particle having a characteristic dimension of less than about 1 millimeter and at least about 1 micrometer, where the characteristic dimension of the particle is the smallest cross-sectional dimension of the particle.

The term "nanostructure" refers to a structure having at least one region or characteristic dimension with a dimension of less than about 1000 nm, e.g., less than about 300 nm, less than about 200 nm, less than about 100 nm, or less than about 50 nm. Typically, the region or characteristic dimension will be along the smallest axis of the structure. Examples of such structures include nanowires, nanorods, nanotubes, branched nanocrystals, nanotetrapods, tripods, bipods, nanocrystals, nanodots, quantum dots, nanoparticles, branched tetrapods (e.g., inorganic dendrimers), and the like. Nanostructures can be substantially homogeneous in material properties, or in certain embodiments can be heterogeneous (e.g. heterostructures). Nanostructures can be, e.g., substantially crystalline, substantially monocrystalline, polycrystalline, amorphous, or a combination thereof. In one aspect, each of the three dimensions of the nanostructure has a dimension of less than about 1000 nm, e.g., or even less than about 300 nm, less than about 200 nm, less than about 100 nm, or less than about 50 nm. Nanostructures can comprise one or more surface ligands (e.g., surfactants).

The terms "crystalline" or "substantially crystalline", when used with respect to nanostructures, refer to the fact that the nanostructures typically exhibit long-range ordering across one or more dimensions of the structure. It will be understood by one of skill in the art that the term "long range ordering" will depend on the absolute size of the specific nanostructures, as ordering for a single crystal cannot extend beyond the boundaries of the crystal. In this case, "long-range ordering" will mean substantial order across at least the majority of the dimension of the nanostructure. In some instances, a nanostructure can bear an oxide or other coating, or can be comprised of a core and at least one shell. In such instances it will be appreciated that the oxide, shell(s), or other coating need not exhibit such ordering (e.g. it can be amorphous, polycrystalline, or otherwise). In such instances, the phrase "crystalline," "substantially crystalline," "substantially monocrystalline," or "monocrystalline" refers to the central core of the nanostructure (excluding the coating layers or shells). The terms "crystalline" or "substantially crystalline" as used herein are intended to also encompass structures comprising various defects, stacking faults, atomic substitutions, and the like, as long as the structure exhibits substantial long range ordering (e.g., order over at least about 80% of the length of at least one axis of the nanostructure or its core). In addition, it will be appreciated that the interface between a core and the outside of a nanostructure or between a core and an adjacent shell or between a shell and a second adjacent shell may contain non-crystalline regions and may even be amorphous. This does not prevent the nanostructure from being crystalline or substantially crystalline as defined herein. The term "monocrystalline" when used with respect to a nanostructure indicates that the nanostructure is substantially crystalline and comprises substantially a single crystal. When used with respect to a nanostructure heterostructure comprising a core and one or more shells, "monocrystalline" indicates that the core is substantially crystalline and comprises substantially a single crystal. When not used with respect to a nanostructure, the term "monocrystalline" to materials that are composed of substantially a single crystallite of substantially the same size and orientation.

"Nanocrystal" is a nanostructure that is substantially monocrystalline. A nanocrystal thus has at least one region or characteristic dimension with a dimension of less than about 1000 nm, e.g., less than about 300 nm less than about 200 nm, less than about 100 nm, or less than about 50 nm. Typically, the region or characteristic dimension will be along the smallest axis of the structure. Examples of such structures include nanowires, nanorods, nanotubes, branched nanowires, nanotetrapods, nanotripods, nanobipods, nanocrystals, nanodots, quantum dots, nanoparticles, nanoribbons, and the like. Nanostructures can be substantially homogeneous in material properties, or in certain embodiments can be heterogeneous (e.g. heterostructures). Optionally, a nanocrystal can comprise one or more surface ligands (e.g., surfactants). The nanocrystal is optionally substantially single crystal in structure (a "single crystal nanostructure" or a "monocrystalline nanostructure"). While nanostructures for use in the present invention can be fabricated from essentially any convenient material or material, preferably the nanostructure is prepared from an inorganic material, e.g., an inorganic conductive or semiconductive material. A conductive or semiconductive nanostructure often displays 1-dimensional quantum confinement, e.g., an electron can often travel along only one dimension of the structure. Nanocrystals can be substantially homogeneous in material properties, or in certain embodiments can be heterogeneous (e.g. heterostructures). The term "nanocrystal" is intended to encompass substantially monocrystalline nanostructures comprising various defects, stacking faults, atomic substitutions, and the like, as well as substantially monocrystalline nanostructures without such defects, faults, or substitutions. In the case of nanocrystal heterostructures comprising a core and one or more shells, the core of the nanocrystal is typically substantially monocrystalline, but the shell(s) need not be. The nanocrystals can be fabricated from essentially any convenient material or materials.

The term "polycrystalline" refers to materials that are composed of many crystallites of varying size and orientation. When used with respect to nanostructures, the term "polycrystalline" refers to a crystalline nanostructure that is not monocrystalline.

A "biocompatible" material refers to a material that does not typically induce an adverse response when inserted or injected into a subject. The adverse response includes significant inflammation and/or acute rejection of the material by the immune system of the subject, for instance, via a T-cell-mediated response. It is recognized that "biocompatibility" is a relative term and that some degree of immune response is to be expected even for materials that are highly compatible with living tissues of the subject. However, as used herein, "biocompatibility" refers to the acute rejection of a material by at least a portion of the immune system, i.e., a material that lacks biocompatibility (i.e. being non-biocompatible) in a subject provokes an immune response in the subject that is severe enough such that the rejection of the material by the immune system cannot be adequately controlled and often is of a degree such that the material must be removed from the subject in order for the subject to be as well as it was before the non-biocompatible material was introduced into the subject. One test to determine biocompatibility of a material is to expose the material to cells (e.g., fibroblasts or epithelial cells) in vitro; the material is considered biocompatible if it does not result in significant cell death at moderate concentrations, e.g., at concentrations of about 50 micrograms/$10^6$ cells. In certain embodiments, there is no significant cell death if less than about 20% of the cells are dead, even if phagocytosed or otherwise uptaken by the cells. In some embodiments, a material is biocompatible if contacting it with cells in vitro results in less than 20% cell death and if the administration of the material in vivo does not induce unwanted inflammation or other adverse responses. In certain embodiments, a biocompatible material is biodegradable. A non-limiting example of biocompatible materials is biocompatible polymers (including biocompatible copolymers).

A "biodegradable" material refers to a material that is able to degrade chemically and/or biologically (e.g., by hydrolysis or enzymatic activity), within a physiological environment, such as within the body or when introduced to cells. For instance, the material may be one that hydrolyzes spontaneously upon exposure to water (e.g., within a subject) and/or may degrade upon exposure to heat (e.g., at temperatures of about 37° C.). Degradation of a material may occur at varying rates, depending on the material used. For example, the half-life of the material (the time at which 50% of the material is degraded into smaller components) may be on the order of days, weeks, months, or years. The material may be biologically degraded, e.g., by enzymatic activity or cellular machinery, for example, through exposure to a lysozyme. In some embodiments, the material may be broken down into smaller components that cells can either reuse or dispose of without significant toxic effect on the cells (e.g., fewer than about 20% of the cells are killed when the components are added to cells in vitro). Non-limiting examples of biodegradable materials are biodegradable polymers (including biodegradable copolymers). Examples of biodegradable polymers include, but are not limited to, poly(ethylene glycol)-poly(propylene oxide)-poly(ethylene glycol) triblock copolymers, poly(vinyl alcohol) (PVA), poly(lactide) (or poly(lactic acid)), poly(glycolide) (or poly(glycolic acid)), poly(orthoesters), poly(caprolactones), polylysine, poly(ethylene imine), poly(acrylic acid), poly(urethanes), poly(anhydrides), poly(esters), poly(trimethylene carbonate), poly(ethyleneimine), poly(acrylic acid), poly(urethane), poly(beta amino esters), and copolymers thereof (e.g., poly(lactide-co-glycolide) (PLGA)).

As used herein, the terms "pharmaceutical composition" and "formulation" are used interchangeably.

As used herein, the terms "pharmaceutical agent" and "drug" are used interchangeably.

DESCRIPTION OF CERTAIN EMBODIMENTS OF THE INVENTION

The present invention provides crystalline forms of the compound 7-(3-(4-(4-fluoro-2-methyl-1H-indol-5-yloxy)-6-methoxyquinazolin-7-yloxy)propyl)-2-oxa-7-azaspiro[3.5]nonane, referred to herein as Compound 3 and shown below:

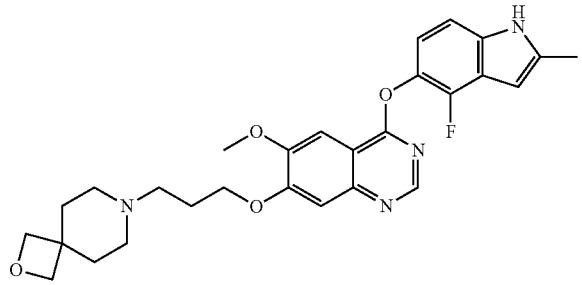 [SMILES: COc1cc2c(Oc3ccc4[nH]c(C)cc4c3F)ncnc2cc1OCCCN1CCC2(CC1)COC2]

(Compound 3)

In particular embodiments, the crystalline form is crystalline Form A, which has an X-Ray Powder Diffraction (XRPD) pattern with peaks at about 6.11, 9.63, 16.41, 18.60, 20.36 and 23.01±0.3 degrees two theta or 14.45, 9.17, 5.40, 4.77, 4.36 and 3.86±0.3 Å in d-spacing. In further embodiments, crystalline Form A further has XRPD peaks at about 11.46, 12.26, 18.16, 19.51, 21.12 and 25.71±0.3 degrees two theta or 7.71, 7.22, 4.88, 4.55, 4.20 and 3.46±0.3 Å in d-spacing. In further embodiments, crystalline Form A further has XRPD peaks at about 11.10, 15.66, 17.54, 22.31, 24.79 and 28.90±0.3 degrees two theta or 7.96, 5.65, 5.05, 3.98, 3.59 and 3.09±0.3 Å in d-spacing. In still further embodiments, crystalline Form A has an XRPD pattern with peaks at about 6.11, 9.63, 11.10, 11.46, 12.26, 15.66, 16.41, 17.54, 18.16, 18.60, 19.51, 20.36, 21.12, 22.31, 23.01, 24.79, 25.71 and 28.90±0.3 degrees two theta or 14.45, 9.17, 7.96, 7.71, 7.22, 5.65, 5.40, 5.05, 4.88, 4.77, 4.55, 4.36, 4.20, 3.98, 3.86, 3.59, 3.46 and 3.09±0.3 Å in d-spacing.

In other particular embodiments, the crystalline form is crystalline Form B, which has an XRPD pattern with peaks at about 7.70, 13.53, 17.27, 18.44, 19.73, 23.10 and 26.07±0.3 degrees two theta or 11.47, 6.54, 5.13, 4.81, 4.50, 3.85 and 3.41±0.3 Å in d-spacing. In further embodiments, crystalline Form B further has XRPD peaks at about 9.87, 12.88, 14.40, 15.45, 21.14 and 26.84±0.3 degrees two theta or 8.96, 6.87, 6.14, 5.73, 4.20 and 3.32±0.3 Å in d-spacing. In further embodiments, crystalline Form B further has XRPD peaks at about 10.69, 16.42, 18.90, 22.56, and 29.12±0.3 degrees two theta or 8.27, 5.39, 4.69, 3.94 and 3.06±0.3 Å in d-spacing. In still further embodiments, crystalline Form B has an XRPD pattern with peaks at about 7.70, 9.87, 10.69, 12.88, 13.53, 14.40, 15.45, 16.42, 17.27, 18.44, 18.90, 19.73, 21.14, 22.56, 23.10, 26.07, 26.84 and 29.12±0.3 degrees two theta or 11.47, 8.96, 8.27, 6.87, 6.54, 6.14, 5.73, 5.39, 5.13, 4.81, 4.69, 4.50, 4.20, 3.94, 3.85, 3.41, 3.32 and 3.06±0.3 Å in d-spacing.

In one aspect, the present invention relates to a compound having the formula

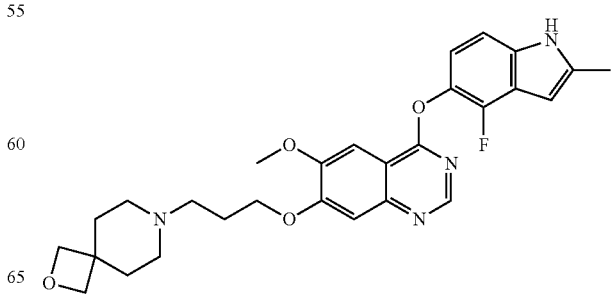

in crystalline Form A.

In another aspect, the present invention relates to a crystalline form of a compound having the formula

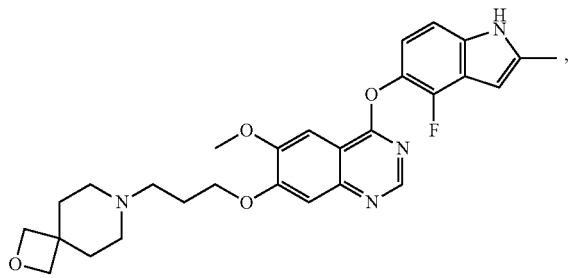 [SMILES: COc1cc2c(Oc3ccc4[nH]c(C)cc4c3F)ncnc2cc1OCCCN1CCC2(CC1)COC2]

wherein said crystalline form is crystalline Form A having an X-ray powder diffraction (XRPD) pattern with peaks at about 6.11, 9.63, 16.41, 18.60, 20.36 and 23.01±0.3 degrees two theta, or 14.45, 9.17, 5.40, 4.77, 4.36 and 3.86±0.3 Å in d-spacing.

In another embodiment, the present invention relates to a compound having the formula

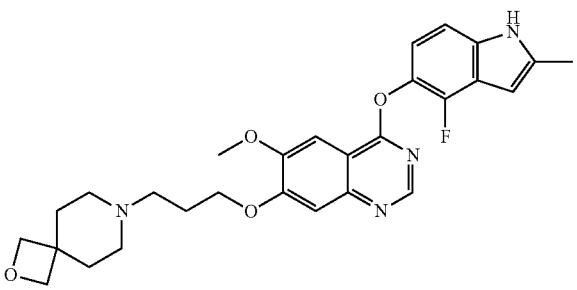 [SMILES: COc1cc2c(Oc3ccc4[nH]c(C)cc4c3F)ncnc2cc1OCCCN1CCC2(CC1)COC2]

in crystalline Form B.

In another embodiment, the present invention relates to a crystalline form of a compound having the formula

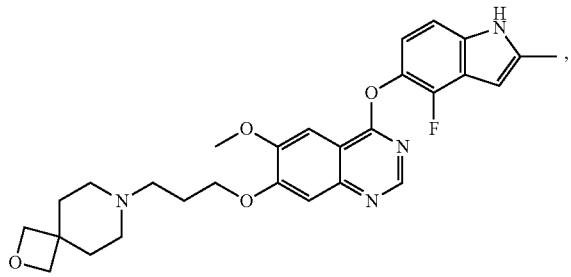 [SMILES: COc1cc2c(Oc3ccc4[nH]c(C)cc4c3F)ncnc2cc1OCCCN1CCC2(CC1)COC2]

wherein said crystalline form is crystalline Form B having an X-Ray Powder Diffraction (XRPD) pattern with peaks at about 7.70, 13.53, 17.27, 18.44, 19.73, 23.10 and 26.07±0.3 degrees two theta or 11.47, 6.54, 5.13, 4.81, 4.50, 3.85 and 3.41±0.3 Å in d-spacing.

The present invention also relates to a process for preparing a crystalline form of Compound 3. In certain embodiments, the present invention relates to a method for preparing crystalline Form A of Compound 3. In additional embodiments, the method of preparing crystalline Form A comprises wet-milling a slurry comprising an amorphous form of Compound 3 and a non-ionic surfactant to obtain nanoparticles of the compound. In further embodiments, the resulting nanoparticles of crystalline Form A have an XRPD pattern with peaks at about 6.11, 9.63, 16.41, 18.60, 20.36 and 23.01±0.3 degrees two theta or 14.45, 9.17, 5.40, 4.77, 4.36 and 3.86±0.3 Å in d-spacing. In still further embodiments, the resulting nanoparticles of crystalline Form A further have an XRPD pattern with peaks at about 11.46, 12.26, 18.16, 19.51, 21.12 and 25.71±0.3 degrees two theta or 7.71, 7.22, 4.88, 4.55, 4.20 and 3.46±0.3 Å in d-spacing, or at about 11.10, 15.66, 17.54, 22.31, 24.79 and 28.9±0.3 degrees two theta or 7.96, 5.65, 5.05, 3.98, 3.59 and 3.09±0.3 Å in d-spacing, or both. In additional embodiments, the resulting nanoparticles of crystalline Form A have an XRPD pattern with peaks at about 6.11, 9.63, 11.10, 11.46, 12.26, 15.66, 16.41, 17.54, 18.16, 18.60, 19.51, 20.36, 21.12, 22.31, 23.01, 24.79, 25.71 and 28.9±0.3 degrees two theta or 14.45, 9.17, 7.96, 7.71, 7.22, 5.65, 5.40, 5.05, 4.88, 4.77, 4.55, 4.36, 4.20, 3.98, 3.86, 3.59, 3.46 and 3.09±0.3 Å in d-spacing.

In other embodiments, the present invention relates to a method for preparing crystalline Form B of Compound 3. In certain embodiments, the method of preparing crystalline Form B comprises of crystallizing the amorphous form of Compound 3 from a solvent mixture comprising water and acetone. In particular embodiments, the method of preparing crystalline Form B utilizes a solvent mixture consisting of a 4:1 acetone:water mixture. In other embodiments, the method of preparing crystalline Form B further comprises heating the solvent mixture to dissolve the compound and/or cooling the solvent mixture to allow crystal formation. In some embodiments, the resulting crystalline Form B has an XRPD pattern with peaks at about 7.7, 13.53, 17.27, 18.44, 19.73, 23.1 and 26.07±0.3 degrees two theta or 11.47, 6.54, 5.13, 4.81, 4.5, 3.85 and 3.41±0.3 Å in d-spacing. In additional embodiments, the resulting crystalline Form B further have an XRPD pattern with peaks at about 9.87, 12.88, 14.4, 15.45, 21.14 and 26.84±0.3 degrees two theta or 8.96, 6.87, 6.14, 5.73, 4.2 and 3.32±0.3 Å in d-spacing, or at about 10.69, 16.42, 18.9, 22.56 and 29.12±0.3 degrees two theta or 8.27, 5.39, 4.69, 3.94 and 3.06±0.3 Å in d-spacing, or both. In additional embodiments, the resulting crystalline Form B have an XRPD pattern with peaks at about 7.7, 9.87, 10.69, 12.88, 13.53, 14.4, 15.45, 16.42, 17.27, 18.44, 18.9, 19.73, 21.14, 22.56, 23.1, 26.07, 26.84 and 29.12±0.3 degrees two theta or 11.47, 8.96, 8.27, 6.87, 6.54, 6.14, 5.73, 5.39, 5.13, 4.81, 4.69, 4.5, 4.2, 3.94, 3.85, 3.41, 3.32 and 3.06±0.3 Å in d-spacing.

Also provided are methods of using the crystalline forms of Compound 3 to treat diseases, including proliferative diseases, ocular diseases, dermatological diseases, inflammatory diseases, autoimmune diseases, auto-inflammatory diseases, and metabolic diseases. The present invention further provides methods of using crystalline Form A or crystalline Form B of Compound 3 as therapeutics, e.g., in the treatment and/or prevention of diseases associated with abnormal angiogenesis and/or aberrant signaling of a growth factor activity (e.g., vascular endothelial growth factor (VEGF) or angiogenesis. In certain embodiments, the disease being treated and/or prevented using crystalline Form A or crystalline Form B of Compound 3, pharmaceutical compositions, kits, uses, and methods include proliferative diseases (e.g., cancers, benign neoplasms, diseases associated with angiogenesis, inflammatory diseases, autoimmune diseases) and ocular diseases (e.g., macular degeneration, glaucoma, diabetic retinopathy, retinoblastoma, edema, macular edema, corneal neovascularization, uveitis, dry eye, blepharitis, and post-surgical inflammation).

In certain embodiments, the crystalline forms of the invention are monocrystalline. In certain embodiments, the compounds of the invention are polycrystalline.

The crystalline forms of the invention may also have a relatively low aqueous solubility (i.e., a solubility in water, optionally with one or more buffers). For example, the crystalline forms of Compound 3 may have an aqueous solubility of less than about or equal to about 3 mg/mL, less than about 1 mg/mL, less than about 0.3 mg/mL, less than about 0.1 mg/mL, less than about 0.03 mg/mL, less than about 0.01 mg/mL, less than about 1 µg/mL, less than about 0.1 µg/mL, less than about 0.01 µg/mL, less than about 1 ng/mL, less than about 0.1 ng/mL, or less than about 0.01 ng/mL at 25° C. In some embodiments, the crystalline forms of Compound 3 have an aqueous solubility of at least about 1 µg/mL, at least about 10 µg/mL, at least about 0.1 ng/mL, at least about 1 ng/mL, at least about 10 ng/mL, at least about 0.1 µg/mL, at least about 1 µg/mL, at least about 3 µg/mL, at least about 0.01 mg/mL, at least about 0.03 mg/mL, at least about 0.1 mg/mL, at least about 0.3 mg/mL, at least about 1.0 mg/mL, or at least about 3 mg/mL at 25° C. Combinations of the above-noted ranges are possible (e.g., an aqueous solubility of at least about 10 µg/mL and less than about 1 mg/mL). Other ranges are also possible. The crystalline forms of Compound 3 may have these or other ranges of aqueous solubilities at any point throughout the pH range (e.g., at about pH 7 or from pH 1 to pH 14).

The crystalline forms of Compound 3 may be suitable for being processed into mucus-penetrating pharmaceutical compositions (e.g., particles or crystals). In certain embodiments, the crystalline forms of Compound 3 are suitable for milling (e.g., nano-milling). In certain embodiments, the crystalline forms of Compound 3 are suitable for precipitation (e.g., microprecipitation, nanoprecipitation, crystallization, or controlled crystallization). In certain embodiments, the crystalline forms of Compound 3 are suitable for emulsification. In certain embodiments, the crystalline forms of Compound 3 are suitable for freeze-drying.

Compound 3 can be prepared using any suitable method. In certain embodiments, Compound 3 can be prepared using Method A as shown in Scheme 1:

Scheme 1: Method A of synthesizing Compound 3.

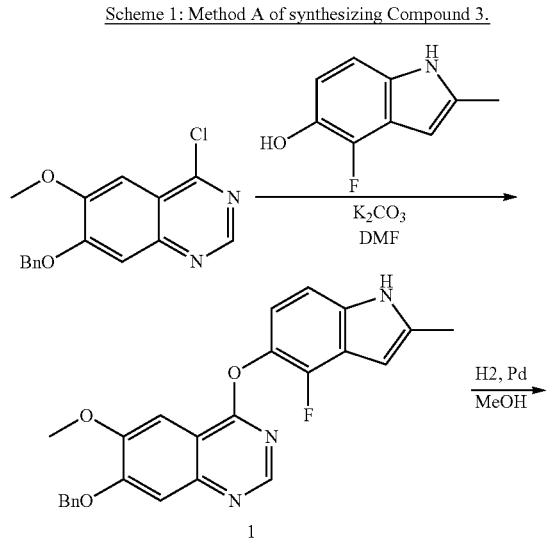

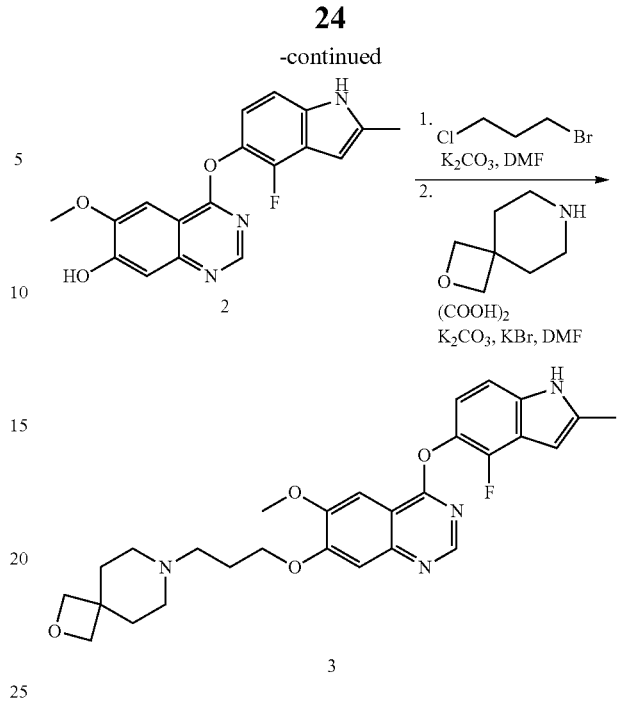

In certain embodiments, Compound 3 can also be prepared using Method B as shown in Scheme 2:

Scheme 2: Method B of synthesizing Compound 3.

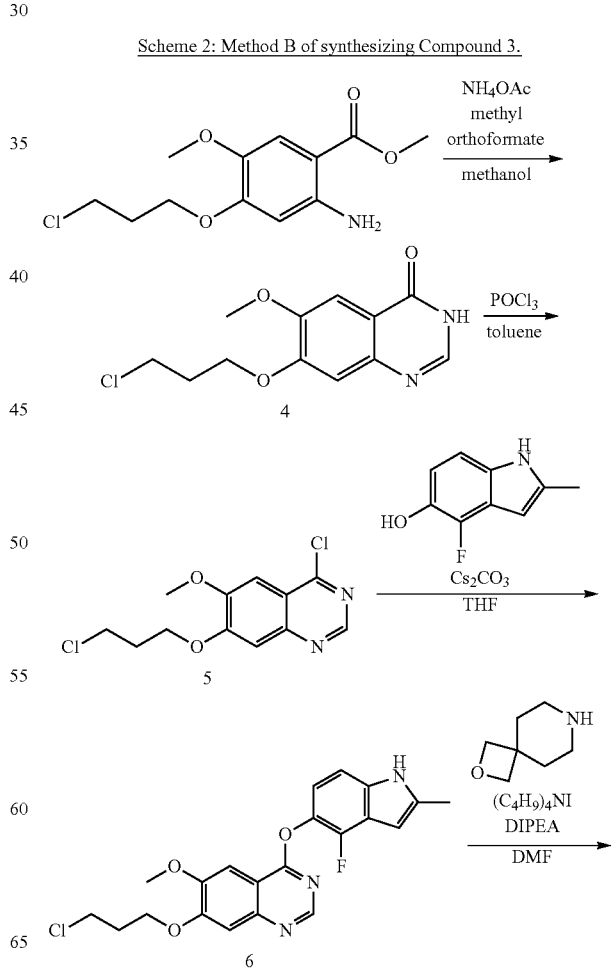

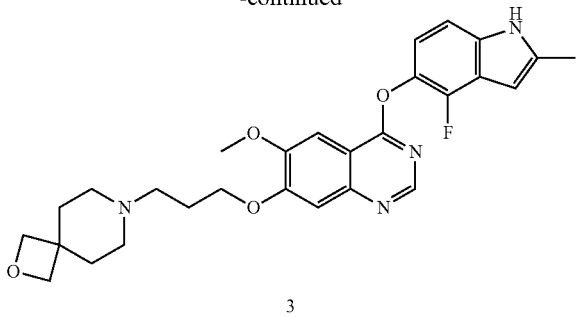

3

Pharmaceutical Compositions, Kits, and Methods of Uses and Administration

The present invention provides pharmaceutical compositions comprising crystalline Form A of Compound 3, and optionally a pharmaceutically acceptable excipient, or crystalline Form B of Compound 3, and optionally a pharmaceutically acceptable excipient. In certain embodiments, a compound described herein is provided in an effective amount in the pharmaceutical composition. In certain embodiments, the effective amount is a therapeutically effective amount. In certain embodiments, the effective amount is a prophylactically effective amount. In certain embodiments, the effective amount is an amount effective for treating and/or preventing a disease. In certain embodiments, the effective amount is an amount effective for treating a disease. In certain embodiments, the effective amount is an amount effective for treating and/or preventing a disease associated with aberrant signaling of a growth factor. In certain embodiments, the effective amount is an amount effective for treating a disease associated with aberrant signaling of a growth factor. In certain embodiments, the effective amount is an amount effective for treating and/or preventing a disease associated with aberrant signaling of vascular endothelial growth factor (VEGF). In certain embodiments, the effective amount is an amount effective to treat and/or prevent a disease associated with abnormal angiogenesis, such as cancer, benign neoplasm, atherosclerosis, hypertension, inflammatory disease, rheumatoid arthritis, macular degeneration, choroidal neovascularization, retinal neovascularization, and diabetic retinopathy. In certain embodiments, the effective amount is an amount effective to treat cancer (e.g., an ocular cancer). In certain embodiments, the effective amount is an amount effective to treat macular degeneration.

An effective amount of Compound 3 crystalline form of the invention may vary from about 0.001 mg/kg to about 1000 mg/kg in one or more dose administrations for one or several days (depending on the mode of administration). In certain embodiments, the effective amount per dose varies from about 0.001 mg/kg to about 1000 mg/kg, from about 0.01 mg/kg to about 750 mg/kg, from about 0.1 mg/kg to about 500 mg/kg, from about 1.0 mg/kg to about 250 mg/kg, and from about 10.0 mg/kg to about 150 mg/kg.

An effective amount of Compound 3 crystalline form of the invention may inhibit abnormal angiogenesis and/or aberrant signaling of a growth factor by at least about 10%, at least about 20%, at least about 30%, at least about 40%, at least about 50%, at least about 60%, at least about 70%, at least about 80%, or at least about 90%. An effective amount of a Compound 3 of the invention may inhibit abnormal angiogenesis and/or aberrant signaling of a growth factor by less than about 90%, less than about 80%, less than about 70%, less than about 60%, less than about 50%, less than about 40%, less than about 30%, less than about 20%, or less than about 10%. Combinations of the ranges described herein (e.g., at least 20% and less than 50%) are also within the scope of the invention. In certain embodiments, an effective amount of a Compound 3 of the invention inhibits abnormal angiogenesis and/or aberrant signaling of a growth factor by a percentage or a range of percentage described herein, compared to normal angiogenesis and/or signaling.

Pharmaceutical compositions described herein can be prepared by any method known in the art of pharmacology. In general, such preparatory methods include the steps of bringing a crystalline form of Compound 3 described herein (i.e., the "active ingredient") into association with a carrier or excipient, and/or one or more other accessory ingredients, and then, if necessary and/or desirable, shaping, and/or packaging the product into a desired single- or multi-dose unit.

Pharmaceutical compositions can be prepared, packaged, and/or sold in bulk, as a single unit dose, and/or as a plurality of single unit doses. As used herein, a "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition of the invention will vary, depending upon the identity, size, and/or condition of the subject treated and further depending upon the route by which the composition is to be administered. The composition may comprise between 0.001% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite (aluminum silicate) and Veegum (magnesium aluminum silicate)), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate (TWEEN® 20), polyoxyethylene sorbitan (TWEEN® 60), polyoxyethylene sorbitan monooleate (TWEEN® 80), sorbitan monopalmitate (SPAN® 40), sorbitan monostearate (SPAN® 60), sorbitan tristearate (SPAN® 65), glyceryl monooleate, sorbitan monooleate (SPAN® 80), polyoxyethylene esters (e.g., polyoxyethylene monostearate (MYRJ® 45), polyoxyethylene hydrogenated castor oil, polyethoxylated castor oil, polyoxymethylene stearate, and SOLUTOL®), sucrose fatty acid esters, polyethylene glycol fatty acid esters (e.g., CREMOPHOR®), polyoxyethylene ethers, (e.g., polyoxyethylene lauryl ether (BRIJ® 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, PLURONIC® F-68, Poloxamer P-188, cetrimonium bromide, cetylpyridinium chloride, benzalkonium chloride, docusate sodium, and/or mixtures thereof.

Exemplary binding agents include starch (e.g., cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (VEEGUM®), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, antiprotozoan preservatives, alcohol preservatives, acidic preservatives, and other preservatives. In certain embodiments, the preservative is an antioxidant. In other embodiments, the preservative is a chelating agent.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, GLYDANT® Plus, PHENONIP®, methylparaben, GERMALL® 115, GERMABEN® II, NEOLONE®, KATHON®, and EUXYL®.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, chamomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates of the invention are mixed with solubilizing agents such as CREMOPHOR®, alcohols, oils, modified oils, glycols, polysorbates, cyclodextrins, polymers, and mixtures thereof.

A pharmaceutical composition of the invention can be formulated for administration by injection in any acceptable form, including intravenous, intraperitoneal, intramuscular, subcutaneous, parenteral, epidural, or intraocular. Injectable preparations, for example, sterile injectable aqueous or oleaginous suspensions can be formulated according to the known art using suitable dispersing or wetting agents and suspending agents. The sterile injectable preparation can be a sterile injectable solution, suspension, or emulsion in a nontoxic parenterally acceptable diluent or solvent, for example, as a solution in 1,3-butanediol. Among the acceptable vehicles and solvents that can be employed are water, Ringer's solution, U.S.P., and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use. The formulation can also be prepared under aseptic conditions or sterilized with heat or irradiation.

An injectable formulation or pharmaceutical composition of the invention can also be formulated for ophthalmic administration by injection in any acceptable form, including intravitreal, perocular, intrastromal, intracameral, subretinal, conjunctival, subconjunctival, sub-tenon (e.g., anterior or posterior), circumcorneal, scleral, episcleral, posterior juxtascleral, peri-bulbar, retro-bulbar, suprachoroidal, and tear duct. A pharmaceutical composition of the invention may also be formulated for ophthalmic administration by implant or the use of reservoirs (e.g., biodegradable delivery system, non-biodegradable delivery system and other implanted extended or slow release device or formulation).

Compositions for rectal or vaginal administration are typically suppositories which can be prepared by formulating a Compound 3 crystalline form of this invention with suitable non-irritating excipients or carriers such as cocoa butter, polyethylene glycol, or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may include a buffering agent.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the art of pharmacology. They may optionally comprise opacifying agents and can be of a composition that they release the active ingredient(s) only, or preferentially, in a certain part of the intestinal tract, optionally, in a delayed manner. Examples of encapsulating compositions which can be used include polymeric substances and waxes. Solid compositions of a similar type can be employed as fillers in soft and hard-filled gelatin capsules using such excipients as lactose or milk sugar as well as high molecular weight polyethylene glycols and the like.

The active ingredient can be in a micro-encapsulated form with one or more excipients as noted above. The solid dosage forms of tablets, dragees, capsules, pills, and granules can be prepared with coatings and shells such as enteric coatings, release controlling coatings, and other coatings well known in the pharmaceutical formulating art. In such solid dosage forms the active ingredient can be admixed with at least one inert diluent such as sucrose, lactose, or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of encapsulating agents which can be used include polymeric substances and waxes.

Dosage forms for topical and/or transdermal administration of a compound of this invention may include ointments, pastes, creams, lotions, gels, powders, solutions, suspensions, sprays, inhalants, and/or patches. Generally, the active ingredient is admixed under sterile conditions with a pharmaceutically acceptable carrier or excipient and/or any needed preservatives and/or buffers as can be required. Additionally, the present invention contemplates the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Suitable devices for use in delivering intradermal pharmaceutical compositions described herein include short needle devices such as those described in U.S. Pat. Nos. 4,886,499; 5,190,521; 5,328,483; 5,527,288; 4,270,537; 5,015,235; 5,141,496; and 5,417,662. Intradermal compositions can be administered by devices which limit the effective penetration length of a needle into the skin, such as those described in PCT publication WO 99/34850 and functional equivalents thereof. Alternatively or additionally, conventional syringes can be used in the classical mantoux method of intradermal administration. Jet injection devices which deliver liquid vaccines to the dermis via a liquid jet injector and/or via a needle which pierces the stratum corneum and produces a jet which reaches the dermis are suitable. Jet injection devices are described, for example, in U.S. Pat. Nos. 5,480,381; 5,599,302; 5,334,144; 5,993,412; 5,649,912; 5,569,189; 5,704,911; 5,383,851; 5,893,397; 5,466,220; 5,339,163; 5,312,335; 5,503,627; 5,064,413; 5,520,639; 4,596,556; 4,790,824; 4,941,880; 4,940,460; and PCT publications WO 97/37705 and WO 97/13537. Ballistic powder/particle delivery devices which use compressed gas to accelerate the compound in powder form through the outer layers of the skin to the dermis are suitable.

Formulations suitable for topical administration (including ocular or dermal) include, but are not limited to, liquid and/or semi-liquid preparations such as liniments, lotions, oil-in-water and/or water-in-oil emulsions such as creams, ointments, and/or pastes, and/or solutions and/or suspensions. Topically administrable formulations may, for example, comprise from about 0.001% to about 50% (w/w) active ingredient, although the concentration of the active ingredient can be as high as the solubility limit of the active ingredient in the solvent. Formulations for topical administration may further comprise one or more of the additional ingredients described herein. In one aspect, the present invention relates to formulations or pharmaceutical compositions suitable for topical administration comprising crystalline Form A of Compound 3 or crystalline Form B of Compound 3.

A pharmaceutical composition of the invention can be prepared, packaged, and/or sold in a formulation suitable for pulmonary administration. Such a formulation may comprise dry particles which comprise the active ingredient and which have a diameter in the range from about 0.5 to about 7 microns, or from about 1 to about 6 microns. Such compositions are conveniently in the form of dry powders for administration using a device comprising a dry powder reservoir to which a stream of propellant can be directed to disperse the powder and/or using a self-propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 20 microns. Alternatively, at least 95% of the particles by weight have a diameter greater than 1 nanometer and at least 90% of the particles by number have a diameter less than 15 microns. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.001 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions of the invention formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.01 to about 200 microns. Alternately, formulations for pulmonary administration may comprise a powder and/or an aerosolized and/or atomized solution and/or suspension comprising the active ingredient. Such powdered, aerosolized, and/or atomized formulations, when dispersed, may have an average particle and/or droplet size in the range from about 0.01 to about 200 microns, and may further comprise one or more of the additional ingredients described herein.

Formulations described herein as being useful for pulmonary delivery are useful for intranasal delivery of a pharmaceutical composition of the invention. Another formulation suitable for intranasal administration is a coarse powder comprising the active ingredient and having an average particle from about 0.2 to 500 micrometers. Such a formulation is administered by rapid inhalation through the nasal passage from a container of the powder held close to the nares. Formulations for nasal administration may, for example, comprise from about as little as 0.001% (w/w) to as much as 100% (w/w) of the active ingredient, and may comprise one or more of the additional ingredients described herein.

A pharmaceutical composition of the invention can be prepared, packaged, and/or sold in a formulation for oral administration. Such formulations may, for example, be in the form of tablets and/or lozenges made using conventional methods, and may contain, for example, 0.1 to 20% (w/w) active ingredient, the balance comprising an orally dissolvable and/or degradable composition and, optionally, one or more of the additional ingredients described herein.

Formulations described herein may also be delivered via buccal administration. Such formulations may, for example, be in the form of tablets and/or lozenges made using conventional methods, and may contain, for example, 0.001 to 50% (w/w) active ingredient, the balance comprising an orally dissolvable and/or degradable composition and, optionally, one or more of the additional ingredients described herein.

A pharmaceutical composition of the invention can be prepared, packaged, and/or sold in a formulation for ophthalmic administration. Such formulations may, for example, be in the form of eye drops including, for example, a 0.001/10.0% (w/w) solution and/or suspension of the active ingredient in an aqueous or oily liquid carrier or excipient. Such drops may further comprise buffering agents, salts, and/or one or more other of the additional ingredients described herein. Other ophthalmically-administrable formulations which are useful include those which comprise the active ingredient in microcrystalline form and/or in a liposomal preparation.

A pharmaceutical composition of the invention may also be formulated for administration by the ophthalmic mucous membrane route, such as, for example, eye drops, ointments, or gels. These formulations may be prepared by conventional means, and, if desired, the subject compositions may be mixed with any conventional additive, such as a buffering or pH-adjusting agent, tonicity adjusting agents, viscosity modifiers, suspension stabilizers, preservatives, and other pharmaceutical excipients. In addition, in certain embodiments, subject compositions described herein may be lyophilized or subjected to another appropriate drying technique such as spray drying. Ear drops are also contemplated as being within the scope of this invention.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

Compositions provided herein are typically formulated in dosage unit form for ease of administration and uniformity of dosage. It will be understood, however, that the total daily usage of the compositions of the present invention will be decided by the attending physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex, and diet of the subject; the time of administration, route of administration, and rate of excretion of the specific active ingredient employed; the duration of the treatment; drugs used in combination or coincidental with the specific active ingredient employed; and like factors well known in the medical arts.

The compositions provided herein can be administered by any route, including enteral (e.g., oral), parenteral, injection, intraocular, intravenous, intramuscular, intra-arterial, intramedullary, intrathecal, subcutaneous, intraventricular, transdermal, interdermal, rectal, intravaginal, intraperitoneal, topical (including dermal or ocular, such as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, injections, including intravenous administration (e.g., systemic intravenous injection) and intraocular administration, regional administration via blood and/or lymph supply, and/or direct administration to an affected site including topical administration (e.g., dermal and/or ocular). In general, the most appropriate route of administration will depend upon a variety of factors including the nature of the agent (e.g., its stability in the environment of the gastrointestinal tract), and/or the condition of the subject (e.g., whether the subject is able to tolerate oral administration). In certain embodiments, the compound or pharmaceutical composition of the invention is suitable for administration to the eye of a subject. In another embodiment, the compound or pharmaceutical composition of a crystalline form of Compound 3 is suitable for topical administration to the eye of a subject.

The exact amount of a crystalline form of Compound 3 of the invention required to achieve an effective amount will vary from subject to subject, depending, for example, on species, age, and general condition of a subject, severity of the side effects or disorder, mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations).

In certain embodiments, an effective amount of a Compound 3 crystalline form of the invention for administration one or more times a day to a 70 kg adult human may comprise about 0.0001 mg to about 3000 mg, about 0.0001 mg to about 2000 mg, about 0.0001 mg to about 1000 mg, about 0.001 mg to about 1000 mg, about 0.01 mg to about 1000 mg, about 0.1 mg to about 1000 mg, about 1 mg to about 1000 mg, about 1 mg to about 100 mg, about 10 mg to about 1000 mg, about 10 mg to about 100 mg, or about 100 mg to about 1000 mg, of Compound 3 per unit dosage form.

In certain embodiments, the Compound 3 crystalline forms described herein may be at dosage levels sufficient to deliver from about 0.001 mg/kg to about 1000 mg/kg, from about 0.01 mg/kg to about 500 mg/kg, preferably from about 0.1 mg/kg to about 400 mg/kg, preferably from about 0.5 mg/kg to about 300 mg/kg, from about 0.01 mg/kg to about 100 mg/kg, from about 0.1 mg/kg to about 10 mg/kg, and more preferably from about 1 mg/kg to about 25 mg/kg, of subject body weight per day, one or more times a day, to obtain the desired therapeutic and/or prophylactic effect.

It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

It will be also appreciated that a crystalline form of Compound 3 or composition thereof, as described herein, can be administered in combination with one or more additional pharmaceutical agents (e.g., therapeutically and/or prophylactically active agents). The crystalline forms of Compound 3 or compositions can be administered in combination with additional pharmaceutical agents that improve their activity (e.g., activity in preventing and/or treating a disease associated with aberrant signaling of a growth factor (e.g., VEGF) or with abnormal angiogenesis in a subject, in inhibiting aberrant signaling of a growth factor (e.g., VEGF) in a subject or cell, or in inhibiting abnormal angiogenesis in a subject), bioavailability, reduce and/or modify their metabolism, inhibit their excretion, and/or modify their distribution within the body of a subject. It will also be appreciated that the therapy employed may achieve a desired effect for the same disorder, and/or it may achieve different effects.

The crystalline form of Compound 3 or composition of the invention can be administered concurrently with, prior to, or subsequent to one or more additional pharmaceutical agents, which may be useful as, e.g., combination therapies. Pharmaceutical agents include therapeutically active agents.

Pharmaceutical agents also include prophylactically active agents. Pharmaceutical agents include small organic molecules such as drug compounds (e.g., compounds approved for human or veterinary use by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells. In certain embodiments, the additional pharmaceutical agent is a pharmaceutical agent useful for treating and/or preventing a disease described herein. Each additional pharmaceutical agent may be administered at a dose and/or on a time schedule determined for that pharmaceutical agent. The additional pharmaceutical agents may also be administered together with each other and/or with the compound or composition described herein in a single dose or administered separately in different doses. The particular combination to employ in a regimen will take into account compatibility of the inventive compound with the additional pharmaceutical agent(s) and/or the desired therapeutic and/or prophylactic effect to be achieved. In general, it is expected that the additional pharmaceutical agent(s) utilized in combination be utilized at levels that do not exceed the levels at which they are utilized individually. In some embodiments, the levels utilized in combination will be lower than those utilized individually.

The additional pharmaceutical agents include, but are not limited to, anti-proliferative agents (e.g., anti-cancer agents), anti-angiogenesis agents, anti-inflammatory agents, immunosuppressants, anti-bacterial agents, anti-viral agents, antidiabetic agents, anti-allergic agents, and pain-relieving agents. In certain embodiments, the additional pharmaceutical agent is a growth factor inhibitor. In certain embodiments, the additional pharmaceutical agent is a VEGF inhibitor. In certain embodiments, the additional pharmaceutical agent is an angiogenesis inhibitor. In certain embodiments, the additional pharmaceutical agent is an endogenous angiogenesis inhibitor (e.g., vascular endothelial growth factor receptor 1 (VEGFR-1, e.g., pazopanib (VOTRIENT®), cediranib (RECENTIN®), tivozanib (AV-951), axitinib (INLYTA®), semaxanib), HER2 (lapatinib (TYKERB®, TYVERB®), linifanib (ABT-869), MGCD-265, and KRN-633), VEGFR-2 (e.g., regorafenib (BAY 73-4506), telatinib (BAY 57-9352), vatalanib (PTK787, PTK/ZK), MGCD-265, OSI-930, and KRN-633), NRP-1, angiopoietin 2, TSP-1, TSP-2, angiostatin, endostatin, vasostatin, calreticulin, platelet factor-4, TIMP, CDAI, Meth-1, Meth-2, IFN-α, IFN-β, IFN-γ, CXCL10, IL-4, IL-12, IL-18, prothrombin (kringle domain-2), antithrombin III fragment, prolactin, VEGI, SPARC, osteopontin, maspin, canstatin, a proliferin-related protein, sorafenib (NEXAVAR®), and restin). In certain embodiments, the additional pharmaceutical agent is an exogenous angiogenesis inhibitor (e.g., bevacizumab, itraconazole, carboxyamidotriazole, TNP-470, CM101, IFN-α, IL-12, platelet factor-4, suramin, SU5416, thrombospondin, a VEGFR antagonist, an angiostatic steroid, an angiostatic steroid+heparin, a cartilage-derived angiogenesis inhibitory factor, a matrix metalloproteinase inhibitor, angiostatin, endostatin, 2-methoxyestradiol, tecogalan, tetrathiomolybdate, thalidomide, thrombospondin, prolactin, a $\alpha_v\beta_3$ inhibitor, linomide, and tasquinimod). In certain embodiments, the additional pharmaceutical agent is a corticosteroid, a receptor tyrosine kinase (RTK) inhibitor, a cyclooxygenase (COX) inhibitor, a prostaglandin analog, a non-steroidal anti-inflammatory drug (NSAID), a beta blocker, or a carbonic anhydrase inhibitor. In certain embodiments, the additional pharmaceutical agent is a pharmaceutical agent useful for treating and/or preventing AMD, such as verteporfin (e.g., CHLORIN®, VISUDYNE®), thalidomide (e.g., AMBIODRY®, SYNOVIR®, THALOMID®), talaporfin sodium (e.g., APTOCINE®, LASERPHYRIN®, LITX®), ranibizumab (e.g., LUCENTIS®), pegaptanib octasodium (e.g., MACUGEN®, MACUVERSE®), isopropyl unoprostone (e.g., OCUSEVA®, RESCULA®), interferon beta (e.g., FERON®), fluocinolone acetonide (e.g., ENVISION TD®, RETISERT®), everolimus (e.g., AFINITOR®, CERTICAN®, VOTUBIA®, ZORTRESS®), eculizumab (e.g., SOLARIS®, SOLIRIS®), dexamethasone (e.g., OSURDEX®, OZURDEX®, POSURDEX®, SURODEX®), canakinumab (e.g., ILARIS®), bromfenac (BROMDAY®), ophthalmic (e.g., BRONAC®, BRONUCK®, XIBROM®, YELLOX®), brimonidine (e.g., ALPHAGAN®, BROMOXIDINE®, ENIDIN®), anecortave acetate (e.g., RETAANE®, EDEX®, PROSTAVASIN®, RIGIDUR®, VASOPROST®, VIRIDAL®), aflibercept ophthalmic solution (e.g., EYELEA®, EYLEA®, VEGF-TRAP-EYE®), ocriplasmin (e.g., ILUVIEN®, MEDIDUR®, MEDIDUR FA®), sirolimus (e.g., PERCEIVA®), NT-501, KH-902, fosbretabulin tromethamine (e.g., ZYBRESTAT®), AL-8309, aganirsen (e.g., NORVESS®), volociximab (e.g., OPTHOTEC®), triamcinolone (e.g., Icon Bioscience), TRC-105, Burixafor (e.g., TG-0054), TB-403 (e.g., R-7334), squalamine (e.g., EVIZON®), SB-623, S-646240, RTP-801i-14 (e.g., PF-4523655), RG-7417 (e.g., FCFD-4515S), AL-78898A (e.g., POT-4), PG-11047 (e.g., CGC-11047), pazopanib hydrochloride, sonepcizumab (e.g., ASONEP®, SPHINGOMAB®), padeliporfin (e.g., STAKEL®), OT-551, ontecizumab, NOX-A12, hCNS-SC, Neu-2000, NAFB001, MA09-hRPE, LFG-316, iCo-007 (e.g., ISIS-13650), hl-con1, GSK-933776A, GS-6624 (e.g., AB-0024), ESBA-1008, epitalon, E-10030 (e.g., ARC-127), dalantercept, MP-0112, CNTO-2476, CERE-120, AAV-NTN, CCX-168, Brimonidine-DDS, bevasiranib sodium (e.g., Cand5), bertilimumab, AVA-101, ALG-1001, AL-39324, AGN-150998, ACU-4429, A6 (e.g., PARALIT®), TT-30, sFLT-01 gene therapy, RETINOSTAT®, PRS-050 (e.g., ANGIOCAL®), PF-4382923, Palomid-529, MC-1101, GW-824575, Dz13 (e.g., TRC-093), D93, CDX-1135 (e.g., TP10), ATL-1103, ARC-1905, XV-615, wet-AMD antibodies (e.g., pSivida), VEGF/rGel, VAR-10200, VAL-566-620-MULTI, TKI, TK-001, STP-601, dry AMD stem cell therapy (e.g., EyeCyte), OpRegen, SMT-D004, SAR-397769, RTU-007, RST-001, RGNX-004, RFE-007-CAI, retinal degeneration programme (e.g., ORPHAGEN), retinal cells (e.g., ISCO), ReN003, PRM-167, ProDex, Photoswitches (e.g., Photoswitch Biosciences), Parkinson's therapy, OMS-721, OC-10X, NV.AT.08, NT-503, NAFB002, NADPH oxidase inhibitors (e.g., Alimera Sciences), MC-2002, lycium anti-angiogenic proteoglycan, IXSVEGF, integrin inhibitors, GW-771806, GBS-007, Eos-013, EC-400, dry-AMD therapy (e.g., Neuron Systems), CGEN-25017, CERE-140, AP-202, AMD therapy (e.g., Valens Therapeutics), AMD therapy (e.g., Amarna Therapeutics), AMD RNAi therapy (e.g., RXi), ALK-001, AMD therapy (e.g., Acion1), AC-301, 4-IPP, zinc-monocysteine complexes (e.g., Adeona), vatalanib, TG-100-344, prinomastat, PMX-53, Neovastat, mecamylamine, JSM-6427, JPE-1375, CereCRIB, BA-285, ATX-S10, AG-13958, verteporfin/alphavβ3 conjugate, VEGF/rGel, VEGF-saporin, VEGF-R2 antagonist (e.g., Allostera), VEGF inhibitors (e.g., Santen), VEGF antagonists (e.g., Ark), VANGIOLUX®, Triphenylmethanes (e.g., Alimera), TG-100-801, TG-100-572, TA-106, T2-TrpRS, SU-0879, stem cell therapy (e.g., Pfizer and UCL), SOD mimetics (e.g., Inotek), SHEF-1, rostaporfin (e.g., PHOTREX®, PURLYTIN®, SnET2), RNA interference (e.g., Idera and Merck), rhCFHp (e.g., Optherion), retino-NPY, retinitis pigmentosa therapy (e.g., Mimetogen), AMD gene therapy (e.g., Novartis), retinal gene therapy (e.g., Genzyme), AMD gene therapy (e.g., Copernicus), retinal dystrophy ther (e.g., Fovea and Genzyme), Ramot project No. K-734B, PRS-055, porcine RPE cells (e.g., GenVec), PMI-002, PLG-101 (e.g., BiCentis®), PJ-34, PI3K conjugates (e.g., Semafore), PhotoPoint, Pharmaprojects No. 6526, pegaptanib sodium (e.g., SurModics®), PEDF ZFP TF, PEDF gene therapy (e.g., GenVec), PDS-1.0, PAN-90806, Opt-21, OPK-HVB-010, OPK-HVB-004, Ophthalmologicals (e.g., Cell NetwoRx), ophthalmic compounds (e.g., AstraZeneca and Alcon), OcuXan, NTC-200, NT-502, NOVA-21012, NEUROSOLVE®, neuroprotective (e.g., BDSI), MEDI-548, MCT-355, MCEYE®, LENTIVUE®, LYN-002, LX-213, lutetium texaphyrin (e.g., ANTRIN®), LG-339 inhibitors (e.g., Lexicon), KDR kinase inhibitors (e.g., Merck), ISV-616, INDUS-815C, ICAM-1 aptamer (e.g., Eyetech), hedgehog antagonists (e.g., Opthalmo), GTx-822, GS-102, Granzyme B/VEGF®, gene therapy (e.g., EyeGate), GCS-100 analogue programme, FOV-RD-27, fibroblast growth factor (e.g., Ramot), fenretinide, F-200 (e.g., Eos-200-F), PANZEM SR®, ETX-6991, ETX-6201, EG-3306, Dz-13, disulfiram (e.g., ORA-102), Diclofenac (e.g., Ophthalmopharma), ACU-02, CLT-010, CLT-009, CLT-008, CLT-007, CLT-006, CLT-005, CLT-004, CLT-003 (e.g., CHIROVIS®), CLT-001, CETHRIN® (e.g., BA-210), celecoxib, CD91 antagonist (e.g., Ophthalmophar), CB-42, BNC-4, bestrophin, batimastat, BA-1049, AVT-2, AVT-1, atu012, Ape1 programme (e.g., ApeX-2), anti-VEGF (e.g., Gryphon), AMD ZFPs (e.g., ToolGen), AMD therapy (e.g., Optherion), AMD therapy (e.g., ItherX), dry AMD therapy (e.g., Opko), AMD therapy (e.g., CSL), AMD therapies (e.g., Pharmacopeia and Allergan), AMD therapeutic protein (e.g., ItherX), AMD RNAi therapy (e.g., BioMolecular Therapeutics), AM-1101, ALN-VEG01, AK-1003, AGN-211745, ACUXSP-001 (e.g., EXCELLAIR®), ACU-HTR-028, ACUHHY-011, ACT-MD (e.g., NewNeural), ABCA4 modulators (e.g., Active Pass), A36 (e.g., Angstrom), 267268 (e.g., SB-267268), bevacizumab (e.g., VASTIN®), aflibercept (e.g., EYLEA®), 131-I-TM-601, vandetanib (e.g., CAPRELSA®, ZACTIMA®, ZICTIFA®), sunitinib malate (e.g., SUTENE®, SUTENT®), sorafenib (e.g., NEXAVAR®), pazopanib (e.g., ARMALA®, PATORMA®, VOTRIENT®), axitinib (e.g., INLYTA®), tivozanib, XL-647, RAF-265, pegdinetanib (e.g., ANGIOCEPT®), pazopanib, MGCD-265, icrucumab, foretinib, ENMD-2076, BMS-690514, regorafenib, ramucirumab, plitidepsin (e.g., APLIDIN®), orantinib, nintedanib (e.g., VARGATEF®), motesanib, midostaurin, linifanib, telatinib, lenvatinib, elpamotide, dovitinib, cediranib (e.g., RECENTIN®), JI-101, cabozantinib, brivanib, apatinib, ANGIOZYME®, X-82, SSR-106462, rebastinib, PF-337210, IMC-3C5, CYC116, AL-3818, VEGFR-2 inhibitor (e.g., AB Science), VEGF/rGel (e.g., Clayton Biotechnologies), TLK-60596, TLK-60404, R84 antibody (e.g., Peregrine), MG-516, FLT4 kinase inhibitors (e.g., Sareum), flt-4 kinase inhibitors, Sareum, DCC-2618, CH-330331, XL-999, XL-820, vatalanib, SU-14813, semaxanib, KRN-633, CEP-7055, CEP-5214, ZK-CDK, ZK-261991, YM-359445, YM-231146, VEGFR-2 kinase inhibitors (e.g., Takeda), VEGFR-2 kinase inhibitors (e.g., Hanmi), VEGFR-2 antagonist (e.g., Affymax), VEGF/rGel (e.g., Targa), VEGF-TK inhibitors (e.g., AstraZeneca), tyrosine kinase inhibitors (e.g., Abbott), tyrosine kinase inhibitors (e.g., Abbott), Tie-2 kinase inhibitors (e.g., GSK), SU-0879, SP-5.2, sorafenib bead (e.g., NEXAVAR® bead), SAR-131675, Ro-4383596, R-1530, Pharmaprojects No. 6059, OSI-930, OSI-817, OSI-632, MEDA300, L-000021649, KM-2550, kinase inhibitors (e.g., MethylGene), kinase inhibitors (e.g., Amgen), Ki-8751, KDR kinase inhibitors (e.g., Celltech), KDR kinase inhibitors (e.g., Merck), KDR kinase inhibitors (e.g., Amgen), KDR inhibitors (e.g., Abbott), KDR inhibitor (e.g., LGLS), JNJ-17029259, IMC-1C11, Flt 3/4 anticancer (e.g., Sentinel), EG-3306, DP-2514, DCC-2157, CDP-791, CB-173, c-kit inhibitors (e.g., Deciphera), BIW-8556, anticancers (e.g., Bracco and Dyax), anti-Flt-1 MAbs (e.g., ImClone), AGN-211745, AEE-788, or AB-434. In certain embodiments, the additional pharmaceutical agent is a pharmaceutical agent useful for treating and/or preventing dry eye, such as cyclosporine (RESTASIS®). In certain embodiments, the additional pharmaceutical agent is a pharmaceutical agent useful for treating and/or preventing cystoid macular edema (CME), such as an NSAID (e.g., bromfenac (BROMDAY®)). In certain embodiments, the additional pharmaceutical agent is a pharmaceutical agent useful for treating and/or preventing diabetic macular edema (DME), such as ranibizumab (LUCENTIS®). In certain embodiments, the additional pharmaceutical agent is a pharmaceutical agent useful for treating and/or preventing uveitis, such as TOBRADEX® (0.1% dexamethasone/0.3% tobramycin), ZYLET® (0.5% loteprednol etabonate/0.3% tobramycin)), triamcinolone acetonide (TRIVARIS® and TRIESENCE®), fluocinolone acetonide (RETISERTt®), and dexamethasone (OZURDEX®). In certain embodiments, the additional pharmaceutical agent is a pharmaceutical agent useful for treating and/or preventing glaucoma, such as latanoprost (XALATAN®), bimatoprost (LUMIGAN®), travoprost (TRAVATAN Z®), timolol (TIMOPTIC®), brimonidine tartrate (ALPHAGAN®), dorzolamide (TRUSOPT®), and pilocarpine (ISOPTO®). In certain embodiments, the additional pharmaceutical agent is a pharmaceutical agent useful for treating and/or preventing an ocular inflammatory disease (e.g., post-surgical inflammation), such as steroids (e.g., loteprednol etabonate (LOTEMAX®), difluprednate (DUREZOL®), prednisolone acetate (PRED MILD® and OMNIPRED®) and NSAIDs (e.g., bromfenac (BROMDAY®), nepafenac (NEVANAC®), ketorolac tromethamine (ACULAR LS®, ACUVAIL®, TORADOL®, and SPRIX®), diclofenac (VOLTRAN®, ACLONAC®, and CATAFLAM®).

Also encompassed by the invention are kits (e.g., pharmaceutical packs). The kits provided may comprise a pharmaceutical composition or crystalline form of Compound 3 of the invention and a container (e.g., a vial, ampule, bottle, syringe, and/or dispenser package, or other suitable container). In some embodiments, provided kits may optionally further include a second container comprising a pharmaceutical excipient for dilution or suspension of a pharmaceutical composition or crystalline form of Compound 3. In some embodiments, a pharmaceutical composition or crystalline form of Compound 3 provided in the first container and the second container are combined to form one unit dosage form.

Thus, in one aspect, provided are kits including a first container comprising a crystalline form of Compound 3 described herein, or a pharmaceutical composition thereof. In certain embodiments, the kits described herein are useful for preventing and/or treating a disease described herein. In certain embodiments, the kits described herein are useful for preventing and/or treating a disease associated with aberrant signaling of a growth factor (e.g., VEGF) in a subject in need thereof. In certain embodiments, the kits described herein are useful for preventing and/or treating a disease associated with abnormal angiogenesis in a subject in need thereof. In certain embodiments, the kits described herein are useful for preventing and/or treating proliferative diseases (e.g., cancers, benign neoplasms, inflammatory diseases, autoimmune diseases) and/or ocular diseases (e.g., macular degeneration, glaucoma, diabetic retinopathy, retinoblastoma, edema, uveitis, dry eye, or post-surgical inflammation). In certain embodiments, the kits described herein are useful for inhibiting aberrant signaling of a growth factor (e.g., VEGF) in a subject or cell in need thereof. In certain embodiments, the kits described herein are useful for inhibiting abnormal angiogenesis in a subject in need thereof. In certain embodiments, the kits further include instructions for administering the crystalline form of Compound 3, or the pharmaceutical composition thereof. The kits may also include information as required by a regulatory agency such as the U.S. Food and Drug Administration (FDA). In certain embodiments, the information included in the kits is prescribing information. In certain embodiments, the kits and instructions provide for treating and/or preventing a disease described herein. In certain embodiments, the kits and instructions provide for preventing and/or treating a disease associated with aberrant signaling of a growth factor (e.g., VEGF) in a subject in need thereof. In certain embodiments, the kits and instructions provide for preventing and/or treating a disease associated with abnormal angiogenesis in a subject in need thereof. In certain embodiments, the kits and instructions provide for inhibiting aberrant signaling of a growth factor (e.g., VEGF) in a subject or cell in need thereof. In certain embodiments, the kits and instructions provide for inhibiting abnormal angiogenesis in a subject in need thereof. The kit of the invention may include one or more additional pharmaceutical agents described herein as a separate composition.

Also provided by the present invention are particles comprising a crystalline form of Compound 3 described herein that may penetrate mucus, pharmaceutical compositions thereof, kits, and methods of using and preparing the particles and pharmaceutical compositions thereof. The pharmaceutical compositions, kits, and methods may involve modifying the surface coatings of particles, such as particles of pharmaceutical agents that have a low aqueous solubility. Such pharmaceutical compositions, kits, and methods can be used to achieve efficient transport of particles comprising the inventive crystalline forms of Compound 3 through mucus barriers in a subject.

In certain embodiments, the crystalline forms, particles, pharmaceutical compositions, kits, and methods of the invention are useful for applications in the eye, such as treating and/or preventing an ocular disease (e.g., macular degeneration, retinopathy, macular edema, retinal vein occlusion, dry eye syndrome, uveitis, allergic conjunctivitis, glaucoma, and rosacea).

The particles (e.g., nanoparticles and microparticles) of the invention comprise a crystalline form of Compound 3. In one particular aspect, the particles comprise crystalline Form B of Compound 3. The particles of the invention also include a surface-altering agent that modifies the surface of the particles to reduce the adhesion of the particles to mucus and/or to facilitate penetration of the particles through mucus.

The present invention also provides pharmaceutical compositions comprising the inventive particles. In certain embodiments, the pharmaceutical compositions of the invention can be topically administered to the eye of a subject. Topical pharmaceutical compositions are advantageous over pharmaceutical compositions that are administered by injection or orally.

Particles

The present invention also provides pharmaceutical compositions comprising a plurality of particles or crystals of the invention, which may be mucus-penetrating particles or crystals (MPPs). MPPs comprising crystalline Form A or crystalline Form B of Compound 3 useful in the present invention can be made as described, for example, in U.S. patent Publication Nos. 2013/0316001, 2013/0316006, 2013/0323179, 2013/0316009, 2012/0121718, 2010/0215580, and 2008/0166414, which are herein incorporated by reference in their entirety. Such pharmaceuticals compositions may be suitable for administration by various routes described herein. In one embodiment, pharmaceutical compositions comprising a plurality of particles comprising crystalline Form A or crystalline Form B of Compound 3, wherein the particles are mucus-penetrating particles, are formulated for delivery to the eye of a subject or to treat and/or prevent an ocular disease of a subject. In a preferred embodiment, the mucus-penetrating particles comprise crystalline Form B of Compound 3.

In some embodiments, the particles of the invention have a core-shell type configuration. The core may comprise a crystalline form of Compound 3, a polymeric carrier, a lipid, and/or a protein. The core may also comprise a gel or a liquid.

In some embodiments, the core is a solid. The solid may be, for example, a crystalline form of Compound 3 (e.g., crystalline Form B). In certain embodiments, the core is a gel or liquid (e.g., an oil-in-water or water-in-oil emulsion).

A crystalline form of Compound 3 (e.g., crystalline Form B) may be present in the core in any suitable amount, e.g., at least about 0.01 wt %, at least about 0.1 wt %, at least about 1 wt %, at least about 5 wt %, at least about 10 wt %, at least about 20 wt %, at least about 30 wt %, at least about 40 wt %, at least about 50 wt %, at least about 60 wt %, at least about 70 wt %, at least about 80 wt %, at least about 85 wt %, at least about 90 wt %, at least about 95 wt %, or at least about 99 wt % of the core. In one embodiment, the core is formed of 100 wt % of a crystalline form of Compound 3. In some cases, crystalline form of Compound 3 (e.g., crystalline Form B) may be present in the core at less than or equal to about 100 wt %, less than or equal to about 95 wt %, less than or equal to about 90 wt %, less than or equal to about 85 wt %, less than or equal to about 80 wt %, less than or equal to about 70 wt %, less than or equal to about 60 wt %, less than or equal to about 50 wt %, less than or equal to about 40 wt %, less than or equal to about 30 wt %, less than or equal to about 20 wt %, less than or equal to about 10 wt %, less than or equal to about 5 wt %, less than or equal to about 2 wt %, or less than or equal to about 1 wt % of the core. Combinations of the above-referenced ranges are also possible (e.g., present in an amount of at least about 80 wt % and less than or equal to about 100 wt % of the core). Other ranges are also possible. In one embodiment, a crystalline form of Compound 3 (e.g., crystalline Form B) comprises at least 90 wt % of the core of a particle of the invention. In another embodiment, a crystalline form of Compound 3 (e.g., crystalline Form B) comprises at least 95 wt % of the core of a particle of the invention.

When a polymer is present in the core, the polymer may be present in the core in any suitable amount, e.g., less than about 100 wt %, less than about 80 wt %, less than about 60 wt %, less than about 50 wt %, less than about 40 wt %, less than about 30 wt %, less than about 20 wt %, less than about 10 wt %, less than about 5 wt %, or less than about 1 wt %. In some cases, the polymer may be present in an amount of at least about 1 wt %, at least about 5 wt %, at least about 10 wt %, at least about 20 wt %, at least about 30 wt %, at least about 40 wt %, at least about 50 wt %, at least about 75 wt %, at least about 90 wt %, or at least about 99 wt % in the core. Combinations of the above-referenced ranges are also possible (e.g., present in an amount of at least about 1 wt % and less than about 20 wt %). Other ranges are also possible. In some embodiments, the core is substantially free of a polymeric component.

The core may have any suitable shape and/or size. For instance, the core may be substantially spherical, non-spherical, oval, rod-shaped, pyramidal, cube-like, disk-shaped, wire-like, or irregularly shaped. The core may have a largest or smallest cross-sectional dimension of, for example, less than about 10 μm, less than about 3 μm, less than about 1 μm, less than about 500 nm, less than about 400 nm, less than about 300 nm, less than about 200 nm, less than about 100 nm, less than about 30 nm, or less than about 10 nm. In some cases, the core may have a largest or smallest cross-sectional dimension of, for example, at least about 10 nm, at least about 30 nm, at least about 100 nm, at least about 200 nm, at least about 300 nm, at least about 400 nm, at least about 500 nm, at least about 1 μm, or at least about 3 μm. Combinations of the above-referenced ranges are also possible (e.g., a largest or smallest cross-sectional dimension of at least about 30 nm and less than about 500 nm). Other ranges are also possible. In some embodiments, the sizes of the cores formed by a process described herein have a Gaussian-type distribution. Unless indicated otherwise, the measurements of the particle sizes or core sizes refer to the smallest cross-sectional dimension.

Techniques to determine sizes (e.g., smallest or largest cross-sectional dimensions) of particles are known in the art. Examples of suitable techniques include dynamic light scattering (DLS), transmission electron microscopy, scanning electron microscopy, electroresistance counting and laser diffraction. Although many methods for determining sizes of particles are known, the sizes described herein (e.g., average particle sizes and thicknesses) refer to ones measured by DLS.

In some embodiments, a substantial portion of the core is formed of a crystalline form of Compound 3 as described herein that can lead to certain beneficial and/or therapeutic effects. The core may be, for example, a nanocrystal (i.e., a nanocrystalline particle) of a crystalline form of Compound 3. In certain embodiments, the core includes a polymeric carrier, optionally with a crystalline form of Compound 3 encapsulated or otherwise associated with the core. In certain embodiments, the core includes a lipid, protein, gel, liquid, and/or another suitable material to be delivered to a subject. The core includes a surface to which one or more surface-altering agents can be attached.

In some embodiments, the core is surrounded by coating, which includes an inner surface and an outer surface. The coating may be formed, at least in part, of one or more surface-altering agents, such as a polymer (e.g., a block copolymer and/or a polymer having pendant hydroxyl groups), which may associate with the surface of the core. The surface-altering agent may be associated with the core particle by, for example, being covalently attached to the core particle, non-covalently attached to the core particle, adsorbed to the core, or attached to the core through ionic interactions, hydrophobic and/or hydrophilic interactions, electrostatic interactions, van der Waals interactions, or combinations thereof.

The coating and/or surface-altering agent of the particles of the invention may comprise any suitable material, such as a hydrophobic material, a hydrophilic material, and/or an amphiphilic material. In some embodiments, the coating includes a polymer. In certain embodiments, the polymer is a synthetic polymer (i.e., a polymer not produced in nature). In other embodiments, the polymer is a natural polymer (e.g., a protein, polysaccharide, or rubber). In certain embodiments, the polymer is a surface active polymer. In certain embodiments, the polymer is a non-ionic polymer. In certain embodiments, the polymer is a linear synthetic non-ionic polymer. In certain embodiments, the polymer is a non-ionic block copolymer. The polymer may be a copolymer. In certain embodiments, one repeat unit of the copolymer is relatively hydrophobic and another repeat unit of the copolymer is relatively hydrophilic. The copolymer may be, for example, a diblock, triblock, alternating, or random copolymer. The polymer may be charged or uncharged.

Non-limiting examples of suitable polymers of the coating may include polyamines, polyethers, polyamides, polyesters, polycarbamates, polyureas, polycarbonates, polystyrenes, polyimides, polysulfones, polyurethanes, polyacetylenes, polyethylenes, polyethyleneimines, polyisocyanates, polyacrylates, polymethacrylates, polyacrylonitriles, and polyarylates. Non-limiting examples of specific polymers include poly(caprolactone) (PCL), ethylene vinyl acetate polymer (EVA), poly(lactic acid) (PLA), poly(L-lactic acid) (PLLA), poly(glycolic acid) (PGA), poly(lactic acid-co-glycolic acid) (PLGA), poly(L-lactic acid-co-glycolic acid) (PLLGA), poly(D,L-lactide) (PDLA), poly(L-lactide) (PLLA), poly(D,L-lactide-co-caprolactone), poly(D,L-lactide-co-caprolactone-co-glycolide), poly(D,L-lactide-co-PEO-co-D,L-lactide), poly(D,L-lactide-co-PPO-co-D,L-lactide), polyalkyl cyanoacrylate, polyurethane, poly-L-lysine (PLL), hydroxypropyl methacrylate (HPMA), poly(ethylene glycol), poly-L-glutamic acid, poly(hydroxy acids), polyanhydrides, polyorthoesters, poly(ester amides), polyamides, poly(ester ethers), polycarbonates, polyalkylenes such as polyethylene and polypropylene, polyalkylene glycols such as poly(ethylene glycol) (PEG), polyalkylene terephthalates such as poly(ethylene terephthalate), polyvinyl alcohols (PVA), polyvinyl ethers, polyvinyl esters such as poly(vinyl acetate), polyvinyl halides such as poly(vinyl chloride) (PVC), polyvinylpyrrolidone, polysiloxanes, polystyrene (PS), polyurethanes, derivatized celluloses such as alkyl celluloses, hydroxyalkyl celluloses, cellulose ethers, cellulose esters, nitro celluloses, hydroxypropylcellulose, carboxymethylcellulose, polymers of acrylic acids, such as poly(methyl(meth)acrylate) (PMMA), poly(ethyl(meth)acrylate), poly(butyl(meth)acrylate), poly(isobutyl(meth)acrylate), poly(hexyl(meth)acrylate), poly(isodecyl(meth)acrylate), poly(lauryl(meth)acrylate), poly(phenyl(meth)acrylate), poly(methyl acrylate), poly(isopropyl acrylate), poly(isobutyl acrylate), poly(octadecyl acrylate) (jointly referred to herein as "polyacrylic acids"), and copolymers and mixtures thereof, polydioxanone and its copolymers, polyhydroxyalkanoates, polypropylene fumarate), polyoxymethylene, poloxamers, poly(ortho)esters, poly(butyric acid), poly(valeric acid), poly(lactide-co-caprolactone), and trimethylene carbonate.

The molecular weight of the polymer of the coating may vary. In some embodiments, the molecular weight of the polymer of the coating is at least about 0.5 kDa, at least about 1 kDa, at least about 1.8 kDa, at least about 2 kDa, at least about 3 kDa, at least about 4 kDa, at least about 5 kDa, at least about 6 kDa, at least about 8 kDa, at least about 10 kDa, at least about 12 kDa, at least about 15 kDa, at least about 20 kDa, at least about 30 kDa, at least about 40 kDa, or at least about 50 kDa. In some embodiments, the molecular weight of the polymer of the coating is less than about 50 kDa, less than about 40 kDa, less than about 30 kDa, less than about 20 kDa, less than about 12 kDa, less than about 10 kDa, less than about 8 kDa, less than about 6 kDa, less than about 5 kDa, or less than about 4 kDa. Combinations of the above-referenced ranges are possible (e.g., a molecular weight of at least about 2 kDa and less than about 15 kDa). Other ranges are also possible. The molecular weight of the polymer of the coating may be determined using any known technique such as light-scattering and gel permeation chromatography. Other methods are known in the art. Although the particles of the invention, and the coating thereof, may each include polymers, in some embodiments, the particles of the invention comprise a hydrophobic material that is not a polymer or pharmaceutical agent. Non-limiting examples of non-polymeric hydrophobic materials include, for example, metals, waxes, and organic materials (e.g., organic silanes and perfluorinated or fluorinated organic materials).

In some embodiments, the surface-altering agents, or portions thereof, are chosen to facilitate transport of the particle through or into a mucosal barrier (e.g., mucus or a mucosal membrane). In certain embodiments described herein, one or more surface-altering agents are oriented in a particular configuration in the coating. In some embodiments, in which a surface-altering agent is a triblock copolymer, such as a triblock copolymer having a (hydrophilic block)-(hydrophobic block)-(hydrophilic block) configuration, a hydrophobic block may be oriented towards the surface of the core, and hydrophilic blocks may be oriented away from the core surface (e.g., towards the exterior of the particle). The hydrophilic blocks may have characteristics that facilitate transport of the particle through a mucosal barrier. The particular chemical makeup and/or components of the coating and surface-altering agent(s) can be chosen so as to impart certain functionality to the particles, such as enhanced transport through mucosal barriers.

In some embodiments, at least one particle of the invention includes a core and a coating surrounding the core. A particle including a core and a coating on the core is referred to as a "coated particle." In certain embodiments, at least one particle of the invention includes a core but not a coating on the core. A particle including a core but not a coating on the core is referred to as an "uncoated particle."

It should be understood that a coating which surrounds a core need not completely surround the core, although such embodiments may be possible. For example, the coating may surround at least about 10%, at least about 30%, at least about 50%, at least about 70%, at least about 90%, or at least about 99% of the surface area of a core. In some cases, the coating substantially surrounds a core. In other cases, the coating completely surrounds a core. In other embodiments, a coating surrounds less than about 100%, less than about 90%, less than about 70%, or less than about 50% of the surface area of a core. Combinations of the above-referenced ranges are also possible (e.g., surrounding at least 70% and less than 100% of the surface area of a core).

The material of the coating may be distributed evenly across a surface of the core in some cases, and unevenly in other cases. For example, the coating may include portions (e.g., holes) that do not include any material. If desired, the coating may be designed to allow penetration and/or transport of certain molecules and components into or out of the coating, but may prevent penetration and/or transport of other molecules and components into or out of the coating. The ability of certain molecules to penetrate and/or be transported into and/or across a coating may depend on, for example, the packing density of the surface-altering agents forming the coating and the chemical and physical properties of the components forming the coating. As described herein, the coating may include one layer of material (i.e., a monolayer) or multilayers of materials. A single type or multiple types of surface-altering agent may be present.

The coating of particles of the invention can have any suitable thickness. For example, the coating may have an average thickness of at least about 1 nm, at least about 3 nm, at least about 10 nm, at least about 30 nm, at least about 100 nm, at least about 300 nm, at least about 1 μm, or at least about 3 μm. In some cases, the average thickness of the coating is less than about 3 μm, less than about 1 μm, less than about 300 nm, less than about 100 nm, less than about 30 nm, less than about 10 nm, or less than about 3 nm. Combinations of the above-referenced ranges are also possible (e.g., an average thickness of at least about 1 nm and less than about 100 nm). Other ranges are also possible. For particles having multiple coatings, each coating may have one of the thicknesses described herein.

The pharmaceutical compositions of the invention may allow for the coating of the particles of the invention with hydrophilic surface-altering moieties without requiring covalent association of the surface-altering moieties to the surface of the core. In some embodiments, the core having a hydrophobic surface is coated with a polymer described herein, thereby causing a plurality of surface-altering moieties to be on the surface of the core without substantially altering the characteristics of the core itself. For example, the surface altering agent may be present on (e.g., adsorbed to) the outer surface of the core. In other embodiments, a surface-altering agent is covalently linked to the core.

In certain embodiments in which the surface-altering agent is adsorbed onto a surface of the core, the surface-altering agent may be in equilibrium with other molecules of the surface-altering agent in solution, optionally with other components (e.g., in a pharmaceutical composition). In some cases, the adsorbed surface-altering agent may be present on the surface of the core at a density described herein. The density may be an average density as the surface altering agent is in equilibrium with other components in solution.

In some embodiments, the present invention relates to coated particles comprising a core comprising crystalline Form A or crystalline Form B of Compound 3 described herein and a coating surrounding the core. In some embodiments, the coating comprises a hydrophilic material. The coating may comprise one or more surface-altering agents described herein, such as a polymer and/or a surfactant (e.g., a PVA, a poloxamer, a polysorbate (e.g., TWEEN 80®)). Other coatings or surface-altering agents useful in the present invention are described, for example, in U.S. patent Publication Nos. 2013/0316001, 2013/0316006, 2013/0323179, 2013/0316009, 2012/0121718, 2010/0215580, and 2008/0166414, which are herein incorporated by reference in their entirety.

In some embodiments, the compositions and methods involve the use of poloxamers that aid particle transport in mucus. Poloxamers are typically nonionic triblock copolymers comprising a central hydrophobic block (e.g., a poly(propylene oxide) block) flanked by two hydrophilic blocks (e.g., poly(ethylene oxide) blocks). Poloxamers have the trade name PLURONIC®. Examples of PLURONIC® polymers that may be useful in the embodiments described herein include, but are not limited to, F127 (poloxamer 407), F38, F108 (poloxamer 338), F68, F77, F87, F88, F98, L101, L121, L31, L35, L43, L44, L61, L62, L64, L81, L92, N3, P103, P104, P105, P123, P65, P84, and P85. In certain embodiments, the molecular weight of the hydrophobic block of the triblock copolymer of the (hydrophilic block)-(hydrophobic block)-(hydrophilic block) configuration is at least about 2 kDa, and the two hydrophilic blocks constitute at least about 15 wt % of the triblock copolymer.

In certain embodiments, the compositions and methods involve the use of polysorbates that aid particle transport in mucus. Polysorbates are typically derived from PEGylated sorbitan (a derivative of sorbitol) esterified with fatty acids. Common brand names for polysorbates include TWEEN®, ALKEST®, CANARCEL®. Examples of polysorbates include polyoxyethylene sorbitan monooleate (e.g., TWEEN 80®), polyoxyethylene sorbitan monostearate (e.g., TWEEN 60®), polyoxyethylene sorbitan monopalmitate (e.g., TWEEN 40®), and polyoxyethylene sorbitan monolaurate (e.g., TWEEN 20®).

It should be understood that components and configurations other than those described herein may be suitable for certain particles and pharmaceutical compositions, and that not all of the components described are necessarily present in some embodiments.

In some embodiments, particles of the invention, when introduced into a subject, may interact with one or more components in the subject such as mucus, cells, tissues, organs, particles, fluids (e.g., blood), microorganisms, and portions or combinations thereof. In some embodiments, the coating of the inventive particle can be designed to include surface-altering agents or other components with properties that allow favorable interactions (e.g., transport, binding, and adsorption) with one or more materials from the subject. For example, the coating may include surface-altering agents or other components having a certain hydrophilicity, hydrophobicity, surface charge, functional group, specificity for binding, and/or density to facilitate or reduce particular interactions in the subject. One example is choosing a hydrophilicity, hydrophobicity, surface charge, functional group, specificity for binding, and/or density of one or more surface-altering agents to reduce the physical and/or chemical interactions between the particle and mucus of the subject, so as to enhance the mobility of the particle through mucus. Other examples are described in more detail below.

In some embodiments, once a particle is successfully transported into and/or across a mucosal barrier (e.g., mucus or a mucosal membrane) in a subject, further interactions between the particle and the subject may take place. In some embodiments, in which the core comprises a pharmaceutical agent or compound of the invention, the conversion, breakdown, release, and/or transport of the pharmaceutical agent from the particle can lead to certain beneficial and/or therapeutic effects in the subject. Therefore, the particles of the invention can be used for the treatment and/or prevention of certain diseases.

Examples for the use of the particles of the invention are provided below in the context of being suitable for administration to a mucosal barrier (e.g., mucus or a mucosal membrane) in a subject. It should be appreciated that while many of the embodiments herein are described in this context, and in the context of providing a benefit for diseases that involve transport of materials across a mucosal barrier, the invention is not limited as such, and the particles, pharmaceutical compositions, and kits of the invention may be used to treat and/or prevent other diseases.

In some embodiments, the pharmaceutical compositions of the invention comprise MPPs that include a crystalline form of Compound 3 and optionally at least one additional pharmaceutical agent, each of which is associated with polymer carriers via encapsulation or other processes. In other embodiments, the pharmaceutical compositions of the invention comprise MPPs without any polymeric carriers or with minimal use of polymeric carriers. Polymer-based MPPs may have one or more inherent limitations in some embodiments. In particular, in light of drug delivery applications, these limitations may include one or more of the following. A) Low drug encapsulation efficiency and low drug loading: encapsulation of drugs into polymeric particles is often inefficient, as generally less than 10% of the total amount of drug used gets encapsulated into particles during manufacturing; additionally, drug loadings above 50% are rarely achieved. B) Convenience of usage: pharmaceutical compositions based on drug-loaded polymeric particles, in general, typically need to be stored as dry powder to avoid premature drug release and thus require either point-of-use re-constitution or a sophisticated dosing device. C) Biocompatibility: accumulation of slowly degrading polymer carriers following repeated dosing and their toxicity over the long term present a major concern for polymeric drug carriers. D) Chemical and physical stability: polymer degradation may compromise stability of encapsulated drugs. In many encapsulation processes, the drug undergoes a transition from a solution phase to a solid phase, which is not well-controlled in terms of physical form of the emerging solid phase (i.e., amorphous vs. crystalline vs. crystalline polymorphs); this is a concern for multiple aspects of pharmaceutical composition performance, including physical and chemical stability and release kinetics. E) Manufacturing complexity: manufacturing, especially scalability, of drug-loaded polymeric MPPs is a fairly complex process that may involve multiple steps and a considerable amount of toxic organic solvents. Therefore, by avoiding or minimizing the need to encapsulate pharmaceutical agents into polymeric carriers, certain limitations of polymeric MPPs with respect to drug loading, convenience of usage, biocompatibility, stability, and/or complexity of manufacturing, may be addressed.

It should be appreciated, however, that in other embodiments, pharmaceutical agents may be associated with polymer carriers via encapsulation or other processes. Thus, the description provided herein is not limited in this respect. For instance, despite the above-mentioned drawbacks of certain mucus-penetrating particles including a polymeric carrier, in certain embodiments such particles may be preferred. For example, it may be preferable to use polymer carriers for controlled release purposes and/or for encapsulating certain pharmaceutical agents that are difficult to formulate into particles. As such, in some embodiments described herein, particles that include a polymer carrier are described.

In some embodiments, the pharmaceutical compositions of the invention involve the use of poly(vinyl alcohols) (PVAs), a water-soluble non-ionic synthetic polymer, to aid particle transport in mucus, such as described in U.S. patent Publication No. 2013/0316009, which is herein incorporated by referenced in its entirety. The pharmaceutical compositions may involve making MPPs or MPCs by, for example, an emulsification process in the presence of specific PVAs. In certain embodiments, the pharmaceutical compositions and methods involve making MPPs or MPCs from prefabricated particles by non-covalent coating with specific PVAs. In some embodiments, the pharmaceutical compositions and methods involve making MPPs in the presence of specific PVAs without any polymeric carriers or with minimal use of polymeric carriers. It should be appreciated, however, that in other embodiments, polymeric carriers can be used.

Particles with Reduced Mucoadhesion

Particles of the invention comprising crystalline forms of Compound 3 (e.g., crystalline Form B) may have reduced mucoadhesiveness. A material in need of increased diffusivity through mucus may be hydrophobic, may include many hydrogen bond donors or acceptors, and/or may be highly charged. In some cases, the material may include a crystalline or amorphous solid material. The material, which may serve as a core, may be coated with a suitable polymer described herein, thereby forming a particle with a plurality of surface-altering moieties on the surface, resulting in reduced mucoadhesion. Particles of the invention having reduced mucoadhesion may alternatively be characterized as having increased transport through mucus, being mobile in mucus, or mucus-penetrating (i.e., mucus-penetrating particles), meaning that the particles are transported through mucus faster than a negative control particle. The negative control particle may be a particle that is known to be mucoadhesive, e.g., an unmodified particle or core that is not coated with a coating described herein, such as a 200 nm carboxylated polystyrene particle.

Particles of the invention may be adapted for delivery (e.g., ocular delivery) to mucus or a mucosal surface of a subject. The particles with surface-altering moieties may be delivered to the mucosal surface of a subject, may pass through the mucosal barrier in the subject, and/or prolonged retention and/or increased uniform distribution of the particles at mucosal surfaces, e.g., due to reduced mucoadhesion.

Furthermore, in some embodiments, the particles of the invention having reduced mucoadhesion facilitate better distribution of the particles at the surface of a tissue of a subject and/or have a prolonged presence at the surface of the tissue, compared to particles that are more mucoadhesive. For example, a luminal space such as the gastrointestinal tract is surrounded by a mucus-coated surface. Mucoadhesive particles delivered to such a space are typically removed from the luminal space and from the mucus-coated surface by the subject's natural clearance mechanisms. The particles of the invention with reduced mucoadhesion may remain in the luminal space for relatively longer periods compared to the mucoadhesive particles. This prolonged presence may prevent or reduce clearance of the particles and/or may allow for better distribution of the particles on the surface of the tissue. The prolonged presence may also affect the particle transport through the luminal space, e.g., the particles may distribute into the mucus layer and may reach the underlying epithelium.

In certain embodiments, the core of the particles of the invention coated with the polymer of the coating may pass through mucus or a mucosal barrier in a subject, exhibit prolonged retention, and/or increase uniform distribution of the particles at mucosal surfaces, e.g., such substances are cleared more slowly (e.g., at least about 2 times, about 5 times, about 10 times, or even at least about 20 times more slowly) from a subject's body as compared to a negative control particle of the invention.

The mobility of the particles of the invention in mucus may be characterized in, e.g., the relative velocity and/or diffusivity of the particles. In certain embodiments, the particles of the invention have certain relative velocity, $<V_{mean}>_{rel}$, which is defined as follows:

$$<V_{mean}>_{rel} = \frac{<V_{mean}>_{Sample} - <V_{mean}>_{Negative\ control}}{<V_{mean}>_{Positive\ control} - <V_{mean}>_{Negative\ control}} \quad \text{(Equation 1)}$$

wherein:

$<V_{mean}>$ is the ensemble average trajectory-mean velocity;

$V_{mean}$ is the velocity of an individual particle averaged over its trajectory;

the sample is the particle of interest;

the negative control is a 200 nm carboxylated polystyrene particle; and the positive control is a 200 nm polystyrene particle densely PEGylated with 2-5 kDa PEG.

The relative velocity can be measured by a multiple particle tracking technique. For instance, a fluorescent microscope equipped with a CCD camera can be used to capture 15 s movies at a temporal resolution of 66.7 ms (15 frames/s) under 100× magnification from several areas within each sample for each type of particles: sample, negative control, and positive control. The sample, negative control, and positive control may be fluorescent particles to observe tracking. Alternatively non-fluorescent particles may be coated with a fluorescent molecule, a fluorescently tagged surface agent, or a fluorescently tagged polymer. An advanced image processing software (e.g., Image Pro or MetaMorph) can be used to measure individual trajectories of multiple particles over a time-scale of at least 3.335 s (50 frames).

In some embodiments, a particle described herein has a relative velocity of greater than or equal to about 0.3, greater than or equal to about 0.4, greater than or equal to about 0.5, greater than or equal to about 0.6, greater than or equal to about 0.7, greater than or equal to about 0.8, greater than or equal to about 0.9, greater than or equal to about 1.0, greater than or equal to about 1.1, greater than or equal to about 1.2, greater than or equal to about 1.3, greater than or equal to about 1.4, greater than or equal to about 1.5, greater than or equal to about 1.6, greater than or equal to about 1.7, greater than or equal to about 1.8, greater than or equal to about 1.9 or greater than or equal to about 2.0 in mucus. In some embodiments, a particle described herein has a relative velocity of less than or equal to about 10.0, less than or equal to about 8.0, less than or equal to about 6.0, less than or equal to about 4.0, less than or equal to about 3.0, less than or equal to about 2.0, less than or equal to about 1.9, less than or equal to about 1.8, less than or equal to about 1.7, less than or equal to about 1.6, less than or equal to about 1.5, less than or equal to about 1.4, less than or equal to about 1.3, less than or equal to about 1.2, less than or equal to about 1.1, less than or equal to about 1.0, less than or equal to about 0.9, less than or equal to about 0.8, or less than or equal to about 1.7 in mucus. Combinations of the above-noted ranges are possible (e.g., a relative velocity of greater than or equal to about 0.5 and less than or equal to about 6.0). Other ranges are also possible. The mucus may be, for example, human cervicovaginal mucus.

In certain embodiments, a particle described herein can diffuse through mucus or a mucosal barrier at a greater rate or diffusivity than a control particle or a corresponding particle (e.g., a corresponding particle that is unmodified and/or is not coated with a coating described herein). In some cases, a particle described herein may pass through mucus or a mucosal barrier at a rate of diffusivity that is at least about 10 times, 20 times, 30 times, 50 times, 100 times, 200 times, 500 times, 1000 times, 2000 times, 5000 times, 10000 times, or more, higher than a control particle or a corresponding particle. In some cases, a particle described herein may pass through mucus or a mucosal barrier at a rate of diffusivity that is less than or equal to about 10000 times higher, less than or equal to about 5000 times higher, less than or equal to about 2000 times higher, less than or equal to about 1000 times higher, less than or equal to about 500 times higher, less than or equal to about 200 times higher, less than or equal to about 100 times higher, less than or equal to about 50 times higher, less than or equal to about 30 times higher, less than or equal to about 20 times higher, or less than or equal to about 10 times higher than a control particle or a corresponding particle. Combinations of the above-referenced ranges are also possible (e.g., at least about 10 times and less than or equal to about 1000 times higher than a control particle or a corresponding particle). Other ranges are also possible.

For the purposes of the comparisons described herein, the corresponding particles may be approximately the same size, shape, and/or density as the particles of the invention but lack the coating that makes the particles of the invention mobile in mucus. In some embodiments, the measurement of the geometric mean square displacement and rate of diffusivity of the particles (e.g., the corresponding particles and particles of the invention) is based on a time scale of about 1 second, about 3 seconds, or about 10 seconds. Methods for determining the geometric mean square displacement and rate of diffusivity are known in the art. The particles of the invention may pass through mucus or a mucosal barrier with a geometric mean squared displacement that is at least about 10 times, about 30 times, about 100 times, about 300 times, about 1000 times, about 3000 times, about 10000 times higher than corresponding particles or negative control particles. In some embodiments, the particles of the invention pass through mucus or a mucosal barrier with a geometric mean squared displacement that is less than about 10000 times higher, less than about 3000 times higher, less than about 1000 times higher, less than about 300 times higher, less than about 100 times higher, less than about 30 times higher, or less than about 10 times higher than negative control particles or corresponding particles. Combinations of the above-referenced ranges are also possible (e.g., at least about 10 times and less than about 1000 times higher than negative control particles or corresponding particles). Other ranges are also possible.

In some embodiments, particles of the invention diffuse through a mucosal barrier at a rate approaching the rate or diffusivity at which the particles can diffuse through water. In some embodiments, the particles of the invention pass through a mucosal barrier at a rate or diffusivity that is less than about 1/100, less than about 1/300, less than about 1/1000, less than about 1/3000, less than about 1/10,000 of the diffusivity that the particles diffuse through water under similar conditions. In some embodiments, particles of the invention pass through a mucosal barrier at a rate or diffusivity that is greater than or equal to about 1/10,000, greater than or equal to about 1/3000, greater than or equal to about 1/1000, greater than or equal to about 1/300, or greater than or equal to about 1/100 of the diffusivity that the particles diffuse through water under similar conditions. Combinations of the above-referenced ranges are also possible (e.g., greater than or equal to about 1/3000 and less than 1/300 the diffusivity that the particles diffuse through water under similar conditions). Other ranges are also possible. The measurement of diffusivity may be based on a time scale of about 1 second, or about 0.5 second, or about 2 seconds, or about 5 seconds, or about 10 seconds.

In some embodiments, the particles of the invention diffuse through human cervicovaginal mucus at a diffusivity that is less than about 1/500 of the diffusivity that the particles diffuse through water. In some embodiments, the measurement of diffusivity is based on a time scale of about 1 second, or about 0.5 second, or about 2 seconds, or about 5 seconds, or about 10 seconds.

In certain embodiments, the present invention provides particles that travel through mucus, such as human cervicovaginal mucus, at certain absolute diffusivities. For example, the particles of described herein may travel at diffusivities of at least about $1\times10^{-4}$ µm/s, $2\times10^{-4}$ µm/s, $5\times10^{-4}$ µm/s, $1\times10^{-3}$ µm/s, $2\times10^{-3}$ µm/s, $5\times10^{-3}$ µm/s, $1\times10^{-2}$ µm/s, $2\times10^{-2}$ µm/s, $4\times10^{-2}$ µm/s, $5\times10^{-2}$ µm/s, $6\times10^{-2}$ µm/s, $8\times10^{-2}$ µm/s, $1\times10^{-1}$ µm/s, $2\times10^{-1}$ µm/s, $5\times10^{-1}$ µm/s, 1 µm/s, or 2 µm/s. In some cases, the particles may travel at diffusivities of less than or equal to about 2 µm/s, less than or equal to about 1 µm/s, less than or equal to about $5\times10^{-1}$ µm/s, less than or equal to about $2\times10^{-1}$ µm/s, less than or equal to about $1\times10^{-1}$ µm/s, less than or equal to about $8\times10^{-2}$ µm/s, less than or equal to about $6\times10^{-2}$ µm/s, less than or equal to about $5\times10^{-2}$ µm/s, less than or equal to about $4\times10^{-2}$ µm/s, less than or equal to about $2\times10^{-2}$ µm/s, less than or equal to about $1\times10^{-2}$ µm/s, less than or equal to about $5\times10^{-3}$ µm/s, less than or equal to about $2\times10^{-3}$ µm/s, less than or equal to about $1\times10^{-3}$ µm/s, less than or equal to about $5\times10^{-4}$ µm/s, less than or equal to about $2\times10^{-4}$ µm/s, or less than or equal to about $1\times10^{-4}$ µm/s. Combinations of the above-referenced ranges are also possible (e.g., greater than or equal to about $2\times10^{-4}$ µm/s and less than or equal to about $1\times10^{-1}$ µm/s). Other ranges are also possible. In some cases, the measurement is based on a time scale of about 1 second, or about 0.5 second, or about 2 seconds, or about 5 seconds, or about 10 seconds.

It should be appreciated that while the mobility (e.g., relative velocity and diffusivity) of the particles of the invention may be measured in human cervicovaginal mucus, the mobility may be measured in other types of mucus as well.

In certain embodiments, a particle described herein comprises surface-altering moieties at a given density. The surface-altering moieties may be the portions of a surface-altering agent that are, for example, exposed to the solvent containing the particle. As an example, the hydrolyzed units/blocks of PVA may be surface-altering moieties of the surface-altering agent PVA. In another example, the PEG segments may be surface-altering moieties of the surface-altering agent PEG-PPO-PEG. In some cases, the surface-altering moieties and/or surface-altering agents are present at a density of at least about 0.001 units or molecules per $nm^2$, at least about 0.002, at least about 0.005, at least about 0.01, at least about 0.02, at least about 0.05, at least about 0.1, at least about 0.2, at least about 0.5, at least about 1, at least about 2, at least about 5, at least about 10, at least about 20, at least about 50, at least about 100 units or molecules per $nm^2$, or more units or molecules per $nm^2$. In some cases, the surface-altering moieties and/or surface-altering agents are present at a density of less than or equal to about 100 units or molecules per $nm^2$, less than or equal to about 50, less than or equal to about 20, less than or equal to about 10, less than or equal to about 5, less than or equal to about 2, less than or equal to about 1, less than or equal to about 0.5, less than or equal to about 0.2, less than or equal to about 0.1, less than or equal to about 0.05, less than or equal to about 0.02, or less than or equal to about 0.01 units or molecules per $nm^2$. Combinations of the above-referenced ranges are possible (e.g., a density of at least about 0.01 and less than or equal to about 1 units or molecules per $nm^2$). Other ranges are also possible. In some embodiments, the density values described above may be an average density as the surface altering agent is in equilibrium with other components in solution.

Those skilled in the art would be aware of methods to estimate the average density of surface-altering moieties (see, for example, Budijono et al., *Colloids and Surfaces A: Physicochem. Eng. Aspects* 2010, 360, 105-110; Joshi et al., *Anal. Chim. Acta* 1979, 104,153-160). For example, as described herein, the average density of surface-altering moieties can be determined using HPLC quantitation and DLS analysis. A suspension of particles for which surface density determination is of interest is first sized using DLS: a small volume is diluted to an appropriate concentration (e.g., about 100 μg/mL), and the z-average diameter is taken as a representative measurement of particle size. The remaining suspension is then divided into two aliquots. Using HPLC, the first aliquot is assayed for the total concentration of core material and for the total concentration of the surface-altering moiety. Again using HPLC, the second aliquot is assayed for the concentration of free or unbound surface-altering moiety. In order to get only the free or unbound surface-altering moiety from the second aliquot, the particles, and therefore any bound surface-altering moiety, are removed by ultracentrifugation. By subtracting the concentration of the unbound surface-altering moiety from the total concentration of surface-altering moiety, the concentration of bound surface-altering moiety can be determined. Since the total concentration of core material was also determined from the first aliquot, the mass ratio between the core material and the surface-altering moiety can be determined. Using the molecular weight of the surface-altering moiety the number of surface-altering moiety to mass of core material can be calculated. To turn this number into a surface density measurement, the surface area per mass of core material needs to be calculated. The volume of the particle is approximated as that of a sphere with the diameter obtained from DLS allowing for the calculation of the surface area per mass of core material. In this way the number of surface-altering moieties per surface area can be determined.

In certain embodiments, the particles of the invention comprise surface-altering moieties and/or agents that affect the zeta-potential of the particle. The zeta potential of the particle may be, for example, at least about −100 mV, at least about −30 mV, at least about −10 mV, at least about −3 mV, at least about 3 mV, at least about 10 mV, at least about 30 mV, or at least about 100 mV. The zeta potential of the particle may also be, for example, less than about 100 mV, less than about 30 mV, less than about 10 mV, less than about 3 mV, less than about −3 mV, less than about −10 mV, less than about −30 mV, or less than about −100 mV. Combinations of the above-referenced ranges are possible (e.g., a zeta-potential of at least about −30 mV and less than about 30 mV). Other ranges are also possible.

The coated particles described herein may have any suitable shape and/or size. In some embodiments, a coated particle has a shape substantially similar to the shape of the core. In some cases, a coated particle described herein may be a nanoparticle, i.e., the particle has a characteristic dimension of less than about 1 micrometer, where the characteristic dimension of the particle is the diameter of a perfect sphere having the same volume as the particle. In other embodiments, larger sizes are possible (e.g., about 1-10 microns). A plurality of particles, in some embodiments, may also be characterized by an average size (e.g., an average largest cross-sectional dimension, or an average smallest cross-sectional dimension for the plurality of particles). A plurality of particles may have an average size of, for example, less than or equal to about 10 μm, less than or equal to about 5 μm, less than or equal to about 1 μm, less than or equal to about 800 nm, less than or equal to about 700 nm, less than or equal to about 500 nm, less than or equal to 400 nm, less than or equal to about 300 nm, less than or equal to about 200 nm, less than or equal to about 100 nm, less than or equal to about 75 nm, less than or equal to about 50 nm, less than or equal to about 40 nm, less than or equal to about 35 nm, less than or equal to about 30 nm, less than or equal to about 25 nm, less than or equal to about 20 nm, less than or equal to about 15 nm, or less than or equal to about 5 nm. In some cases, a plurality of particles may have an average size of, for example, at least about 5 nm, at least about 20 nm, at least about 50 nm, at least about 100 nm, at least about 200 nm, at least about 300 nm, at least about 400 nm, at least about 500 nm, at least about 1 μm, at least or at least about 5 μm. Combinations of the above-referenced ranges are also possible (e.g., an average size of at least about 50 nm and less than or equal to about 500 nm). Other ranges are also possible. In some embodiments, the sizes of the cores formed by a process described herein have a Gaussian-type distribution.

Pharmaceutical Agents

A particle or pharmaceutical composition of the invention may comprise at least one pharmaceutically acceptable crystalline form of Compound 3. In one embodiment, a particle or pharmaceutical composition comprises crystalline Form A. In another embodiment, a particle or pharmaceutical composition comprises crystalline Form B. The crystalline form of Compound 3 may be present in the core and/or one or more coatings of the particle (e.g., dispersed throughout the core and/or coating). In some embodiments, the crystalline form of Compound 3 may be disposed on the surface of the particle (e.g., on the outer or inner surface of the one or more coatings or on the surface of the core). The crystalline form of Compound 3 may be contained within the particle and/or disposed in a portion of the particle using commonly known techniques (e.g., coating, adsorption, covalent linkage, and encapsulation). In some embodiments, the crystalline form of Compound 3 is present during the formation of the core. In other embodiments, the crystalline form of Compound 3 is not present during the formation of the core. In certain embodiments, the crystalline form of Compound 3 is present during the coating of the core.

In some embodiments, the crystalline form of Compound 3 contained in a particle or pharmaceutical composition of the invention has a therapeutic and/or prophylactic effect in a mucosal tissue to be targeted. Non-limiting examples of mucosal tissues include ophthalmic, respiratory (e.g., including nasal, pharyngeal, tracheal, and bronchial membranes), oral (e.g., including the buccal and esophageal membranes and tonsil surface), gastrointestinal (e.g., including stomach, small intestine, large intestine, colon, rectum), nasal, and genital (e.g., including vaginal, cervical and urethral membranes) tissues.

Any suitable number of pharmaceutical agents may be present in a particle or pharmaceutical composition of the invention. For example, in addition to a crystalline form of Compound 3, at least 1, at least 2, at least 3, at least 4, at least 5, or more pharmaceutical agents may be present in the particle or pharmaceutical composition of the invention. In certain embodiments, less than 10 pharmaceutical agents are present in the particle or pharmaceutical composition of the invention.

In certain embodiments, the pharmaceutical agent in the particles or pharmaceutical compositions of the invention is a crystal form of Compound 3. In one embodiment, the pharmaceutical agent in the particles or pharmaceutical compositions of the invention is crystalline Form A of Compound 3. In another embodiment, the pharmaceutical agent in the particles or pharmaceutical compositions of the invention is crystalline Form B of Compound 3. The pharmaceutical agent described herein (e.g., a crystalline form of Compound 3) may be encapsulated in a polymer, a lipid, a protein, or a combination thereof.

Pharmaceutical Compositions

In another aspect, the present invention provides pharmaceutical compositions comprising at least one particle of the invention. Pharmaceutical compositions described herein and for use in accordance with the articles and methods described herein may include a pharmaceutically acceptable excipient or carrier. A pharmaceutically acceptable excipient or pharmaceutically acceptable carrier may include a non-toxic, inert solid, semi-solid or liquid filler, diluent, encapsulating material or formulation auxiliary of any suitable type. Some examples of materials which can serve as pharmaceutically acceptable carriers are sugars such as lactose, glucose, and sucrose; starches such as corn starch and potato starch; cellulose and its derivatives such as sodium carboxymethyl cellulose, ethyl cellulose, and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols such as propylene glycol; esters such as ethyl oleate and ethyl laurate; agar; detergents such as TWEEN 80; buffering agents such as magnesium hydroxide and aluminum hydroxide; alginic acid; pyrogen-free water; isotonic saline; Ringer's solution; ethyl alcohol; and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. As would be appreciated by one of skill in this art, the excipients may be chosen based on the route of administration as described below, the pharmaceutical agent being delivered, time course of delivery of the agent, etc.

Pharmaceutical compositions containing the particles described herein may be administered to a subject via any route known in the art. These include, but are not limited to, oral, sublingual, nasal, injection (e.g., intravenous, intradermal, subcutaneous, intramuscular), rectal, vaginal, intraarterial, intracisternally, intraperitoneal, intravitreal, periocular, topical (e.g., ocular or dermal, such as by powders, creams, ointments, or drops), buccal, and inhalational administration. In some embodiments, compositions described herein may be administered parenterally as injections (intravenous, intramuscular, or subcutaneous), drop infusion preparations, or suppositories. As would be appreciated by one of skill in this art, the route of administration and the effective dosage to achieve the desired biological effect may be determined by the agent being administered, the target organ, the preparation being administered, time course of administration, disease being treated, intended use, etc.

In certain embodiments, the pharmaceutical compositions are useful for the delivery of a crystalline form of Compound 3 described herein through or to mucus or a mucosal surface in a subject. The pharmaceutical compositions may be delivered to the mucosal surface in the subject and may pass through a mucosal barrier in the subject (e.g., mucus), and/or may show prolonged retention and/or increased uniform distribution of the particles of the invention at the mucosal surface, e.g., due to reduced mucoadhesion. In certain embodiments, the pharmaceutical compositions are useful in increasing the bioavailability of Compound 3 in the subject. In certain embodiments, the pharmaceutical compositions are useful in increasing the concentration of the Compound 3 in the subject. In certain embodiments, the pharmaceutical compositions are useful in increasing the exposure of Compound 3 in the subject. Moreover, the pharmaceutical compositions may be useful in treating and/or preventing a disease (e.g., ocular disease) in a subject.

Moreover, the pharmaceutical compositions may be administered parenterally as injections (intravenous, intramuscular, or subcutaneous), drop infusion preparations, or suppositories. For ophthalmic applications, the pharmaceutical compositions may be administered by injection (e.g., intraocular, conjunctival, subconjunctival, intrastromal, intravitreal, or intracameral), or by the local or ophthalmic mucous membrane route, the pharmaceutical compositions may be administered topically, such as solutions, suspensions (e.g., eye drops), gels, or ointments.

In some embodiments, particles described herein that may be administered in inhalant or aerosol formulations comprise one or more pharmaceutical agents, such as adjuvants, diagnostic agents, imaging agents, or therapeutic agents useful in inhalation therapy. The particle size of the particulate medicament should be such as to permit inhalation of substantially all of the medicament into the lungs upon administration of the aerosol formulation and may be, for example, less than about 20 microns, e.g., in the range of about 1 to about 10 microns, e.g., about 1 to about 5 microns, although other ranges are also possible. The particle size of the medicament may be reduced by conventional means, for example by milling or micronisation. Alternatively, the particulate medicament can be administered to the lungs via nebulization of a suspension. The final aerosol formulation may contain, for example, between 0.005-90% w/w, between 0.005-50%, between 0.005-10%, between about 0.005-5% w/w, or between 0.01-1.0% w/w, of medicament relative to the total weight of the formulation. Other ranges are also possible.

It is desirable, but by no means required, that the formulations described herein contain no components which may provoke the degradation of stratospheric ozone. In particular, in some embodiments, propellants are selected that do not contain or do not consist essentially of chlorofluorocarbons such as $CCl_3F$, $CCl_2F_2$, and $CF_3CCl_3$.

The aerosol may comprise propellant. The propellant may optionally contain an adjuvant having a higher polarity and/or a higher boiling point than the propellant. Polar adjuvants which may be used include (e.g., $C_{2-6}$) aliphatic alcohols and polyols such as ethanol, isopropanol, and propylene glycol, preferably ethanol. In general, only small quantities of polar adjuvants (e.g., 0.05-3.0% w/w) may be required to improve the stability of the dispersion—the use of quantities in excess of 5% w/w may tend to dissolve the medicament. Formulations in accordance with the embodiments described herein may contain less than 1% w/w, e.g., about 0.1% w/w, of polar adjuvant. However, the formulations described herein may be substantially free of polar adjuvants, especially ethanol. Suitable volatile adjuvants include saturated hydrocarbons such as propane, n-butane, isobutane, pentane and isopentane and alkyl ethers such as dimethyl ether. In general, up to 50% w/w of the propellant may comprise a volatile adjuvant, for example, up to 30% w/w of a volatile saturated $C_1$-$C_6$ hydrocarbon. Optionally, the aerosol formulations according to the invention may further comprise one or more surfactants. The surfactants can be physiologically acceptable upon administration by inhalation. Within this category are included surfactants such as L-α-phosphatidylcholine (PC), 1,2-dipalmitoylphosphatidycholine (DPPC), oleic acid, sorbitan trioleate, sorbitan mono-oleate, sorbitan monolaurate, polyoxyethylene sorbitan monolaurate, polyoxyethylene sorbitan monooleate, natural lecithin, oleyl polyoxyethylene ether, stearyl polyoxyethylene ether, lauryl polyoxyethylene ether, block copolymers of oxyethylene and oxypropylene, synthetic lecithin, diethylene glycol dioleate, tetrahydrofurfuryl oleate, ethyl oleate, isopropyl myristate, glyceryl monooleate, glyceryl monostearate, glyceryl monoricinoleate, cetyl alcohol, stearyl alcohol, polyethylene glycol 400, cetyl pyridinium chloride, benzalkonium chloride, olive oil, glyceryl monolaurate, corn oil, cotton seed oil, and sunflower seed oil.

The formulations described herein may be prepared by dispersal of the particles in the selected propellant and/or co-propellant in an appropriate container, e.g., with the aid of sonication. The particles may be suspended in co-propellant and filled into a suitable container. The valve of the container is then sealed into place and the propellant introduced by pressure filling through the valve in the conventional manner. The particles may be thus suspended or dissolved in a liquefied propellant, sealed in a container with a metering valve and fitted into an actuator. Such metered dose inhalers are well known in the art. The metering valve may meter 10 to 500 μL and preferably 25 to 150 μL. In certain embodiments, dispersal may be achieved using dry powder inhalers (e.g., spinhaler) for the particles (which remain as dry powders). In other embodiments, nanospheres, may be suspended in an aqueous fluid and nebulized into fine droplets to be aerosolized into the lungs.

Sonic nebulizers may be used because they minimize exposing the agent to shear, which may result in degradation of the particles. Ordinarily, an aqueous aerosol is made by formulating an aqueous solution or suspension of the particles together with conventional pharmaceutically acceptable carriers and stabilizers. The carriers and stabilizers vary with the requirements of the particular composition, but typically include non-ionic surfactants (TWEENS, PLURONIC®, or polyethylene glycol), innocuous proteins like serum albumin, sorbitan esters, oleic acid, lecithin, amino acids such as glycine, buffers, salts, sugars, or sugar alcohols. Aerosols generally are prepared from isotonic solutions.

The compositions and/or formulations described herein may have any suitable osmolarity. In some embodiments, a composition and/or formulation described herein may have an osmolarity of at least about 0 mOsm/L, at least about 5 mOsm/L, at least about 25 mOsm/L, at least about 50 mOsm/L, at least about 75 mOsm/L, at least about 100 mOsm/L, at least about 150 mOsm/L, at least about 200 mOsm/L, at least about 250 mOsm/L, or at least about 310 mOsm/L. In certain embodiments, a composition and/or formulation described herein may have an osmolarity of less than or equal to about 310 mOsm/L, less than or equal to about 250 mOsm/L, less than or equal to about 200 mOsm/L, less than or equal to about 150 mOsm/L, less than or equal to about 100 mOsm/L, less than or equal to about 75 mOsm/L, less than or equal to about 50 mOsm/L, less than or equal to about 25 mOsm/L, or less than or equal to about 5 mOsm/L. Combinations of the above-referenced ranges are also possible (e.g., an osmolarity of at least about 0 mOsm/L and less than or equal to about 50 mOsm/L). Other ranges are also possible. The osmolarity of the composition and/or formulation can be varied by changing, for example, the concentration of salts present in the solvent of the composition and/or formulation.

The pharmaceutical composition of the invention may include one or more pharmaceutical agents described herein, such as a crystalline form of Compound 3. In certain embodiments, the pharmaceutical composition includes a plurality of particles of the invention that comprise one or more pharmaceutical agents in the core and/or coating of the particles. In some embodiments, the ratio of surface-altering agent to pharmaceutical agent (or salt thereof) may be at least 0.001:1 (weight ratio, molar ratio, or w:v ratio), at least 0.01:1, at least 0.01:1, at least 1:1, at least 2:1, at least 3:1, at least 5:1, at least 10:1, at least 25:1, at least 50:1, at least 100:1, or at least 500:1. In some cases, the ratio of surface-altering agent to pharmaceutical agent (or salt thereof) may be less than or equal to 1000:1 (weight ratio or molar ratio), less than or equal to 500:1, less than or equal to 100:1, less than or equal to 75:1, less than or equal to 50:1, less than or equal to 25:1, less than or equal to 10:1, less than or equal to 5:1, less than or equal to 3:1, less than or equal to 2:1, less than or equal to 1:1, or less than or equal to 0.1:1. Combinations of the above-referenced ranges are possible (e.g., a ratio of at least 5:1 and less than or equal to 50:1). Other ranges are also possible. In some embodiments, the pharmaceutical composition of the invention includes the above-noted ranges for the ratio of the weight of each one of the pharmaceutical agents to the weight of each one of the one or more surface-altering agents during a formation process and/or a dilution process described herein. In certain embodiments, the pharmaceutical composition includes the above-noted ranges for the ratio of the weight of each one of the pharmaceutical agents to the weight of each one of the one or more surface-altering agents immediately prior to the pharmaceutical composition being administered to a subject or contacted with a biological sample. The pharmaceutical agent may be present in the pharmaceutical composition of the invention in any suitable amount, e.g., at least about 0.01 wt %, at least about 0.1 wt %, at least about 1 wt %, at least about 5 wt %, at least about 10 wt %, at least about 30 wt % of the pharmaceutical composition. In some cases, the pharmaceutical agent may be present in the pharmaceutical composition at less than about 30 wt %, less than about 10 wt %, less than about 5 wt %, less than about 2 wt %, or less than about 1 wt % of the pharmaceutical composition. Combinations of the above-referenced ranges are also possible (e.g., present in an amount of at least about 0.1 wt % and less than about 10 wt % of the pharmaceutical composition). Other ranges are also possible. In certain embodiments, the pharmaceutical agent is about 0.1-2 wt % of the pharmaceutical composition. In certain embodiments, the pharmaceutical agent is about 2-20 wt % of the pharmaceutical composition. In certain embodiments, the pharmaceutical agent is about 0.2 wt %, about 0.4 wt %, about 1 wt %, about 2 wt %, about 5 wt %, or about 10 wt % of the pharmaceutical composition.

In one set of embodiments, a composition and/or formulation includes one or more chelating agents. A chelating agent used herein refers to a chemical compound that has the ability to react with a metal ion to form a complex through one or more bonds. The one or more bonds are typically ionic or coordination bonds. The chelating agent can be an inorganic or an organic compound. A metal ion capable of catalyzing certain chemical reactions (e.g., oxidation reactions) may lose its catalytic activity when the metal ion is bound to a chelating agent to form a complex. Therefore, a chelating agent may show preservative properties when it binds to a metal ion. Any suitable chelating agent that has preservative properties can be used, such as phosphonic acids, aminocarboxylic acids, hydroxycarboxylic acids, polyamines, aminoalcohols, and polymeric chelating agents. Specific examples of chelating agents include, but are not limited to, ethylenediaminetetraacetic acid (EDTA), nitrilotriacetic acid (NTA), diethylenetriaminepentacetic acid (DTPA), N-hydroxyethylethylene diaminetriacetic acid (HEDTA), tetraborates, triethylamine diamine, and salts and derivatives thereof. In certain embodiments, the chelating agent is EDTA. In certain embodiments, the chelating agent is a salt of EDTA. In certain embodiments, the chelating agent is disodium EDTA.

In certain embodiments, the pharmaceutical composition includes a plurality of particles of the invention that comprise the chelating agent in the formulation containing the particles. In certain embodiments, the concentration of the chelating agent is greater than or equal to about 0 wt %, greater than or equal to about 0.0001 wt %, greater than or equal to about 0.003 wt %, greater than or equal to about 0.01 wt %, greater than or equal to about 0.03 wt %, greater than or equal to about 0.05 wt %, greater than or equal to about 0.1 wt %, greater than or equal to about 0.3 wt %, greater than or equal to about 1 wt %, or greater than or equal to about 3 wt %. In certain embodiments, the concentration of the chelating agent is less than or equal to about 3 wt %, less than or equal to about 1 wt %, less than or equal to about 0.3 wt %, less than or equal to about 0.1 wt %, less than or equal to about 0.05 wt %, less than or equal to about 0.03 wt %, less than or equal to about 0.01 wt %, less than or equal to about 0.003 wt %, less than or equal to about 0.001 wt %, or less than or equal to about 0.0003 wt %. Combinations of the above-noted ranges are possible (e.g., a concentration of greater than or equal to about 0.01 wt % and less than or equal to about 0.3 wt %). Other ranges are also possible. In certain embodiments, the concentration of the chelating agent is about 0.001-0.1 wt %. In certain embodiments, the concentration of the chelating agent is about 0.005 wt %. In certain embodiments, the concentration of the chelating agent is about 0.01 wt %. In certain embodiments, the concentration of the chelating agent is about 0.05 wt %. In certain embodiments, the concentration of the chelating agent is about 0.1 wt %.

In some embodiments, an antimicrobial agent may be included in a composition and/or formulation including the coated particles described herein. An antimicrobial agent used herein refers to a bioactive agent effective in the inhibition of, prevention of, or protection against microorganisms such as bacteria, microbes, fungi, viruses, spores, yeasts, molds, and others generally associated with infections. Examples of antimicrobial agents include cephalosporins, clindamycin, chloramphenicol, carbapenems, minocyclines, rifampin, penicillins, monobactams, quinolones, tetracycline, macrolides, sulfa antibiotics, trimethoprim, fusidic acid, aminoglycosides, amphotericin B, azoles, flucytosine, cilofungin, bactericidal nitrofuran compounds, nanoparticles of metallic silver or an alloy of silver containing about 2.5 wt % copper, silver citrate, silver acetate, silver benzoate, bismuth pyrithione, zinc pyrithione, zinc percarbonates, zinc perborates, bismuth salts, parabens (e.g., methyl-, ethyl-, propyl-, butyl-, and octyl-benzoic acid esters), citric acid, benzalkonium chloride (BAC), rifamycin, and sodium percarbonate.

In certain embodiments, the pharmaceutical composition includes a plurality of particles of the invention that comprise the antimicrobial agent in the formulation containing the particles. In certain embodiments, the concentration of the antimicrobial agent may be greater than or equal to about 0 wt %, greater than or equal to about 0.0001 wt %, greater than or equal to about 0.003 wt %, greater than or equal to about 0.01 wt %, greater than or equal to about 0.03 wt %, greater than or equal to about 0.1 wt %, greater than or equal to about 0.3 wt %, greater than or equal to about 1 wt %, or greater than or equal to about 3 wt %. In certain embodiments, the concentration of the antimicrobial agent may be less than or equal to about 3 wt %, less than or equal to about 1 wt %, less than or equal to about 0.3 wt %, less than or equal to about 0.1 wt %, less than or equal to about 0.03 wt %, less than or equal to about 0.01 wt %, less than or equal to about 0.003 wt %, less than or equal to about 0.001 wt %, or less than or equal to about 0.0003 wt %. Combinations of the above-noted ranges are possible (e.g., a concentration of greater than or equal to about 0.001 wt % and less than or equal to about 0.1 wt %). Other ranges are also possible. In certain embodiments, the concentration of the antimicrobial agent is about 0.001-0.05 wt %. In certain embodiments, the concentration of the antimicrobial agent is about 0.002 wt %. In certain embodiments, the concentration of the antimicrobial agent is about 0.005 wt %. In certain embodiments, the concentration of the antimicrobial agent is about 0.01 wt %. In certain embodiments, the concentration of the antimicrobial agent is about 0.02 wt %. In certain embodiments, the concentration of the antimicrobial agent is about 0.05 wt %.

In some embodiments, a tonicity agent may be included in a composition and/or formulation including the coated particles described herein. A tonicity agent used herein refers to a compound or substance that can be used to adjust the composition of a formulation to the desired osmolarity range. In certain embodiments, the desired osmolarity range is an isotonic range compatible with blood. In certain embodiments, the desired osmolarity range is hypotonic. In certain embodiments, the desired osmolarity range is hypertonic. Examples of tonicity agents include glycerin, lactose, mannitol, dextrose, sodium chloride, sodium sulfate, sorbitol, saline-sodium citrate (SSC), and the like. In certain embodiments, a combination of one or more tonicity agents may be used. In certain embodiments, the tonicity agent is glycerin. In certain embodiments, the tonicity agent is sodium chloride.

A tonicity agent (such as one described herein) may be present at a suitable concentration in a composition and/or formulation including the coated particles described herein. In certain embodiments, the concentration of the tonicity agent is greater than or equal to about 0 wt %, greater than or equal to about 0.001 wt %, greater than or equal to about 0.03 wt %, greater than or equal to about 0.1 wt %, greater than or equal to about 0.3 wt %, greater than or equal to about 1 wt %, greater than or equal to about 3 wt %, greater than or equal to about 10 wt %, greater than or equal to about 20 wt %, or greater than or equal to about 30 wt %. In certain embodiments, the concentration of the tonicity agent is less than or equal to about 30 wt %, less than or equal to about 10 wt %, less than or equal to about 3 wt %, less than or equal to about 1 wt %, less than or equal to about 0.3 wt %, less than or equal to about 0.1 wt %, less than or equal to about 0.03 wt %, less than or equal to about 0.01 wt %, or less than or equal to about 0.003 wt %. Combinations of the above-noted ranges are possible (e.g., a concentration of greater than or equal to about 0.1 wt % and less than or equal to about 10 wt %). Other ranges are also possible. In certain embodiments, the concentration of the tonicity agent is about 0.1-1%. In certain embodiments, the concentration of the tonicity agent is about 0.5-3%. In certain embodiments, the concentration of the tonicity agent is about 0.25 wt %. In certain embodiments, the concentration of the tonicity agent is about 0.45 wt %. In certain embodiments, the concentration of the tonicity agent is about 0.9 wt %. In certain embodiments, the concentration of the tonicity agent is about 1.2 wt %. In certain embodiments, the concentration of the tonicity agent is about 2.4 wt %. In certain embodiments, the concentration of the tonicity agent is about 5 wt %.

In some embodiments, a composition and/or formulation described herein may have an osmolarity of at least about 0 mOsm/L, at least about 5 mOsm/L, at least about 25 mOsm/L, at least about 50 mOsm/L, at least about 75 mOsm/L, at least about 100 mOsm/L, at least about 150 mOsm/L, at least about 200 mOsm/L, at least about 250 mOsm/L, at least about 310 mOsm/L, or at least about 450 mOsm/L. In certain embodiments, a composition and/or formulation described herein may have an osmolarity of less than or equal to about 450 mOsm/L, less than or equal to about 310 mOsm/L, less than or equal to about 250 mOsm/L, less than or equal to about 200 mOsm/L, less than or equal to about 150 mOsm/L, less than or equal to about 100 mOsm/L, less than or equal to about 75 mOsm/L, less than or equal to about 50 mOsm/L, less than or equal to about 25 mOsm/L, or less than or equal to about 5 mOsm/L. Combinations of the above-referenced ranges are also possible (e.g., an osmolarity of at least about 0 mOsm/L and less than or equal to about 50 mOsm/L). Other ranges are also possible.

It is appreciated in the art that the ionic strength of an inventive pharmaceutical composition that comprises a plurality of particles of the invention may affect the polydispersity of the plurality of the particles. The ionic strength may also affect the colloidal stability of the plurality of the particles. For example, a relatively high ionic strength of the pharmaceutical composition may cause the plurality of particles to coagulate and therefore may destabilize the pharmaceutical composition. In some embodiments, the pharmaceutical composition is stabilized by repulsive inter-particle forces. For example, the plurality of particles may be electrically or electrostatically charged. Two charged particles may repel each other, preventing collision and aggregation. When the repulsive inter-particle forces weaken or become attractive, the plurality of particles may start to aggregate. For instance, when the ionic strength of the pharmaceutical composition is increased to a certain level, the charges (e.g., negative charges) of the plurality of particles may be neutralized by the oppositely charged ions present in the pharmaceutical composition (e.g., $Na^+$ ions in solution). As a result, the plurality of particles may collide and bond to each other to form aggregates (e.g., clusters or flocs) of larger sizes. The formed aggregates of particles may also differ in size, and thus the polydispersity of the pharmaceutical composition may also increase. For example, an inventive pharmaceutical composition comprising similarly-sized particles may become a pharmaceutical composition comprising particles having various sizes (e.g., due to aggregation) when the ionic strength of the pharmaceutical composition is increased beyond a certain level. In the course of aggregation, the aggregates may grow in size and eventually settle to the bottom of the container, and the pharmaceutical composition is considered colloidally unstable. Once the plurality of particles in a pharmaceutical composition form aggregates, it is usually difficult to disrupt the aggregates into individual particles.

Certain pharmaceutical compositions of the invention show unexpected properties in that, among other things, the presence of one or more ionic tonicity agents (e.g., a salt, such as NaCl) in the pharmaceutical compositions at certain concentrations actually decreases or maintains the degree of aggregation of the particles present in the pharmaceutical compositions, and/or does not significantly increase aggregation. In certain embodiments, the polydispersity of the pharmaceutical composition decreases, is relatively constant, or does not change by an appreciable amount upon addition of one or more ionic tonicity agents into the pharmaceutical composition. For example, in some embodiments, the polydispersity of a pharmaceutical composition is relatively constant in the presence of added ionic strength and/or when the added ionic strength of the pharmaceutical composition is kept relatively constant or increased (e.g., during a formation and/or dilution process described herein). In certain embodiments, when the ionic strength increases by at least 50%, the polydispersity increases by less than about 300%, less than about 100%, less than about 30%, less than about 10%, less than about 3%, or less than about 1%. In certain embodiments, when the ionic strength is increased by at least 50%, the polydispersity increases by greater than or equal to about 1%, greater than or equal to about 3%, greater than or equal to about 10%, greater than or equal to about 30%, or greater than or equal to about 100%. Combinations of the above-noted ranges are possible (e.g., an increase in polydispersity of less than 30% and greater than or equal to 3%). Other ranges are also possible.

The ionic strength of a pharmaceutical composition of the invention may be controlled (e.g., increased, decreased, or maintained) through a variety of means, such as the addition of one or more ionic tonicity agents (e.g., a salt, such as NaCl) to the pharmaceutical composition. In certain embodiments, the ionic strength of a pharmaceutical composition of the invention is greater than or equal to about 0.0003 M, greater than or equal to about 0.001 M, greater than or equal to about 0.003 M, greater than or equal to about 0.01 M, greater than or equal to about 0.03 M, greater than or equal to about 0.1 M, greater than or equal to about 0.3 M, greater than or equal to about 1 M, greater than or equal to about 3 M, or greater than or equal to about 10 M. In certain embodiments, the ionic strength of a pharmaceutical composition of the invention is less than about 10 M, less than about 3 M, less than about 1 M, less than about 0.3 M, less than about 0.1 M, less than about 0.03 M, less than about 0.01 M, less than about 0.003 M, less than about 0.001 M, or less than about 0.0003 M. Combinations of the above-noted ranges are possible (e.g., an ionic strength of greater than or equal to about 0.01 M and less than about 1 M). Other ranges are also possible. In certain embodiments, the ionic strength of a pharmaceutical composition of the invention is about 0.1 M, about 0.15 M, or about 0.3 M.

In certain embodiments, the polydispersity of a pharmaceutical composition does not change upon addition of one or more ionic tonicity agents into the pharmaceutical composition. In certain embodiments, the polydispersity does not significantly increase upon addition of one or more ionic tonicity agents into the pharmaceutical composition. In certain embodiments, the polydispersity increases to a level described herein upon addition of one or more ionic tonicity agents into the pharmaceutical composition.

The polydispersity of an inventive pharmaceutical composition that comprises a plurality of particles of the invention may be measured by the polydispersity index (PDI). In certain embodiments, the PDI of the pharmaceutical composition is less than about 1, less than about 0.8, less than about 0.6, less than about 0.4, less than about 0.3, less than about 0.2, less than about 0.15, less than about 0.1, less than about 0.05, less than about 0.01, or less than about 0.005. In certain embodiments, the PDI of the pharmaceutical composition is greater than or equal to about 0.005, greater than or equal to about 0.01, greater than or equal to about 0.05, greater than or equal to about 0.1, greater than or equal to about 0.15, greater than or equal to about 0.2, greater than or equal to about 0.3, greater than or equal to about 0.4, greater than or equal to about 0.6, greater than or equal to about 0.8, or greater than or equal to about 1. Combinations of the above-noted ranges are possible (e.g., a PDI of greater than or equal to about 0.1 and less than about 0.5). Other ranges are also possible. In certain embodiments, the PDI of the pharmaceutical composition is about 0.1, about 0.15, or about 0.2. In certain embodiments, the pharmaceutical composition is highly dispersible and does not tend to form aggregates. Even when the particles do form aggregates, the aggregates may be easily broken up into individual particles without rigorously agitating the pharmaceutical composition.

For example, in some embodiments, the polydispersity of a composition and/or formulation is relatively constant in the presence of added ionic strength and/or when the added ionic strength of the composition and/or formulation is kept relatively constant or increased (e.g., during a formation and/or dilution process). In certain embodiments, when the ionic strength increases by at least 50%, the polydispersity increases by less than or equal to about 200%, less than or equal to about 150%, less than or equal to about 100%, less than or equal to about 75%, less than or equal to about 50%, less than or equal to about 30%, less than or equal to about 20%, less than or equal to about 10%, less than or equal to about 3%, or less than or equal to about 1%. In certain embodiments, when the ionic strength is increased by at least 50%, the polydispersity increases by greater than or equal to about 1%, greater than or equal to about 3%, greater than or equal to about 10%, greater than or equal to about 30%, or greater than or equal to about 100%. Combinations of the above-noted ranges are possible (e.g., an increase in polydispersity of less than or equal to 50% and greater than or equal to 1%). Other ranges are also possible.

The ionic strength of a formulation described herein may be controlled (e.g., increased) through a variety of means, such as the addition of one or more ionic tonicity agents (e.g., a salt such as NaCl) to the formulation. In certain embodiments, the ionic strength of a formulation described herein is greater than or equal to about 0.0005 M, greater than or equal to about 0.001 M, greater than or equal to about 0.003 M, greater than or equal to about 0.01 M, greater than or equal to about 0.03 M, greater than or equal to about 0.1 M, greater than or equal to about 0.3 M, greater than or equal to about 1 M, greater than or equal to about 3 M, or greater than or equal to about 10 M. In certain embodiments, the ionic strength of a formulation described herein is less than or equal to about 10 M, less than or equal to about 3 M, less than or equal to about 1 M, less than or equal to about 0.3 M, less than or equal to about 0.1 M, less than or equal to about 0.03 M, less than or equal to about 0.01 M, less than or equal to about 0.003 M, less than or equal to about 0.001 M, or less than or equal to about 0.0005 M. Combinations of the above-noted ranges are possible (e.g., an ionic strength of greater than or equal to about 0.01 M and less than or equal to about 1 M). Other ranges are also possible. In certain embodiments, the ionic strength of a formulation described herein is about 0.1 M. In certain embodiments, the ionic strength of a formulation described herein is about 0.15 M. In certain embodiments, the ionic strength of a formulation described herein is about 0.3 M.

Generally, it is desired that a formulation is sterile before or upon administration to a subject. A sterile formulation is essentially free of pathogenic microorganisms, such as bacteria, microbes, fungi, viruses, spores, yeasts, molds, and others generally associated with infections. In some embodiments, compositions and/or formulations including the coated particles described herein may be subject to an aseptic process and/or other sterilization process. An aseptic process typically involves sterilizing the components of a formulation, final formulation, and/or container closure of a drug product through a process such as heat, gamma irradiation, ethylene oxide, or filtration and then combining in a sterile environment. In some cases, an aseptic process is preferred. In other embodiments, terminal sterilization is preferred.

Examples of other sterilization methods include radiation sterilization (e.g., gamma, electron, or x-ray radiation), heat sterilization, sterile filtration, and ethylene oxide sterilization. The terms "radiation" and "irradiation" are used herein interchangeably. Unlike other sterilization methods, radiation sterilization has the advantage of high penetrating ability and instantaneous effects, without the need to control temperature, pressure, vacuum, or humidity in some instances. In certain embodiments, the radiation used to sterilize the coated particles described herein is gamma radiation. Gamma radiation may be applied in an amount sufficient to kill most or substantially all of the microbes in or on the coated particles. The temperature of the coated particles described herein and the rate of radiation may be relatively constant during the entire gamma radiation period. Gamma irradiation may be performed at any suitable temperature (e.g., ambient temperature, about 40° C., between about 30 to about 50° C.). Unless otherwise indicated, measurements of gamma irradiation described herein refer to ones performed at about 40° C.

In embodiments in which a sterilization process is used, it may be desired that the process does not: (1) significantly change the particle size of the coated particles described herein; (2) significantly change the integrity of the active ingredient (such as a drug) of the coated particles described herein; and (3) generate unacceptable concentrations of impurities during or following the process. In certain embodiments, the impurities generated during or following the process are degradants of the active ingredient of the coated particles described herein.

In certain embodiments, a process used to sterilize a composition and/or formulation described herein results in the presence of one or more degradants in the formulation at less than or equal to about 10 wt % (relative to the weight of the undegraded drug), less than or equal to about 3 wt %, less than or equal to about 2 wt %, less than or equal to about 1.5 wt %, less than or equal to about 1 wt %, less than or equal to about 0.9 wt %, less than or equal to about 0.8 wt %, less than or equal to about 0.7 wt %, less than or equal to about 0.6 wt %, less than or equal to about 0.5 wt %, less than or equal to about 0.4 wt %, less than or equal to about 0.3 wt %, less than or equal to about 0.2 wt %, less than or equal to about 0.15 wt %, less than or equal to about 0.1 wt %, less than or equal to about 0.03 wt %, less than or equal to about 0.01 wt %, less than or equal to about 0.003 wt %, or less than or equal to about 0.001 wt %. In some embodiments, the process results in a degradant in the formulation at greater than or equal to about 0.001 wt %, greater than or equal to about 0.003 wt %, greater than or equal to about 0.01 wt %, greater than or equal to about 0.03 wt %, greater than or equal to about 0.1 wt %, greater than or equal to about 0.3 wt %, greater than or equal to about 1 wt %, greater than or equal to about 3 wt %, or greater than or equal to about 10 wt %. Combinations of the above-referenced ranges are also possible (e.g., less than or equal to about 1 wt % and greater than or equal to about 0.01 wt %). Other ranges are also possible.

When gamma irradiation is used in a sterilization process, the cumulative amount of the gamma radiation used may vary. In certain embodiments, the cumulative amount of the gamma radiation is greater than or equal to about 0.1 kGy, greater than or equal to about 0.3 kGy, greater than or equal to about 1 kGy, greater than or equal to about 3 kGy, greater than or equal to about 10 kGy, greater than or equal to about 30 kGy, greater than or equal to about 100 kGy, or greater than or equal to about 300 kGy. In certain embodiments, the cumulative amount of the gamma radiation is less than or equal to about 0.1 kGy, less than or equal to about 0.3 kGy, less than or equal to about 1 kGy, less than or equal to about 3 kGy, less than or equal to about 10 kGy, less than or equal to about 30 kGy, less than or equal to about 100 kGy, or less than or equal to about 300 kGy. Combinations of the above-noted ranges are possible (e.g., greater than or equal to about 1 kGy and less than or equal to about 30 kGy). Other ranges are also possible. In certain embodiments, multiple doses of radiation are utilized to achieve a desired cumulative radiation dosage.

The compositions and/or formulations described herein may have any suitable pH values. The term "pH," unless otherwise provided, refers to pH measured at ambient temperature (e.g., about 20° C., about 23° C., or about 25° C.). The compositions and/or formulations have, for example, an acidic pH, a neutral pH, or a basic pH and may depend on, for example, where the compositions and/or formulations are to be delivered in the body. In certain embodiments, the compositions and/or formulations have a physiological pH. In certain embodiments, the pH value of the compositions and/or formulations is at least about 1, at least about 2, at least about 3, at least about 4, at least about 5, at least about 6, at least about 6.2, at least about 6.4, at least about 6.6, at least about 6.8, at least about 7, at least about 7.2, at least about 7.4, at least about 7.6, at least about 7.8, at least about 8, at least about 8.2, at least about 8.4, at least about 8.6, at least about 8.8, at least about 9, at least about 10, at least about 11, or at least about 12. In certain embodiments, the pH value of the compositions and/or formulations is less than or equal to about 12, less than or equal to about 11, less than or equal to about 10, less than or equal to about 9, less than or equal to about 8.8, less than or equal to about 8.6, less than or equal to about 8.4, less than or equal to about 8.2, less than or equal to about 8, less than or equal to about 7.8, less than or equal to about 7.6, less than or equal to about 7.4, less than or equal to about 7.2, less than or equal to about 7, less than or equal to about 6.8, less than or equal to about 6.6, less than or equal to about 6.4, less than or equal to about 6.2, less than or equal to about 6, less than or equal to about 5, less than or equal to about 4, less than or equal to about 3, less than or equal to about 2, or less than or equal to about 1. Combinations of the above-noted ranges are possible (e.g., a pH value of at least about 5 and less than or equal to about 8.2). Other ranges are also possible. In certain embodiments, the pH value of the compositions and/or formulations described herein is at least about 5 and less than or equal to about 8.

In some embodiments, the particles, compositions, and/or formulations described herein increase the ocular bioavailability of Compound 3 by at least about 10%, at least about 20%, at least about 30%, at least about 40%, at least about 50%, at least about 60%, at least about 70%, at least about 80%, at least about 90%, at least about 100%, at least about 150%, at least about 200%, at least about 5 fold, at least about 10 fold, at least about 20 fold, at least about 50 fold, at least about 100 fold, at least about 500 fold, or at least about 1000 fold. In certain embodiments the particles, compositions, and/or formulations described herein increase the ocular bioavailability of Compound 3 by less than or equal to about 1000 fold, less than or equal to about 500 fold, less than or equal to about 100 fold, less than or equal to about 50 fold, less than or equal to about 20 fold, less than or equal to about 10 fold, less than or equal to about 5 fold, less than or equal to about 200%, less than or equal to about 150%, less than or equal to about 100%, less than or equal to about 90%, less than or equal to about 80%, less than or equal to about 70%, less than or equal to about 60%, less than or equal to about 50%, less than or equal to about 40%, less than or equal to about 30%, less than or equal to about 20%, or less than or equal to about 10%. Combinations of the above-referenced ranges are also possible (e.g., an increase of at least about 10% and less than or equal to about 10 fold). Other ranges are also possible. In some instances, the AUC of Compound 3 increases at a tissue and/or fluid in the front of the eye. In other instances, the AUC of Compound 3 increases at a tissue and/or fluid in the back of the eye.

In general, an increase in ocular bioavailability may be calculated by taking the difference in the AUC measured in an ocular tissue of interest (e.g., in aqueous humor) between those of a test composition and a control composition, and dividing the difference by the bioavailability of the control composition. A test composition may include particles comprising a crystalline form of Compound 3, and the particles may be characterized as being mucus penetrating (e.g., having a relative velocity in mucus of greater than about 0.5, or another other relative velocity described herein). A control composition may include particles comprising the same crystalline form of Compound 3 as that present in the test composition, the particles having a substantially similar size as those of the test composition, but which are not mucus penetrating (e.g., having a relative velocity in mucus of less than or equal to about 0.5, or another other relative velocity described herein).

Ocular bioavailability of Compound 3 may be measured in an appropriate animal model (e.g. in a New Zealand white rabbit model, or a Gottingen mini-pig model). The concentration of Compound 3 and, when appropriate, its metabolite(s), in appropriate ocular tissues or fluids is measured as a function of time after administration. Other methods of measuring ocular bioavailability of Compound 3 are possible.

In some embodiments, the concentration of Compound 3 in an ocular tissue and/or fluid may be increased when the crystalline form of Compound 3 is delivered (e.g., via topical administration to the eye) using the particles, compositions, and/or formulations described herein compared to when the crystalline form of Compound 3 is delivered using certain existing particles, compositions, and/or formulations that contain the same the crystalline form of Compound 3 (or compared to the delivery of the same crystalline form of Compound 3 (e.g., of similar size) as the coated particle in question, but which does not include the coating). In certain embodiments, a dose of the particles, compositions, and/or formulations is administered, followed by the measurement of the concentration of the crystalline form of Compound 3 in a tissue and/or fluid of the eye. For purposes of comparison, the amount of the crystalline form of Compound 3 included in the administered dose of the particles, compositions, and/or formulations described herein may be similar or substantially equal to the amount of the crystalline form of Compound 3 included in the administered dose of the existing particles, compositions, and/or formulations. In certain embodiments, the concentration of Compound 3 in a tissue and/or fluid of the eye is measured at a certain time subsequent to the administration ("time post-dose") of a dose of the particles, compositions, and/or formulations described herein or of the existing particles, compositions, and/or formulations. In certain embodiments, the time when the concentration is measured is about 1 min, about 10 min, about 30 min, about 1 h, about 2 h, about 3 h, about 4 h, about 5 h, about 6 h, about 7 h, about 8 h, about 9 h, about 10 h, about 11 h, about 12 h, about 18 h, about 24 h, about 36 h, or about 48 h, post-dose.

In some embodiments, the concentration of Compound 3 in a tissue and/or fluid may increase due to, at least in part, a coating on core particles comprising the crystalline form of Compound 3 that renders the particles mucus penetrating, compared to particles of the same crystalline form of Compound 3 (e.g., of similar size) as the coated particle in question, but which does not include the coating. In some embodiments, the particles, compositions, and/or formulations described herein increases the concentration of Compound 3 in a tissue and/or fluid by at least about 10%, at least about 20%, at least about 30%, at least about 40%, at least about 50%, at least about 60%, at least about 70%, at least about 80%, at least about 90%, at least about 100%, at least about 200%, at least about 300%, at least about 400%, at least about 500%, or at least about 10 fold, at least about 20 fold, at least about 50 fold, at least about 100 fold, at least about 1000 fold, at least about $10^4$ fold, at least about $10^5$ fold, or at least about $10^6$ fold. In some cases, the particles, compositions, and/or formulations described herein increases the concentration of Compound 3 in a tissue and/or fluid by less than or equal to about $10^6$ fold, less than or equal to about $10^5$ fold, less than or equal to about $10^4$ fold, 1000 fold, less than or equal to about 100 fold, less than or equal to about 10 fold, less than or equal to about 500%, less than or equal to about 400%, less than or equal to about 300%, less than or equal to about 200%, less than or equal to about 100%, less than or equal to about 90%, less than or equal to about 80%, less than or equal to about 70%, less than or equal to about 60%, less than or equal to about 50%, less than or equal to about 40%, less than or equal to about 30%, less than or equal to about 20%, or less than or equal to about 10%. Combinations of the above-referenced ranges are also possible (e.g., an increase of greater than or equal to about 10% and less than or equal to about 90%). Other ranges are also possible. In some instances, the concentration of Compound 3 increases at a tissue and/or fluid in the front of the eye. In other instances, the concentration of Compound 3 increases at a tissue and/or fluid in the back of the eye.

The ocular concentration of Compound 3, and, when appropriate, its metabolite(s), in appropriate ocular fluids or tissues may be measured as a function of time in vivo using an appropriate animal model. One method of determining the ocular concentration of Compound 3 involves dissecting of the eye to isolate tissues of interest (e.g., in an animal model comparable to the subject). The concentration of Compound 3 in the tissues of interest is then determined by HPLC or LC/MS analysis.

In certain embodiments, the period of time between administration of the particles described herein and obtaining a sample for measurement of concentration or AUC is less than about 1 hour, less than or equal to about 2 hours, less than or equal to about 3 hours, less than or equal to about 4 hours, less than or equal to about 6 hours, less than or equal to about 12 hours, less than or equal to about 36 hours, or less than or equal to about 48 hours. In certain embodiments, the period of time is at least about 1 hour, at least about 2 hours, at least about 3 hours, at least about 4 hours, at least about 6 hours, at least about 8 hours, at least about 12 hours, at least about 36 hours, or at least about 48 hours. Combinations of the above-referenced ranges are also possible (e.g., a period of time between consecutive doses of greater than or equal to about 3 hours and less than or equal to about 12 hours). Other ranges are also possible.

Other methods of measuring the concentration of Compound 3 in an eye of a subject or an animal model are also possible. In some embodiments, the concentration of Compound 3 may be measured in the eye of the subject directly or indirectly (e.g., taking a sample of fluid, such as vitreous humor, from an eye of the subject).

In general, an increase in concentration of Compound 3 in an ocular site may be calculated by taking the difference in concentration measured between those of a test composition and a control composition, and dividing the difference by the concentration of the control composition. A test composition may include particles comprising a crystalline form of Compound 3, and the particles may be characterized as being mucus penetrating (e.g., having a relative velocity of greater than about 0.5, or another other relative velocity described herein). A control composition may include particles comprising the same crystalline form of Compound 3 as that present in the test composition, the particles having a substantially similar size as those of the test composition, but which are not mucus penetrating (e.g., having a relative velocity of less than about 0.5, or another other relative velocity described herein).

As described herein, in some embodiments, the particles, compositions, and/or formulations described herein, or a component thereof, is present in a sufficient amount to increase the bioavailability and/or concentration of Compound 3 in an ocular tissue, compared to the crystalline form of Compound 3 administered to the ocular tissue in the absence of the particles, compositions, and formulations described herein, or a component thereof.

The ocular tissue may be an anterior ocular tissue (e.g., a palpebral conjunctiva, a bulbar conjunctiva, or a cornea). In certain embodiments, the core particle of a formulation comprising a crystalline form of Compound 3 is present in a sufficient amount to increase the bioavailability and/or concentration of Compound 3 in an ocular tissue. In certain embodiments, the coating on the core particle of a formulation comprising a crystalline form of Compound 3 is present in a sufficient amount to increase the bioavailability and/or concentration of Compound 3 in an ocular tissue. In certain embodiments, the coating on the core particle of a formulation comprising a crystalline form of Compound 3 is present in a sufficient amount to increase the concentration of Compound 3 in an ocular tissue after at least 10 minutes, at least 20 minutes, at least 30 minutes, at least 1 hour, at least 2 hours, at least 3 hours, at least 4 hours, at least 6 hours, at least 9 hours, at least 12 hours, at least 18 hours, or at least 24 hours after administration of the formulation to the ocular tissue. In certain embodiments, the coating on the core particle of a formulation comprising a crystalline form of Compound 3 is present in a sufficient amount to increase the concentration of Compound 3 in an ocular tissue after less than or equal to 24 hours, less than or equal to 18 hours, less than or equal to 12 hours, less than or equal to 9 hours, less than or equal to 6 hours, less than or equal to 4 hours, less than or equal to 3 hours, less than or equal to 2 hours, less than or equal to 1 hour, less than or equal to 30 minutes, less than or equal to 20 minutes, or less than or equal to 10 minutes after administration of the formulation to the ocular tissue. Combinations of the above-referenced ranges are also possible (e.g., the concentration of Compound 3 increases after at least 10 minutes and less than or equal to 2 hours). Other ranges are also possible. In certain embodiments, the coating on the core particle of a formulation comprising a crystalline form of Compound 3 is present in a sufficient amount to increase the concentration of Compound 3 in an ocular tissue after about 30 minutes after administration of the formulation to the ocular tissue.

In some embodiments, the particles, compositions, and/or formulations described herein can be administered topically to an eye of a subject in various forms of doses. For example, the particles, compositions, and/or formulations described herein may be administered in a single unit dose or repeatedly administered in a plurality of single unit doses. A unit dose is a discrete amount of the particles, compositions, and/or formulations described herein comprising a predetermined amount of a pharmaceutical agent. In some embodiments, fewer numbers of doses (e.g., ½, ⅓, or ¼ the number doses) are required using the particles described herein having a mucus-penetrating coating compared to particles that do not have such a coating.

The exact amount of the particles, compositions, and/or formulations described herein required to achieve a therapeutically or prophylactically effective amount will vary from subject to subject, depending, for example, on species, age, and general condition of a subject, severity of the side effects or disorder, mode of administration, and the like. The particles, compositions, and/or formulations described herein can be delivered using repeated administrations where there is a period of time between consecutive doses. Repeated administration may be advantageous because it may allow the eye to be exposed to a therapeutically or prophylactically effective amount of Compound 3 for a period of time that is sufficiently long for the ocular condition to be treated, prevented, or managed. In certain embodiments, the period of time between consecutive doses is less than or equal to about 1 hour, less than or equal to about 2 hours, less than or equal to about 3 hours, less than or equal to about 4 hours, less than or equal to about 6 hours, less than or equal to about 12 hours, less than or equal to about 36 hours, or less than or equal to about 48 hours. In certain embodiments, the period of time between consecutive doses is at least about 1 hour, at least about 2 hours, at least about 3 hours, at least about 4 hours, at least about 6 hours, at least about 12 hours, at least about 36 hours, or at least about 48 hours. Combinations of the above-referenced ranges are also possible (e.g., a period of time between consecutive doses of greater than or equal to about 3 hours and less than or equal to about 12 hours). Other ranges are also possible.

Delivery of the particles, compositions, and/or formulations described herein to an ocular tissue may result in ophthalmically efficacious levels of Compound 3 in the ocular tissue for an extended period of time after administration (e.g., topical administration or administration by direct injection). An ophthalmically efficacious level of Compound 3 refers to an amount sufficient to elicit the desired biological response of an ocular tissue, i.e., treating an ocular disease. As will be appreciated by those skilled in this art, the ophthalmically efficacious level of Compound 3 may vary depending on such factors as the desired biological endpoint, the pharmacokinetics of Compound 3, the ocular disease being treated, the mode of administration, and the age and health of the subject. In certain embodiments, the ophthalmically efficacious level of Compound 3 is an amount of Compound 3, alone or in combination with other therapies, which provides a therapeutic benefit in the treatment of the ocular condition. The ophthalmically efficacious level of Compound 3 can encompass a level that improves overall therapy, reduces or avoids symptoms or causes of the ocular condition, or enhances the therapeutic efficacy of another therapeutic agent.

In some embodiments, an ophthalmically efficacious level of Compound 3 may be gauged, at least in part, by the maximum concentration ($C_{max}$) of Compound 3 in the ocular tissue after administration.

In some embodiments, the ophthalmically efficacious levels of Compound 3 are gauged, at least in part, by minimally efficacious concentrations of Compound 3, e.g., $IC_{50}$ or $IC_{90}$, as known in the art.

In certain embodiments in which ophthalmically efficacious levels (or $C_{max}$, $IC_{50}$, or $IC_{90}$) of Compound 3 are present in the ocular tissue for an extended period of time after administration, the extended period of time after administration can range from hours to days. In certain embodiments, the extended period of time after administration is at least 1 hour, at least 2 hours, at least 4 hours, at least 6 hours, at least 9 hours, at least 12 hours, at least 1 day, at least 2 days, at least 3 days, at least 4 days, at least 5 days, at least 6 days, or at least 1 week. In certain embodiments, the extended period of time after administration is less than or equal to 1 week, less than or equal to 6 days, less than or equal to 5 days, less than or equal to 4 days, less than or equal to 3 days, less than or equal to 2 days, less than or equal to 1 day, less than or equal to 12 hours, less than or equal to 9 hours, less than or equal to 6 hours, less than or equal to 4 hours, less than or equal to 2 hours, less than or equal to 1 hour. Combinations of the above-referenced ranges are also possible (e.g., an extended period of time of at least about 4 hours and less than or equal to about 1 week). Other ranges are also possible.

In certain embodiments, the particles, compositions, and/or formulations described herein may be at dosage levels sufficient to deliver an effective amount of Compound 3 to an eye of a subject to obtain a desired therapeutic or prophylactic effect. In certain embodiments, an effective amount of Compound 3 that is delivered to an appropriate eye tissue is at least about $10^{-3}$ ng/g, at least about $10^{-2}$ ng/g, at least about $10^{-1}$ ng/g, at least about 1 ng/g, at least about $10^1$ ng/g, at least about $10^2$ ng/g, at least about $10^3$ ng/g, at least about $10^4$ ng/g, at least about $10^5$ ng/g, or at least about $10^6$ ng/g of tissue weight. In certain embodiments, an effective amount of Compound 3 that is delivered to the eye is less than or equal to about $10^6$ ng/g, less than or equal to about $10^5$ ng/g, less than or equal to about $10^4$ ng/g, less than or equal to about $10^3$ ng/g, less than or equal to about $10^2$ ng/g, less than or equal to about $10^1$ ng/g, less than or equal to about 1 ng/g, less than or equal to about $10^{-1}$ ng/g, less than or equal to about $10^{-2}$ ng/g, or less than or equal to about $10^{-3}$ ng/g of tissue weight. Combinations of the above-referenced ranges are also possible (e.g., an effective amount of Compound 3 of at least about $10^{-2}$ ng/g and less than or equal to about $10^3$ ng/g of tissue weight). Other ranges are also possible. In certain embodiments, the particles, compositions, and/or formulations described herein may be at dosage levels sufficient to deliver an effective amount of Compound 3 to the back of an eye of a subject to obtain a desired therapeutic or prophylactic effect.

It will be appreciated that dose ranges as described herein provide guidance for the administration of provided particles, compositions, and/or formulations to an adult. The amount to be administered to, for example, a child or an adolescent can be determined by a medical practitioner or person skilled in the art and can be lower or the same as that administered to an adult.

The particles, compositions, and/or formulations described herein may be topically administered (e.g., ocular or dermal) by any method, for example, as by drops, powders, ointments, or creams. Other topical administration approaches or forms are also possible.

In certain embodiments, the compositions and/or formulations described herein are packaged as a ready to use shelf stable suspension. Eye drop formulations are traditionally liquid formulations (solutions or suspensions) which can be packaged in dropper bottles (which dispense a standard drop volume of liquid) or in individual use droppers (typically used for preservative free drops; used once and disposed). They can be stored in suspension and may retain the characteristics which allow the particles to avoid adhesion to mucus.

Methods of Preparing Particles and Pharmaceutical Compositions Thereof

In one aspect, the present invention provides methods of preparing the particles of the invention. Methods of preparing similar particles have been described in U.S. Patent Publication Nos. 2013/0316001, 2013/0316006, 2013/0316009, and 20130323179, each of which is incorporated by reference herein in its entirety.

The core of the particle may be formed by any suitable method. Suitable methods may include, for example, top-down techniques, i.e. techniques based on size reduction of relatively large particles into smaller particles (e.g., milling or homogenization) or bottom-up techniques, i.e. techniques based on the growth of particles from smaller particles or individual molecules (e.g., precipitation or spray-freezing into liquid).

In some embodiments, the core of the particle may be coated with a coating. For example, the core may be provided or formed in a first step, and then the core may be coated in a second step. In some embodiments, the core particle is formed and coated substantially simultaneously (e.g., in a single step).

In some embodiments, the particle is formed by a method that involves using a formulation process, a milling process, and/or a dilution process. In certain embodiments, a method of forming the particle includes a milling process, optionally with a formulation process and/or a dilution process. A formulation process may be used to form a suspension comprising a core material, one or more surface-altering agents, and other components, such as solvents, tonicity agents, chelating agents, salts, and/or buffers (e.g., a sodium citrate and citric acid buffer), each of which is as described herein. The formulation process may be performed using a formulation vessel. The core material and other components may be added into the formulation vessel at the same time or different times. A mixture of the core material and/or one or more other components may be stirred and/or shaken, or otherwise agitated in the vessel to facilitate suspending the components to form the suspension. The temperature and/or pressure of the core material, other components, and/or mixture may also be individually increased or decreased to facilitate the suspending process. In some embodiments, the core material and other components are processed as described herein in the formulation vessel under an inert atmosphere (e.g., nitrogen or argon) and/or protected from light. The suspension obtained from the formulation vessel may be subsequently subject to a milling process which may be followed by a dilution process.

In some embodiments involving a core comprising a solid material (e.g., crystalline compound of the invention) a milling process may be used to reduce the size of the solid material to form particles in a micrometer to nanometer size range. The milling process may be performed using a mill or other suitable apparatus. Dry and wet milling processes such as jet milling, cryo-milling, ball milling, media milling, sonication, and homogenization are known and can be used in methods of the invention. For example, in a wet milling process, a suspension of the solid material to be used to form the core ("core material") is agitated with or without excipients to reduce the size of the core to be formed. Dry milling is a process wherein the core material is mixed with milling media with or without excipients to reduce the size of the core to be formed. In a cryo-milling process, a suspension of the core material is mixed with milling media with or without excipients under cooled temperatures. In certain embodiments, when surface-altering agents are employed, a suspension comprising coated particles is obtained from the milling process. In certain embodiments, when surface-altering agents are not employed, a suspension comprising uncoated particles is obtained from the milling process.

The suspension of particles (coated or uncoated) of the invention obtained from a milling process may be further processed with a dilution process. A dilution process may be used to achieve a target dosing concentration by diluting a suspension of particles that were formed during a milling process, with or without surface-altering agents and/or other components. In certain embodiments, when a suspension of coated particles that comprise a first surface-altering agent is processed with a dilution process involving a second surface-altering agent, a suspension of coated particles that comprise the second surface-altering agent is obtained from the dilution process. In certain embodiments, when a suspension of coated particles that comprise a surface-altering agent is processed with a dilution process involving no or the same surface-altering agent, a suspension of coated particles that comprise the surface-altering agent is obtained from the dilution process. In certain embodiments, when a suspension of uncoated particles is processed with a dilution process involving a surface-altering agent, a suspension of coated particles comprising the surface-altering agent is obtained from the dilution process. The dilution process may be performed using a product vessel or any other suitable apparatus. In certain embodiments, the suspension of the particles is diluted, i.e., mixed or otherwise processed with a diluent, in the product vessel. The diluent may contain solvents, surface-altering agents, tonicity agents, chelating agents, salts, anti-microbial agents or a combination thereof, as described herein. The suspension and the diluent may be added into the product vessel at the same time or different times. In certain embodiments when the suspension is obtained from a milling process involving milling media, the milling media may be separated from the suspension before the suspension is added into the product vessel. The suspension, the diluent, or the mixture of the suspension and the diluent may be stirred and/or shaken, or otherwise agitated, to form the particles and/or pharmaceutical compositions of the invention. The temperature and/or pressure of the suspension, the diluent, or the mixture may also be individually increased or decreased to form the coated particles. In some embodiments, the suspension and the diluent are processed in the product vessel under an inert atmosphere (e.g., nitrogen or argon) and/or protected from light.

In some embodiments, the core and/or coated particles may be produced by milling of a solid material (e.g., a pharmaceutical agent) in the presence of one or more surface-altering agents. Small particles of a solid material may require the presence of one or more surface-altering agents, which may function as a stabilizer in some embodiments, in order to stabilize a suspension of particles without agglomeration or aggregation in a liquid solution. In some such embodiments, the stabilizer may act as a surface-altering agent, forming the coated particles of the invention.

As described herein, a method of forming the core and/or the coated particles, may involve choosing a surface-altering agent that is suitable for both milling and forming a coating on the core, wherein the coating renders the particle mucus penetrating.

In a wet milling process, milling may be performed in a dispersion (e.g., an aqueous dispersion) containing at least one surface-altering agent, a grinding medium, a solid to be milled (e.g., a solid pharmaceutical agent), and a solvent. The solvent described herein includes a single solvent or a mixture of different solvents. Any suitable amount of a surface-altering agent can be included in the solvent. In some embodiments, the surface-altering agent may be present in the solvent in an amount of at least about 0.001% (wt % or % weight to volume (w:v)), at least about 0.01%, at least about 0.1%, at least about 1%, at least about 3%, at least about 10%, at least about 30%, or at least about 60% of the solvent. In some cases, the surface-altering agent may be present in the solvent in an amount of about 100% (e.g., in an instance where the surface-altering agent is the solvent). In other embodiments, the surface-altering agent may be present in the solvent in an amount of less than about 100%, less than about 60%, less than about 30%, less than about 10%, less than about 3%, or less than about 1% of the solvent. Combinations of the above-referenced ranges are also possible (e.g., an amount of less than about 3% and at least about 1% of the solvent). Other ranges are also possible. In certain embodiments, the surface-altering agent is present in the solvent in an amount of about 0.01-2%, about 0.2-20%, about 0.1%, about 0.4%, about 1%, about 2%, about 5%, or about 10% of the solvent.

The particular range chosen may influence factors that may affect the ability of the particles to penetrate mucus such as the stability of the coating of the surface-altering agent on the particle surface, the average thickness of the coating of the surface-altering agent on the particles, the orientation of the surface-altering agent on the particles, the density of the surface altering agent on the particles, the ratio of the surface-altering agent to pharmaceutical agent, the concentration of the pharmaceutical agent, the size, dispersibility, and polydispersity of the particles formed, and the morphology of the particles formed.

The pharmaceutical agent may be present in the solvent in any suitable amount. In some embodiments, the pharmaceutical agent is present in an amount of at least about 0.001% (wt % or % weight to volume (w:v)), at least about 0.01%, at least about 0.1%, at least about 1%, at least about 3%, at least about 10%, at least about 30%, or at least about 60% of the solvent. In some cases, the pharmaceutical agent may be present in the solvent in an amount of less than about 100%, less than about 60%, less than about 30%, less than about 10%, less than about 3%, or less than about 1% of the solvent. Combinations of the above-referenced ranges are also possible (e.g., an amount of less than about 30% and at least about 1% of the solvent).

The ratio of surface-altering agent to pharmaceutical agent in a solvent may also vary. In some embodiments, the ratio of the surface-altering agent to pharmaceutical agent is at least about 0.001:1 (weight ratio, molar ratio, or w:v), at least about 0.01:1, at least about 0.01:1, at least about 1:1, at least about 2:1, at least about 3:1, at least about 5:1, at least about 10:1, at least about 30:1, at least about 100:1, or at least about 1000:1. In some embodiments, the ratio of the surface-altering agent to pharmaceutical agent is less than 1000:1 (weight ratio, molar ratio, or w:v), less than about 100:1, less than about 30:1, less than about 10:1, less than about 5:1, less than about 3:1, less than about 2:1, less than about 1:1, or less than about 0.1:1. Combinations of the above-referenced ranges are possible (e.g., a ratio of at least about 5:1 and less than about 30:1). Other ranges are also possible.

The surface-altering agents described herein that may act as stabilizers may be, for example, polymers or surfactants. Examples of polymers include those suitable for use in the coating of the particles of the invention, such as poly(vinyl alcohol) and PLURONICS®. Examples of surfactants include L-α-phosphatidylcholine (PC), 1,2-dipalmitoylphosphatidycholine (DPPC), oleic acid, sorbitan trioleate, sorbitan mono-oleate, sorbitan monolaurate, polyoxylene sorbitan fatty acid esters (TWEENS), polysorbates (e.g., polyoxyethylene sorbitan monooleate) (e.g., TWEEN 80®), polyoxyethylene sorbitan monostearate (e.g., TWEEN 60®), polyoxyethylene sorbitan monopalmitate (e.g., TWEEN 40®), polyoxyethylene sorbitan monolaurate (e.g., TWEEN 20®), natural lecithin, oleyl polyoxyethylene ether, stearyl polyoxyethylene ether, lauryl polyoxyethylene ether, polyoxylene alkyl ethers, block copolymers of oxyethylene and oxypropylene, polyoxyethylene stearates, polyoxyethylene castor oil and their derivatives, Vitamin-PEG and their derivatives, synthetic lecithin, diethylene glycol dioleate, tetrahydrofurfuryl oleate, ethyl oleate, isopropyl myristate, glyceryl monooleate, glyceryl monostearate, glyceryl monoricinoleate, cetyl alcohol, stearyl alcohol, polyethylene glycol, cetyl pyridinium chloride, benzalkonium chloride, olive oil, glyceryl monolaurate, corn oil, cotton seed oil, and sunflower seed oil. Derivatives of the above-noted compounds are also possible. Combinations of the above-noted compounds and others described herein may also be used as surface-altering agents in the inventive particles. As described herein, in some embodiments a surface-altering agent may act as a stabilizer, a surfactant, and/or an emulsifier. In some embodiments, the surface altering agent may aid particle transport in mucus.

A stabilizer used for milling may form the coating of a particle of the invention, wherein the coating renders the particle mucus penetrating. The stabilizer may also be exchanged with one or more other surface-altering agents after the particle has been formed. For example, a first stabilizer/surface-altering agent may be used during a milling process and may form a first coating of the particle of the invention, and all or part of the first stabilizer/surface-altering agent may then be exchanged with a second stabilizer/surface-altering agent to form a second coating of the particle. In some embodiments, the second stabilizer/surface-altering agent may render the particle mucus penetrating more than the first stabilizer/surface-altering agent. In some embodiments, a particle comprising multiple coatings that include multiple surface-altering agents is formed by a method of the invention.

Any suitable grinding medium can be used for milling. In some embodiments, a ceramic and/or polymeric material and/or a metal can be used. Examples of suitable materials include zirconium oxide, silicon carbide, silicon oxide, silicon nitride, zirconium silicate, yttrium oxide, glass, alumina, alpha-alumina, aluminum oxide, polystyrene, poly (methyl methacrylate), titanium, and steel. A grinding medium may have any suitable size. For example, the grinding medium may have an average diameter of at least about 0.1 mm, at least about 0.2 mm, at least about 0.5 mm, at least about 0.8 mm, at least about 1 mm, at least about 2 mm, or at least about 5 mm. In some cases, the grinding medium may have an average diameter of less than about 5 mm, less than about 2 mm, less than about 1 mm, less than about 0.8, less than about 0.5 mm, or less than about 0.2 mm. Combinations of the above-referenced ranges are also possible (e.g., an average diameter of at least about 0.5 millimeters and less than about 1 mm). Other ranges are also possible.

A solvent may be used for milling. The choice of the solvent suitable for milling may depend on factors like the solid material (e.g., a solid pharmaceutical agent) being milled, the particular type of stabilizer/surface-altering agent (e.g., one that may render the particle mucus penetrating), and the grinding material. The solvent suitable for milling may be one of those solvents that do not substantially dissolve the solid material or the grinding material, but dissolve the stabilizer/surface-altering agent to a suitable degree. Examples of the solvents suitable for milling include water, aqueous solutions, buffered solutions, alcohols (e.g., ethanol, methanol, and butanol), and mixtures thereof, each of which may optionally include other components, such as one or more pharmaceutical excipients, polymers, pharmaceutical agents, salts, preservative agents, viscosity modifiers, tonicity modifiers, taste masking agents, antioxidants, and pH modifiers. In some embodiments, the solvent suitable for milling is an organic solvent.

A pharmaceutical agent described herein (e.g., a crystalline form of Compound 3) may have a suitable solubility in a solvent suitable for milling, such as a solubility in one or more ranges described herein for aqueous solubility or for solubility in a coating solution. A pharmaceutical agent having a relatively low solubility in a solvent (e.g., water or a coating solution) may be preferred because a milling process described herein typically requires a material (e.g., a pharmaceutical agent) to be in a solid form in order for the material to be milled. In some cases, if the material to be milled has a relatively high soluble in a solvent (e.g., water or a coating solution) used in the milling process, milling may not be conducted because significant or complete dissolution of the material to be milled in the solvent will occur. In certain embodiments, a relatively high solubility of a solid material (e.g., a solid pharmaceutical agent) in a solvent is at least about 1 mg/mL, at least about 3 mg/mL, or at least about 10 mg/mL at 25° C. In certain embodiments, a relatively low solubility of a substance (e.g., a pharmaceutical agent) in a solvent is less than about 1 mg/mL, less than about 0.3 mg/mL, less than about 0.1 mg/mL, less than about 0.03 mg/mL, less than about 0.01 mg/mL, less than about 0.003 mg/mL, or less than about 0.001 mg/mL at 25° C. The solid material may have these or other ranges of solubilities at any point throughout the pH range (e.g., from pH 1 to pH 14).

In other embodiments, the core and/or coated particles may be formed by an emulsification process or technique (emulsification) known in the art. See, e.g., U.S. Patent Publication No. 20130316006. Generally, emulsification techniques may involve dissolving or dispersing a material to be used as the core in a solvent; this solution or dispersion is then emulsified in a second immiscible solvent, thereby forming a plurality of particles comprising the material. Suitable emulsification techniques may include formation of oil-in-water emulsions, water-in-oil emulsions, water-oil-water emulsions, oil-water-oil emulsions, solid-in-oil-in-water emulsions, and solid-in-water-in-oil emulsions, etc., with or without subsequent solvent removal, for example, by evaporation or extraction. Emulsification techniques are versatile and may be useful for preparing core particles comprising pharmaceutical agents having a relatively low aqueous solubility as well as pharmaceutical agents having a relatively high aqueous solubility.

In some embodiments, the core particles described herein may be produced by emulsification in the presence of one or more surface-altering agents. In some such embodiments, the stabilizer may act as a surface-altering agent, forming a coating on the particle (i.e., the emulsification and coating steps may be performed substantially simultaneously).

In some embodiments, a method of forming a core particle by emulsification involves choosing a stabilizer that is suitable for both emulsification and for forming a coating on the particle and rendering the particle mucus penetrating. For example, as described in more detail below, it has been demonstrated that 200-500 nm nanoparticles of a model polymer PLA produced by emulsification in the presence of certain PVA polymers resulted in particles that can penetrate physiological mucus samples at the same rate as well-established PEGylated polymeric MPP. Interestingly, it was observed that only a subset of PVA polymers tested fit the criteria of being suitable for both emulsification and for forming a coating on the particle that renders the particle mucus penetrating, as described in more detail below.

In other embodiments, the particles are first formed using an emulsification technique, following by coating of the particles with a surface-altering agent.

Any suitable solvent and solvent combinations can be used for emulsification. Some examples of solvents which can serve as oil phase are organic solvents such chloroform, dichloromethane, ethyl acetate, ethyl ether, petroleum ether (hexane, heptane), and oils such as peanut oil, cottonseed oil; safflower oil; sesame oil; olive oil; corn oil soybean oil, and silicone oil. Some examples of solvents which can serve as water phase are water and aqueous buffers. Other solvents are also possible.

The core and/or coated particles may also be formed by a precipitation process or technique (precipitation). Precipitation techniques (e.g., microprecipitation, nanoprecipitation, crystallization, and controlled crystallization) may involve forming a first solution comprising the material that is to form the core (e.g., a pharmaceutical agent) and a first solvent, wherein the material has a relatively high solubility in the first solvent. The first solution may be added to a second solution comprising a second solvent that is an anti-solvent, in which the material has a relatively low solubility, thereby forming a plurality of particles comprising the material. In certain embodiments, the second solvent is miscible with the first solvent. In some embodiments, one or more surface-altering agents and/or surfactants may be present in the first and/or second solutions. A coating may be formed during the process of precipitating the core (e.g., the coating of the particles may be formed substantially simultaneously when the precipitation is performed) to form the coated particles of the invention.

In other embodiments, the core of the particles of the invention is first formed using a precipitation technique, following by coating of the core with a surface-altering agent to form the coated particles of the invention.

In some embodiments, a precipitation technique may be used to form polymeric core of the particles of the invention with or without a pharmaceutical agent. Generally, a precipitation technique involves dissolving a polymer that is to form the core in a first solvent, in the presence or absence of a pharmaceutical agent, to form a solution. The solution is then added to a second solvent that is an anti-solvent and is miscible with the first solvent, in the presence or absence of one or more excipients, to form the core of the particles. In some embodiments, precipitation is useful for preparing a polymeric core comprising one or more pharmaceutical agents having a relatively low aqueous solubility.

The precipitation described herein involves the use of a first solvent. Examples of suitable first solvents for precipitation include organic solvents (e.g., acetone, acetonitrile, dimethylformamide, dimethylsulfoxide, N-methyl-2-pyrrolidone, 2-pyrrolidone, and tetrahydrofuran) and inorganic solvents.

The precipitation described herein also involves the use of a second solvent. In certain embodiments, the second solvent suitable for precipitation is an anti-solvent. Examples of second solvents suitable for precipitation include the solvents described herein that may be used for milling. In some embodiments, the second solvents suitable for precipitation is water, an aqueous solution (e.g., a buffered solution), an alcohol (e.g., methanol, ethanol, propanol, or butanol), or a mixture thereof, optionally including one or more other components, such as pharmaceutical excipients, polymers, and pharmaceutical agents.

Surface-altering agents for the emulsification and precipitation described herein may be polymers or surfactants, including the surface-altering agents described herein that may be used for milling.

Examples of polymers suitable for forming all or part of the core of the particles of the invention by the emulsification or precipitation may include polyamines, polyethers, polyamides, polyesters, polycarbamates, polyureas, polycarbonates, polystyrenes, polyimides, polysulfones, polyurethanes, polyacetylenes, polyethylenes, polyethyleneimines, polyisocyanates, polyacrylates, polymethacrylates, polyacrylonitriles, polyarylates, polypeptides, polynucleotides, and polysaccharides. Non-limiting examples of specific polymers include poly(caprolactone) (PCL), ethylene vinyl acetate polymer (EVA), poly(lactic acid) (PLA), poly(L-lactic acid) (PLLA), poly(glycolic acid) (PGA), poly(lactic acid-co-glycolic acid) (PLGA), poly(L-lactic acid-co-glycolic acid) (PLLGA), poly(D,L-lactide) (PDLA), poly(L-lactide) (PLLA), poly(D,L-lactide-co-caprolactone), poly (D,L-lactide-co-caprolactone-co-glycolide), poly(D,L-lactide-co-PEO-co-D,L-lactide), poly(D,L-lactide-co-PPO-co-D,L-lactide), polyalkyl cyanoacrylate, polyurethane, poly-L-lysine (PLL), hydroxypropyl methacrylate (HPMA), poly(ethylene glycol), poly-L-glutamic acid, poly(hydroxy acids), polyanhydrides, polyorthoesters, poly(ester amides), polyamides, poly(ester ethers), polycarbonates, polyalkylenes such as polyethylene and polypropylene, polyalkylene glycols such as poly(ethylene glycol) (PEG), polyalkylene oxides (PEO), polyalkylene terephthalates such as poly(ethylene terephthalate), polyvinyl alcohols (PVA), polyvinyl ethers, polyvinyl esters such as poly(vinyl acetate), polyvinyl halides such as poly(vinyl chloride) (PVC), polyvinylpyrrolidone, polysiloxanes, polystyrene (PS), polyurethanes, derivatized celluloses such as alkyl celluloses, hydroxyalkyl celluloses, cellulose ethers, cellulose esters, nitro celluloses, hydroxypropylcellulose, carboxymethylcellulose, polymers of acrylic acids, such as poly(methyl(meth)acrylate) (PMMA), poly(ethyl(meth) acrylate), poly(butyl(meth)acrylate), poly(isobutyl(meth) acrylate), poly(hexyl(meth)acrylate), poly(isodecyl(meth) acrylate), poly(lauryl(meth)acrylate), poly(phenyl(meth) acrylate), poly(methyl acrylate), poly(isopropyl acrylate), poly(isobutyl acrylate), poly(octadecyl acrylate) (jointly referred to herein as "polyacrylic acids"), and copolymers and mixtures thereof, polydioxanone and its copolymers, polyhydroxyalkanoates, polypropylene fumarate), polyoxymethylene, poloxamers, poly(ortho)esters, poly(butyric acid), poly(valeric acid), poly(lactide-co-caprolactone), and trimethylene carbonate, polyvinylpyrrolidone, bovine serum albumin, human serum albumin, collagen, DNA, RNA, carboxymethyl cellulose, chitosan, dextran.

Polymers suitable for forming all or portions of a core and/or surface-altering agent may also include a poly(ethylene glycol)-vitamin E conjugate (hereinafter, "PEG-VitE conjugate"). The particles, compositions, and/or formulations including a PEG-VitE conjugate, and methods of making and using the particles, compositions, and/or formulations, are provided in more detail in international PCT application publication WO2012/061703, which is incorporated herein by reference in its entirety for all purposes. In some cases, the molecular weight of the PEG portion of the PEG-VitE conjugate is greater than about 2 kDa. The molecular weight of the PEG portion of the PEG-VitE conjugate may be selected so as to aid in the formation and/or transport of the particle across a mucosal barrier as described herein. In some embodiments, use of a PEG-VitE conjugate with a PEG portion having a molecular weight greater than about 2 kDa may allow for greater penetration of the particles through a mucosal barrier as compared to use of a PEG-VitE conjugate with a PEG portion having a molecular weight less than about 2 kDa. Additionally, in certain embodiments a higher molecular weight PEG portion may facilitate drug encapsulation. The combined ability to act as a surfactant and to reduce mucoadhesion provides important benefits as compared to other commonly used surfactants for drug encapsulation. In some cases, the molecular weight of the PEG portion of the PEG-VitE conjugate is between about 2 kDa and about 8 kDa, or between about 3 kDa and about 7 kDa, or between about 4 kDa and about 6 kDa, or between about 4.5 kDa and about 6.5 kDa, or about 5 kDa.

In some embodiments, a precipitation technique may be used to form particles comprised predominantly of a pharmaceutical agent (e.g., a crystalline form of Compound 3). In certain embodiments, the particles of the invention formed by the precipitation technique comprise predominantly a crystalline form of Compound 3 that is a nanocrystal. Generally, such a precipitation technique involves dissolving Compound 3 that is to form the core in a first solvent, which is then added to a second solvent that is an anti-solvent, in which the crystalline form of Compound 3 has a relatively low solubility, in the presence or absence of one or more pharmaceutical excipients, to form the core or uncoated particle. In some embodiments, this technique may be useful for preparing, for example, particles of pharmaceutical agents that are slightly soluble (1-10 mg/mL), very slightly soluble (0.1-1 mg/mL) or practically insoluble (<0.1 mg/mL) in aqueous solutions (e.g., agents having a relatively low aqueous solubility).

A pharmaceutical agent described herein (e.g., a crystalline form of Compound 3) may have a suitable solubility in the first and second solvents suitable for precipitation, such as a solubility in one or more ranges described herein for aqueous solubility or for solubility in a coating solution. A pharmaceutical agent having a relatively high solubility in the first solvent (e.g., an organic solvent) may be preferred. In certain embodiments, the pharmaceutical agent substantially or completely dissolves in the first solvent. A pharmaceutical agent having a relatively low solubility in the second solvent (e.g., water or a coating solution) may also be preferred. In certain embodiments, the solubility of the pharmaceutical agent in a mixture of the first and second solvents is lower than the solubility of the pharmaceutical agent in the first solvent. The relatively high solubility and relatively low solubility are as described herein.

Another exemplary method of forming the core and/or coated particle is a freeze-drying process or technique known in the art. See, e.g., U.S. Patent Publication No. 2013/0316006. In this technique, Compound 3 may be dissolved in an aqueous solution, optionally containing a surface-altering agent. The solution may be immediately flash frozen and freeze dried. Dry powder can be reconstituted in a suitable solvent (e.g., an aqueous solution such as water) at a desired concentration.

If the surface-altering agent is present in the solvent prior to freeze drying, it may be present at any suitable concentration, such as a concentration of at least about 0.001% (w/v), at least about 0.005% (w/v), at least about 0.01% (w/v), at least about 0.05% (w/v), at least about 0.1% (w/v), at least about 0.5% (w/v), at least about 1% (w/v), or at least about 5% (w/v) in the aqueous solution. In some instances, the surface-altering agent is present in the solvent at a concentration of less than or equal to about 5% (w/v), less than or equal to about 1% (w/v), less than or equal to about 0.5% (w/v), less than or equal to about 0.1% (w/v), less than or equal to about 0.05% (w/v), less than or equal to about 0.01% (w/v), or less than or equal to about 0.005% (w/v). Combinations of the above-referenced ranges are also possible (e.g., a concentration of at least about 0.01% (w/v) and less than or equal to about 1% (w/v). Other ranges are also possible.

The concentration of surface-altering agent present in the solvent may be above or below the critical micelle concentration (CMC) of the surface-altering agent, depending on the particular surface-altering agent used. In other embodiments, stable particles can be formed by adding excess counter-ion to a solution containing a pharmaceutical agent. The precipitate can then be washed by various methods such as centrifugation. The resultant slurry may be sonicated. One or more surface-altering agents may be added to stabilize the resultant particles.

Other methods of forming core particles are also possible. For example, additional techniques of forming the core and/or coated particles include coacervation-phase separation, melt dispersion, interfacial deposition, in situ polymerization, self-assembly of macromolecules (e.g., formation of polyelectrolyte complexes or polyelectrolyte-surfactant complexes), spray-drying and spray-congealing, electrospray, air suspension coating, pan and spray coating, freeze-drying, air drying, vacuum drying, fluidized-bed drying, precipitation (e.g., nanoprecipitation, microprecipitation), critical fluid extraction, and lithographic approaches (e.g., soft lithography, step and flash imprint lithography, interference lithography, and photolithography). Combinations of the methods described herein are also possible. In some embodiments, a core of a pharmaceutical agent is first formed by precipitation, and then the size of the core is reduced by a milling process, optionally a coating is form on the core by the milling process.

Following the formation of the core of the particles including a pharmaceutical agent, the core may be optionally exposed to a solution comprising a (second) surface-altering agent that may associate with and/or coat the core. In embodiments in which the pharmaceutical agent already includes a coating of a first surface-altering agent, all or part of the first surface-altering agent may be exchanged with a second surface-altering agent. In some embodiments, the second surface-altering agent renders the particle mucus penetrating more than the first surface-altering agent does. In some embodiments, a particle having a coating including multiple surface-altering agents is formed (e.g., in a single layer or in multiple layers). In some embodiments, a particle having multiple coatings (e.g., each coating optionally comprising different surface-altering agents) may be formed. In some embodiments, the coating is in the form of a monolayer of a surface-altering agent. Other configurations are also possible.

In any of the methods described herein, a coating comprising a surface-altering agent may be formed on a core of the particles of the invention by incubating the core in a solution including the surface-altering agent for a period of at least about 1 minute, at least about 3 minutes, at least about 10 minutes, at least about 20 minutes, at least about 30 minutes, at least about 60 minutes, or more. In some cases, incubation may take place for a period of less than about 10 hours, less than about 3 hours, or less than about 60 minutes. Combinations of the above referenced ranges are also possible (e.g., an incubation period of less than 60 minutes and at least about 1 minute).

Methods of Treatment and Uses

A range of diseases may result when the body of a subject loses control over angiogenesis, i.e., new blood vessels grow abnormally (i.e., excessively or insufficiently) or grow as a result of a tumor. Excessive angiogenesis is often observed in subjects with diseases such as proliferative diseases (e.g., cancers, benign neoplasms, inflammatory diseases, autoimmune diseases) and ocular diseases, especially with cancer, diabetic retinopathy, macular degeneration, rheumatoid arthritis, and psoriasis. In these diseases, new blood vessels feed abnormal tissues and/or destroy normal tissues. Excessive angiogenesis may occur when there are abnormal amounts of angiogenic growth factors present, overwhelming the effects of natural angiogenesis inhibitors. Therefore, inhibiting new blood vessel growth may be useful to treat diseases associated with excessive angiogenesis. Insufficient angiogenesis is typically observed in subjects with a disease such as coronary artery disease, stroke, or chronic wounds. In these diseases, blood vessel growth is inadequate, and circulation is not properly restored, which may lead to tissue death.

VEGFs have been found to play a major role in angiogenesis, for example, by increasing the number of capillaries in a given network. In vitro studies have demonstrated that bovine capillary endothelial cells proliferated and showed signs of tube structures upon stimulation with VEGF. Upregulation of VEGF is a major component of the physiological response to exercise and its role in angiogenesis is suspected to be a possible treatment in vascular injuries. In vitro studies have showed that VEGFs are a potent stimulator of angiogenesis because, among other things, in the presence of this growth factor, plated endothelial cells will proliferate and migrate, eventually forming tube structures resembling capillaries. VEGFs may cause a massive signaling cascade in endothelial cells. Binding to VEGF receptor-2 starts a tyrosine kinase signaling cascade that stimulates the production of factors that variously stimulate vessel permeability, proliferation/survival, migration, and finally differentiation into mature blood vessels. Mechanically, VEGF is upregulated with muscle contractions as a result of increased blood flow to affected areas. The increased flow also causes a large increase in the mRNA production of VEGF receptors 1 and 2. The increase in receptor production indicates that muscle contractions could cause upregulation of the signaling cascade relating to angiogenesis.

In one aspect, the present invention provides methods of treating and/or preventing a disease associated with abnormal angiogenesis, which comprise administering an effective amount of Compound 3 to a subject in need thereof. In certain embodiments, the disease associated with abnormal angiogenesis is treated and/or prevented by the inventive methods. In certain embodiments, the disease being treated and/or prevented by the inventive methods is associated with excessive and/or pathological angiogenesis.

In another aspect, the present invention provides methods of treating and/or preventing a disease associated with aberrant signaling of a growth factor in a subject in need thereof. In certain embodiments, the disease associated with aberrant signaling of a growth factor is treated and/or prevented by the inventive methods. In certain embodiments, the disease is associated with excessive signaling of the growth factor. In certain embodiments, the disease being treated and/or prevented by the inventive methods is associated with aberrant signaling of VEGF. In certain embodiments, the disease is associated with excessive or aberrant signaling of VEGF-A, VEGF-B, VEGF-C, VEGF-D, VEGF-F, and/or placental growth factor (PGF). In certain embodiments, the disease associated with aberrant signaling of VEGF is treated and/or prevented by the inventive methods.

As used herein, the term "growth factor-associated disease" means any disease where growth factors are known to play a role. Accordingly, in some embodiments, the present disclosure relates to treating diseases in which growth factors are known to play a role. Such diseases include proliferative diseases, eye diseases, dermatological diseases, inflammation diseases, and metabolic diseases.

In some embodiments, the present disclosure provides methods of treating a disease comprising contacting a biological sample with an effective amount of Compound 3. In certain embodiments, the biological sample includes a cell or tissue. In some embodiments, the methods comprise inhibiting growth factor signaling in a cell, tissue, or subject. In some embodiments, the biological sample is an ocular tissue. In certain embodiments, the method is an in vitro method. In certain embodiments, the method is an in vivo method. It will be understood by one of ordinary skill in the art that levels of inhibition are not necessary to be 100%. The levels of inhibition can be at least 10% inhibition, about 10% to about 25% inhibition, about 25% to about 50% inhibition, about 50% to about 75% inhibition, at least 50% inhibition, at least 75% inhibition, about 80% inhibition, about 90% inhibition, or greater than 90% inhibition.

In certain embodiments, the disease being treated and/or prevented by the inventive methods is a proliferative disease. All types of proliferative diseases described herein may be treated and/or prevented by the inventive methods. In certain embodiments, the proliferative disease is treated and/or prevented by the inventive methods. In certain embodiments, the disease being treated and/or prevented by the inventive methods is cancer. All types of cancer described herein may be treated and/or prevented by the inventive methods. In certain embodiments, the cancer is an ocular cancer. In certain embodiments, the ocular cancer is retinoblastoma, medulloepithelioma, uveal melanoma, ciliary body melanoma, or primary intraocular lymphoma. In certain embodiments, the cancer is treated and/or prevented by the inventive methods. In certain embodiments, the disease being treated and/or prevented by the inventive methods is a benign neoplasm. All types of benign neoplasm described herein may be treated and/or prevented by the inventive methods. In certain embodiments, the benign neoplasm is an ocular benign neoplasm. In certain embodiments, the benign neoplasm is orbital dermoid cysts. In certain embodiments, the benign neoplasm is treated and/or prevented by the inventive methods.

In certain embodiments, the disease being treated and/or prevented by the inventive methods is an inflammatory disease. All types of inflammatory diseases described herein may be treated and/or prevented by the inventive methods. In certain embodiments, the inflammatory disease is an ocular inflammatory disease. In certain embodiments, the ocular inflammatory disease is post-surgical inflammation. In certain embodiments, the inflammatory disease is treated and/or prevented by the inventive methods. In certain embodiments, the disease being treated and/or prevented by the inventive methods is an autoimmune disease. All types of autoimmune diseases described herein may be treated and/or prevented by the inventive methods. In certain embodiments, the autoimmune disease is rheumatoid arthritis. In certain embodiments, the autoimmune disease is treated and/or prevented by the inventive methods. In certain embodiments, the disease being treated and/or prevented by the inventive methods is diabetes. In certain embodiments, the disease is type 1 diabetes. In certain embodiments, the disease is type 2 diabetes. In certain embodiments, the disease is gestational diabetes. In certain embodiments, the diabetes is treated and/or prevented by the inventive methods.

The disease being treated and/or prevented by the inventive methods may be an ocular disease. In some embodiments, the ocular disease being treated and/or prevented by the inventive methods is an anterior ocular disease that occurs at the anterior portion or "front" of the eye of a subject. The anterior portion of the eye includes the cornea, iris, conjunctiva, tear film, corneal epithelium, anterior chamber, lens, ciliary body, ciliary zonule, posterior chamber, retina, macula, sclera, an optic nerve, choroid, and vitreous chamber. In certain embodiments, the anterior ocular disease being treated and/or prevented by the inventive methods is allergy, post-surgical inflammation, uveitis, an infection (e.g., a viral, bacterial, or fungal infection), aphakia, pseudophakia, astigmatism, blepharospasm, cataract, a conjunctival disease, conjunctivitis, a corneal disease, corneal edema, blepharitis, meibomian gland disease, corneal transplant surgery, corneal ulcer, dry eye (e.g., dry eye syndrome), an eyelid disease, a lacrimal apparatus disease, lacrimal duct obstruction, laser induced exudation, myopia, presbyopia, pterygium, pupil disorders, corneal neovascularization, a refractive disorder, strabismus, or glaucoma. In some embodiments, the ocular disease being treated and/or prevented by the inventive methods is a posterior ocular disease that occurs at the posterior portion or "back" of the eye. The posterior portion of the eye includes the choroid, sclera, vitreous humor, vitreous chamber, retina, macula, optic nerve, and blood vessels and nerves which vascularize or innervate a posterior ocular region or site. In certain embodiments, the posterior ocular disease being treated and/or prevented by the inventive methods is intraocular melanoma, acute macular neuroretinopathy, an exudative eye disease, Behcet's disease, exudative retinopathy, macular edema, retinopathy of prematurity, an epiretmal membrane disorder, choroidal neovascularization, uveitis, diabetic uveitis, histoplasmosis, an infection (e.g., a viral, bacterial, or fungal infection), macular degeneration (e.g., acute macular degeneration and age-related macular degeneration (AMD, such as non-exudative age-related macular degeneration and exudative age-related macular degeneration)), edema (e.g., macular edema, such as cystoid macular edema (CME) and diabetic macular edema (DME)), multifocal choroiditis, ocular trauma which affects a posterior ocular site or location, ocular cancer, a retinal disorder (e.g., central retinal vein occlusion), diabetic retinopathy (e.g., proliferative diabetic retinopathy and non-proliferative diabetic retinopathy), proliferative vitreoretinopathy (PVR), retinal arterial occlusive disease, retinal detachment, uveitic retinal disease, sympathetic opthalmia, Vogt Koyanagi-Harada (VKH) syndrome, uveal diffusion, a posterior ocular condition caused by or influenced by an ocular laser treatment, a posterior ocular condition caused by or influenced by a photodynamic therapy, photocoagulation, radiation retinopathy, an epiretinal membrane disorder, branch retinal vein occlusion, anterior ischemic optic neuropathy, non-retinopathy diabetic retinal dysfunction, retinitis pigmentosa, retinoblastoma, or glaucoma. In certain embodiments, the ocular disease being prevented and/or treated by the inventive methods is macular degeneration. In certain embodiments, the ocular disease is age-related macular degeneration (AMD). In certain embodiments, the ocular disease is glaucoma. In certain embodiments, the ocular disease is diabetic retinopathy. In certain embodiments, the ocular disease is retinoblastoma. In certain embodiments, the ocular disease is edema. In certain embodiments, the ocular disease is cystoid macular edema (CME). In certain embodiments, the ocular disease is diabetic macular edema (DME). In certain embodiments, the ocular disease is an ocular inflammatory disease. In certain embodiments, the ocular disease is post-surgical inflammation. In certain embodiments, the ocular disease is uveitis (e.g., anterior uveitis, intermediate uveitis, and posterior uveitis). In certain embodiments, the ocular disease is blepharitis. In certain embodiments, the ocular disease is panuveitis. In certain embodiments, the ocular disease is scleritis. In certain embodiments, the ocular disease is dry eye. In certain embodiments, the ocular disease is Sjögren's syndrome. In certain embodiments, the ocular disease is an eye surgery. In certain embodiments, the ocular disease is treated and/or prevented by the inventive methods.

In certain embodiments, the compounds, particles, compositions, and/or formulations described herein are packaged as a ready to use shelf stable suspension. Eye drop formulations are traditionally liquid formulations (solutions or suspensions) which can be packaged in dropper bottles (which dispense a standard drop volume of liquid) or in individual use droppers (typically used for preservative free drops, used once and disposed). These formulations are ready to use and can be self-administered. In some cases the bottle should be shaken before use to ensure homogeneity of the formulation, but no other preparation may be necessary. This may be the simplest and most convenient method of ocular delivery. The compositions and/or formulations described herein can be packaged in the same way as traditional eye drop formulations.

Another aspect of the present invention relates to methods of inhibiting the aberrant signaling of a growth factor (e.g., VEGF) signaling pathway in a subject or cell. In certain embodiments, the aberrant signaling of the growth factor is inhibited by the inventive methods.

In another aspect, the present invention provides methods of inhibiting the abnormal or pathological angiogenesis in a subject in need thereof. In certain embodiments, the abnormal or pathological angiogenesis is inhibited by the inventive methods.

In certain embodiments, the subject described herein is a human. In certain embodiments, the subject is an animal. The animal may be of either sex and may be at any stage of development. In certain embodiments, the subject is a fish. In certain embodiments, the subject is a mammal. In certain embodiments, the subject is a domesticated animal, such as a dog, cat, cow, pig, horse, sheep, or goat. In certain embodiments, the subject is a companion animal such as a dog or cat. In certain embodiments, the subject is a livestock animal such as a cow, pig, horse, sheep, or goat. In certain embodiments, the subject is a zoo animal. In another embodiment, the subject is a research animal such as a rodent (e.g., mouse, rat), dog, pig, or non-human primate. In certain embodiments, the animal is a genetically engineered animal. In certain embodiments, the animal is a transgenic animal.

In some embodiments, the crystalline forms described herein are useful for treating a cancer including, but not limited to, acoustic neuroma, adenocarcinoma, adrenal gland cancer, anal cancer, angiosarcoma (e.g., lymphangiosarcoma, lymphangioendotheliosarcoma, hemangiosarcoma), appendix cancer, benign monoclonal gammopathy, biliary cancer (e.g., cholangiocarcinoma), bladder cancer, breast cancer (e.g., adenocarcinoma of the breast, papillary carcinoma of the breast, mammary cancer, medullary carcinoma of the breast), brain cancer (e.g., meningioma; glioma, e.g., astrocytoma, oligodendroglioma; medulloblastoma), bronchus cancer, carcinoid tumor, cervical cancer (e.g., cervical adenocarcinoma), choriocarcinoma, chordoma, craniopharyngioma, colorectal cancer (e.g., colon cancer, rectal cancer, colorectal adenocarcinoma), epithelial carcinoma, ependymoma, endotheliosarcoma (e.g., Kaposi's sarcoma, multiple idiopathic hemorrhagic sarcoma), endometrial cancer (e.g., uterine cancer, uterine sarcoma), esophageal cancer (e.g., adenocarcinoma of the esophagus, Barrett's adenocarcinoma), Ewing sarcoma, eye cancer (e.g., intraocular melanoma, retinoblastoma), familiar hypereosinophilia, gall bladder cancer, gastric cancer (e.g., stomach adenocarcinoma), gastrointestinal stromal tumor (GIST), head and neck cancer (e.g., head and neck squamous cell carcinoma, oral cancer (e.g., oral squamous cell carcinoma (OSCC), throat cancer (e.g., laryngeal cancer, pharyngeal cancer, nasopharyngeal cancer, oropharyngeal cancer)), hematopoietic cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma (DLBCL)), follicular lymphoma, chronic lymphocytic leukemia/small lymphocytic lymphoma (CLUSLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., "Waldenström's macroglobulinemia"), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungiodes, Sezary syndrome), angioimmunoblastic T-cell lymphoma, extranodal natural killer T-cell lymphoma, enteropathy type T-cell lymphoma, subcutaneous panniculitis-like T-cell lymphoma, anaplastic large cell lymphoma); a mixture of one or more leukemia/lymphoma as described above; and multiple myeloma (MM)), heavy chain disease (e.g., alpha chain disease, gamma chain disease, mu chain disease), hemangioblastoma, inflammatory myofibroblastic tumors, immunocytic amyloidosis, kidney cancer (e.g., nephroblastoma a.k.a. Wilms' tumor, renal cell carcinoma), liver cancer (e.g., hepatocellular cancer (HCC), malignant hepatoma), lung cancer (e.g., bronchogenic carcinoma, small cell lung cancer (SCLC), non-small cell lung cancer (NSCLC), adenocarcinoma of the lung), leiomyosarcoma (LMS), mastocytosis (e.g., systemic mastocytosis), myelodysplastic syndrome (MDS), mesothelioma, myeloproliferative disorder (MPD) (e.g., polycythemia Vera (PV), essential thrombocytosis (ET), agnogenic myeloid metaplasia (AMM), a.k.a. myelofibrosis (MF), chronic idiopathic myelofibrosis, chronic myelocytic leukemia (CML), chronic neutrophilic leukemia (CNL), hypereosinophilic syndrome (HES)), neuroblastoma, neurofibroma (e.g., neurofibromatosis (NF) type 1 or type 2, schwannomatosis), neuroendocrine cancer (e.g., gastroenteropancreatic neuroendoctrine tumor (GEP-NET), carcinoid tumor), osteosarcoma, ovarian cancer (e.g., cystadenocarcinoma, ovarian embryonal carcinoma, ovarian adenocarcinoma), papillary adenocarcinoma, pancreatic cancer (e.g., pancreatic andenocarcinoma, intraductal papillary mucinous neoplasm (IPMN), islet cell tumors), penile cancer (e.g., Paget's disease of the penis and scrotum), pinealoma, primitive neuroectodermal tumor (PNT), prostate cancer (e.g., prostate adenocarcinoma), rectal cancer, rhabdomyosarcoma, salivary gland cancer, skin cancer (e.g., squamous cell carcinoma (SCC), keratoacanthoma (KA), melanoma, basal cell carcinoma (BCC)), small bowel cancer (e.g., appendix cancer), soft tissue sarcoma (e.g., malignant fibrous histiocytoma (MFH), liposarcoma, malignant peripheral nerve sheath tumor (MPNST), chondrosarcoma, fibrosarcoma, myxosarcoma), sebaceous gland carcinoma, sweat gland carcinoma, synovioma, testicular cancer (e.g., seminoma, testicular embryonal carcinoma), thyroid cancer (e.g., papillary carcinoma of the thyroid, papillary thyroid carcinoma (PTC), medullary thyroid cancer), urethral cancer, vaginal cancer and vulvar cancer (e.g., Paget's disease of the vulva).

In certain embodiments, the cell described herein is in vivo. In certain embodiments, the cell is in vitro. In certain embodiments, the cell is ex vitro.

In certain embodiments, the methods of the invention include administering to a subject in need thereof an effective amount of Compound 3, particles, or pharmaceutical composition of the invention. In certain embodiments, the methods of the invention include contacting a cell with an effective amount of a compound, particles, or pharmaceutical composition of the invention.

In certain embodiments, the inventive methods are in vivo methods. In certain embodiments, the inventive methods are in vitro methods. In certain embodiments, the inventive methods are ex vitro methods.

In another aspect, the present invention provides the crystalline forms of Compound 3, particles, and pharmaceutical compositions of the invention for use in the treatment and/or prevention of a disease described herein in a subject in need thereof.

In yet another aspect, the present invention provides the crystalline forms of Compound 3, particles, and pharmaceutical compositions of the invention for use in the inhibition of abnormal angiogenesis in a subject in need thereof.

In still another aspect, the present invention provides the crystalline forms of Compound 3, particles, and pharmaceutical compositions of the invention for use in the inhibition of aberrant signaling of a growth factor in a subject or cell in need thereof.

EXAMPLES

In order that the invention described herein may be more fully understood, the following examples are set forth. It should be understood that these examples are for illustrative purposes only and are not to be construed as limiting this invention in any manner.

Example 1

Synthesis of Compound 3, Method A

Compound 1: 4-(4-fluoro-2-methyl-1H-indol-5-yloxy)-7-(benzyloxy)-6-methoxyquinazoline

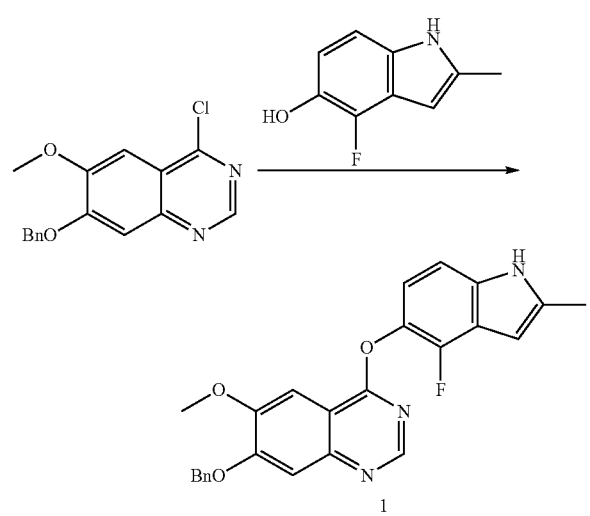

4-Fluoro-2-methyl-1H-indol-5-ol (0.53 g, 3.2 mmol) was dissolved in N,N-dimethylformamide (25 mL). The suspension was purged with nitrogen and potassium carbonate (0.92 g, 6.7 mmol) was added. 7-(Benzyloxy)-4-chloro-6-methoxyquinazoline (1.0 g, 3.3 mmol) was added and the suspension was purged with nitrogen again. The suspension was heated overnight at 85° C. in an oil bath. The solvent was evaporated. The residue was treated with water (100 mL) and sonicated. The solid was filtered off, washed with water and hexanes, and dried in high vacuum overnight leaving Compound 1 as a gray solid (1.4 g, 100%). m/z: 430 (M+H, 100%) (positive ionization mode).

Compound 2: 4-(4-fluoro-2-methyl-1H-indol-5-yloxy)-6-methoxyquinazolin-7-ol

Scheme 1B

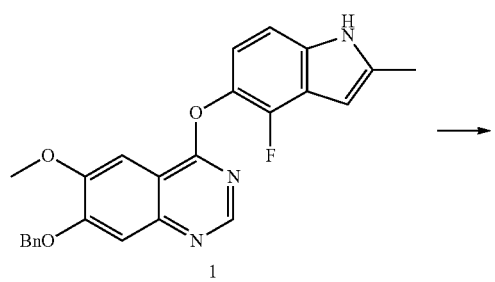

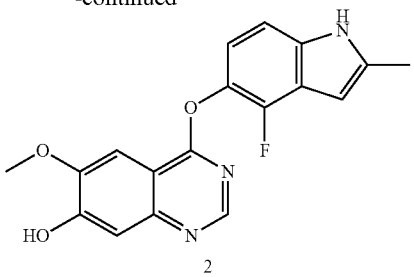

4-(4-Fluoro-2-methyl-1H-indol-5-yloxy)-7-(benzyloxy)-6-methoxyquinazoline (Compound 1, 0.46 g, 1.1 mmol) was dissolved in N,N-dimethylformamide (10 mL). Palladium hydroxide catalyst (250 mg, 10% on carbon) was added, followed by ammonium formate (0.67 g, 10.6 mmol). The reaction solution was stirred for 2 hours at room temperature. The catalyst was filtered through a CELITE pad, then the solution was evaporated, then dried in high vacuum overnight to generate Compound 2 as a brown solid (0.36 g, 100%) m/z: 340 (M+H, 100%) (positive ionization mode).

Compound 3: 7-(3-(4-(4-fluoro-2-methyl-1H-indol-5-yloxy)-6-methoxyquinazolin-7-yloxy)propyl)-2-oxa-7-azaspiro[3.5]nonane Scheme 1C

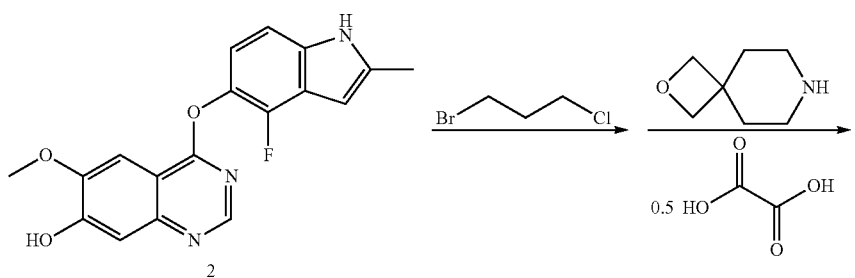

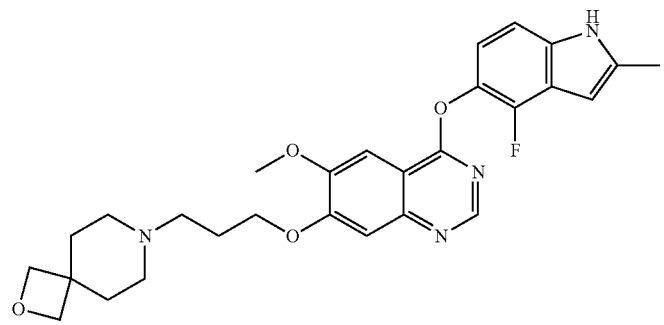

4-(4-Fluoro-2-methyl-1H-indol-5-yloxy)-6-methoxyquinazolin-7-ol (Compound 2, 0.36 g, 1.1 mmol) was dissolved in N,N-dimethylformamide (10 mL). Potassium carbonate (0.90 g, 6.5 mmol) was added followed by 1-bromo-3-chloropropane (0.34 g, 2.2 mmol). The suspension was heated at 45° C. for 2 hours. The solvent was evaporated and the residue was suspended in dichloromethane (20 mL). The suspension was applied on a pad of silica gel. The impurities were eluted with dichloromethane and the compound was eluted with ethyl acetate (Rf=0.7 in ethyl acetate). The solvent was evaporated and the residue was dried in high vacuum leaving a yellow foam (0.35 g, 80%) m/z: 416 (M+H, 100%) (positive ionization mode), which was dissolved in N,N-dimethylformamide (5 mL). Potassium bromide (0.12 g, 1.0 mmol) was added followed by potassium carbonate (0.90 g, 7.8 mmol) and 2-oxa-7-azaspiro[3.5]nonane oxalate (0.35 g, 1.9 mmol). The suspension was heated at 85° C. for 4 hours. The solvent was evaporated and the residue was suspended in aqueous sodium bicarbonate (50 mL) and sonicated. The precipitate was filtered off. Drying in high vacuum gave a brown solid (0.34 g). Purification by reverse phase HPLC provided Compound 3 as an off-white solid (20 mg). m/z: 507 (M+H, 100%) (positive ionization mode). 1H NMR: (Chloroform-d): 8.60 (s, 1H), 8.10 (s, 1H), 7.65 (s, 1H); 7.35 (s, 1H), 7.10 (d, J=9.0 Hz 1H), 7.00 (dd, J=8.0; J=9.0 Hz, 1H), 6.35 (s, 1H), 4.45 (s, 4H), 4.35 (t, J=7.0 Hz, 2H), 4.15 (s, 3H), 2.55 (t, J=7.0 Hz, 2H), 2.46 (s, 3H), 2.40-2.35 (m, 4H), 2.15-2.10 (m, 2H), 1.90-1.85 (m, 4H).

Example 2

Synthesis of Compound 3, Method B

Scheme 2A

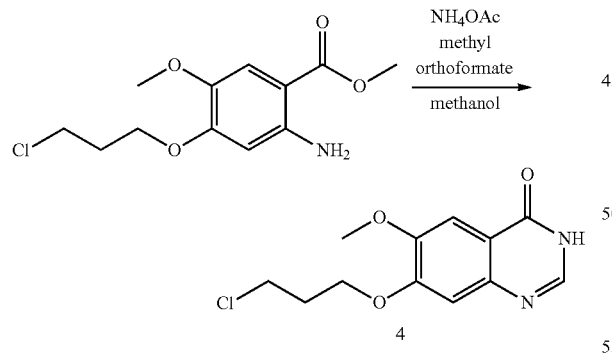

To a solution of 2-amino-4-(3-chloropropoxy)-5-methoxybenzoic acid methyl ester (48 g, 175 mmol) in methanol (150 mL) was added methyl orthoformate (46.4 g, 438 mmol), ammonium acetate (33.7 g, 438 mmol). The reaction mixture was stirred at reflux for 5 hours. Water (200 mL) was added to the reaction mixture to precipitate product, which was collected by filtration, washed with water (200 mL) and methanol (50 mL), then dried under reduced pressure to give 44 g (93.4%) of Compound 4 as a white solid.

Scheme 2B

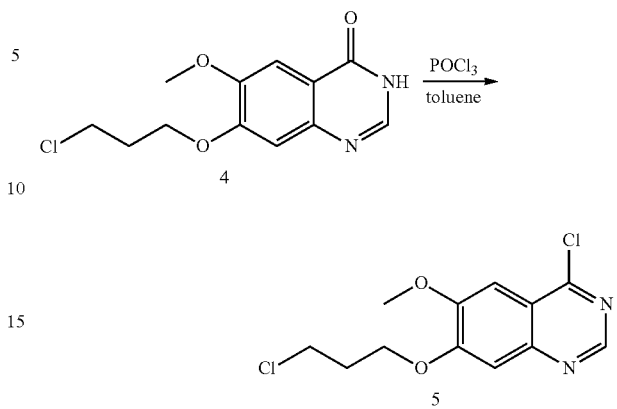

A mixture of Compound 4 (75 g, 279 mmol) and POCl$_3$ (100 mL) in toluene (500 mL) was stirred at reflux until the solution became clear. The solution was concentrated under reduced pressure and the residue was poured into ice water. After filtration, the solid was washed with water (500 mL×2) and dried to give 65 g (81.2%) of Compound 5 as a yellow solid.

Scheme 2C

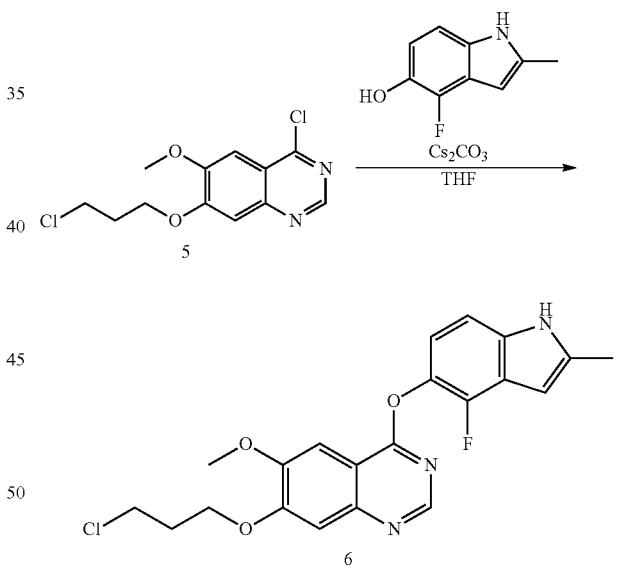

The mixture of Compound 5 (11 g, 38.33 mmol) and 4-fluoro-5-hydroxy-2-methylindole (9.49 g 57.50 mmol), Cs$_2$CO$_3$ (25 g, 76.66 mmol) in tetrahydrofuran (200 mL) was stirred at 50° C. overnight. The reaction mixture was extracted with ethyl acetate (200 mL×2) and the organic layers were combined and washed with water (200 mL) and brine (200 mL) successively. The organic layer was dried with sodium sulfate, then concentrated to dryness. The residue was purified by flash chromatography (petroleum ether:ethyl acetate=10:1 to 2:1) to give 13 g (81.5%) of Compound 6 as a brown solid.

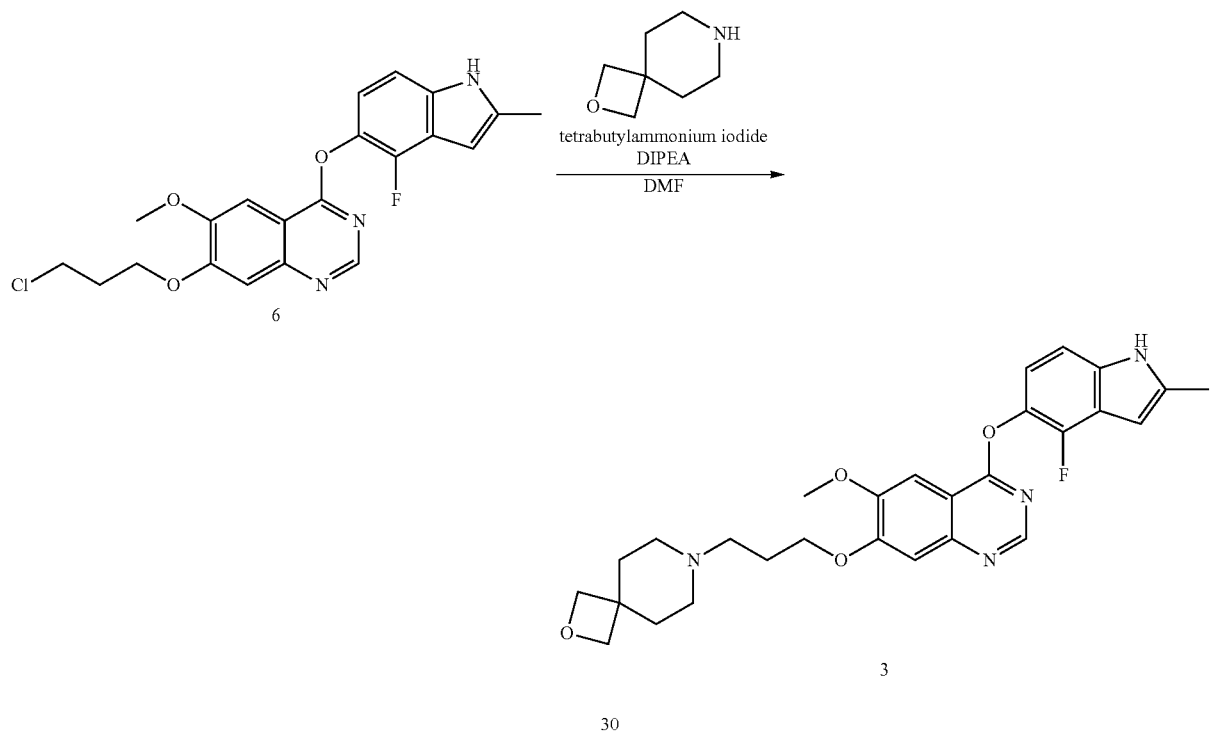

Scheme 2D

To the solution of Compound 6 (11 g, 26.44 mmol) in N,N-dimethylformamide (100 mL) was added 2-oxa-7-azaspiro[3.5]nonane (8.73 g, 68.75 mmol), tetrabutylammonium iodide (9.76 g, 26.44 mmol) and diisopropylethylamine (10.23 g, 79.33 mmol). The solution was heated to 60° C. overnight, then diluted with ethyl acetate (200 mL). The mixture was washed with brine (100 mL×5), dried over sodium sulfate, then solvent was evaporated under reduced pressure to give the crude product as a black solid. The crude product was purified by flash chromatography (dichloromethane:methanol=50:1 to 10:1) to give 6.5 g (48.5%) of Compound 3 as a light yellow solid. Analysis by XRPD showed that the isolated compound was amorphous.

Example 3

Compound 3 Formulated as Mucus Penetrating Particles (MPP)

Compound 3 was formulated as mucus penetrating particles (MPP). Specifically, Compound 3 from Example 2 was milled in the presence of PLURONIC F127 (F127) to determine whether F127 1) aids particle size reduction to several hundreds of nanometers and 2) physically (non-covalently) coats the surface of generated nanoparticles with a mucoinert coating that would minimize particle interactions with mucus constituents and prevent mucus adhesion.

A milling procedure was employed in which an aqueous dispersion containing coarse drug particles and PLURONIC F127 (F127) was milled with grinding medium until particle size was reduced to approximately 270 nm (z-averaged) as measured by dynamic light scattering. These particles were found to have a polydispersity index (a measure of the width of the particle size distribution) of 0.142. In this example suspensions were buffered using DPBS (Dulbecco's Phosphate-Buffered Saline) which yields a suspension that is both isotonic and has a physiologically relevant pH.

In order to determine whether the generated particles have reduced interactions with mucins and are therefore able to move within mucus without becoming trapped, particles were incubated with human cervicovaginal mucus (CVM) and observed via dark field microscopy. 1 μL or less of the nanoparticle suspension was added to 20 μL of CVM. Observations were made in a minimum of three distinct and randomly selected areas of the CVM sample. Control particles with known behavior were used to qualify the CVM sample as appropriate for the assay. Mobility in mucus was observed and therefore the nanoparticles were deemed to be effective MPP.

Example 4

Crystalline Forms of Compound 3

The crystalline forms of Compound 3 were prepared, and then analyzed by XRPD, Differential Scanning Calorimetry (DSC) analysis and Thermogravimetric Analysis (TGA).

For XRPD, patterns were obtained using a Rigaku MiniFlex 600 benchtop x-ray diffractometer equipped with a Cu X-ray tube (Cu/Kα=1.54059 Å), a six-position sample changer and a D/teX Ultra detector.

Sample Preparation, Procedure A

As described below for the preparation of Crystalline Form A by milling, particles were isolated from bulk formulation by centrifugation at 55,000 rpm over 15 minutes and deposited thinly and evenly onto a flat zero background XRPD sample holder (Rigaku 906165 Flush, Si510). The sample was allowed to dry under gentle air stream, usually for up to 3 minutes, until it was visually dry.

Sample Preparation, Procedure B

As described below for the preparation of neat Crystalline Form B by crystallization, milligram amounts of solid sample were firmly packed in the 5-mm×0.2-mm depression of a zero background sample holder (Rigaku 906166 5 mm×0.2 mm Well, Si510).

XRPD patterns were acquired from 3-40° two theta at 0.02° step size and 5°/min scan speed using the following instrument settings: 40 kV-15 mA X-ray generator, 2.5° Soller Slit, 10 mm HIS, 0.625° Divergence Slit, 8 mm Scatter Slit with Kβ filter, and an open Receiving Slit. Diffraction patterns were viewed and analyzed using PDXL analysis software provided by the instrument manufacturer. Using the sample preparation procedures described above, a reference standard silicon powder (NIST Standard Reference Material 640d) generated a peak at 28.44° and 28.38° two theta using Procedure A and Procedure B, respectively.

For DSC, about 2 mg of sample was weighed into a standard aluminum sample pan. The sample pan was loaded into the apparatus (Q1000 Differential Scanning Calorimeter, TA Instruments), which was equipped with an autosampler. A thermogram was obtained by individually heating the sample at a rate of 10° C./min from room temperature to approximately 250-300° C. using an empty standard aluminum pan as a reference. Dry nitrogen was used as a sample purge gas and was set to flow at 50 mL/min. Thermal transitions were viewed and analyzed using the analysis software provided with the instrument.

For TGA, about 6 mg of the sample was transferred into an aluminum sample pan. The pan was placed in the loading platform and was then automatically loaded into the apparatus (Q500 Thermogravimetric Analyzer, TA Instruments) using the control software. Thermograms were obtained by individually heating the sample at 10° C./min from room temperature to 300° C. under flowing dry nitrogen, with a sample purge flow rate of 25 mL/min and a balance purge flow rate of 10 mL/min. Thermal transitions (e.g., weight changes) were viewed and analyzed using the analysis software provided with the instrument.

Preparation of Mucus-Penetrating Particles Comprising of Crystalline Form A

In accordance to Example 3, mucus-penetrating particles comprising of Crystalline Form A was prepared by wet milling amorphous Compound 3 produced in Example 2. A slurry containing 5% amorphous Compound 3 and 5% F127 in PBS (0.0067 M $PO_4^{3-}$), pH 7.1 was added to an equal bulk volume of 1-mm ceria-stabilized zirconium oxide beads in a glass vial (e.g., 2 mL of slurry per 2 mL of beads). A magnetic stir bar was used to agitate the beads, stirring at approximately 500 rpm. The sample was milled for 2 days. Nanoparticles which were approximately 200 nm (z-averaged) in diameter, as measured by dynamic light scattering (DLS), were generated. During the milling process, Compound 3 converted from amorphous to crystalline Form A as confirmed by XRPD.

An XRPD analysis of the resulting crystalline Form A of Compound 3 was performed. The XRPD pattern of crystalline Form A is illustrated in FIG. 1 and the reflections comprised in its XRPD pattern are listed in Table 1.

TABLE 1

XRPD Peak Listing for Crystalline Form A of Compound 3

| No. | Position ± 0.3 [°2θ] | d-spacing ± 0.3 [Å] | Relative Intensity [%] |
|---|---|---|---|
| 1 | 6.11 | 14.45 | 60.14 |
| 2 | 9.63 | 9.17 | 52.72 |
| 3 | 11.10 | 7.96 | 11.17 |
| 4 | 11.46 | 7.71 | 22.60 |
| 5 | 12.26 | 7.22 | 10.66 |
| 6 | 15.66 | 5.65 | 3.25 |
| 7 | 16.41 | 5.40 | 30.14 |

TABLE 1-continued

XRPD Peak Listing for Crystalline Form A of Compound 3

| No. | Position ± 0.3 [°2θ] | d-spacing ± 0.3 [Å] | Relative Intensity [%] |
|---|---|---|---|
| 8 | 17.54 | 5.05 | 7.29 |
| 9 | 18.16 | 4.88 | 44.67 |
| 10 | 18.60 | 4.77 | 100 |
| 11 | 19.51 | 4.55 | 32.84 |
| 12 | 20.36 | 4.36 | 52.26 |
| 13 | 21.12 | 4.20 | 12.65 |
| 14 | 22.31 | 3.98 | 7.49 |
| 15 | 23.01 | 3.86 | 24.04 |
| 16 | 24.79 | 3.59 | 7.64 |
| 17 | 25.71 | 3.46 | 30.32 |
| 18 | 28.90 | 3.09 | 8.29 |
| 19 | 30.81 | 2.90 | 1.99 |
| 20 | 31.64 | 2.83 | 3.28 |

Preparation of Neat Crystalline Form B

Crystalline Form B of Compound 3 was prepared by thermal crystallization of the amorphous form of Compound 3 in a binary mixture of acetone and water. Specifically, Compound 3 (80 mg) from Example 2 was added to an 8-mL scintillation vial containing a 7×2 mm stir bar, followed by addition of a hot mixture of 4:1 acetone:water (4 mL total). The vial was heated on a hot plate while stirring to completely dissolve Compound 3. Upon spontaneous cooling to ambient temperature, Form B crystallized slowly from solution. After allowing crystallization to continue overnight, solvent was discarded and the solid crystals that remained in the vial were collected and allowed to dry overnight under vacuum. As discussed below, XRPD analysis generated unique reflections, indicating the formation of a new crystalline form.

Figure 2:
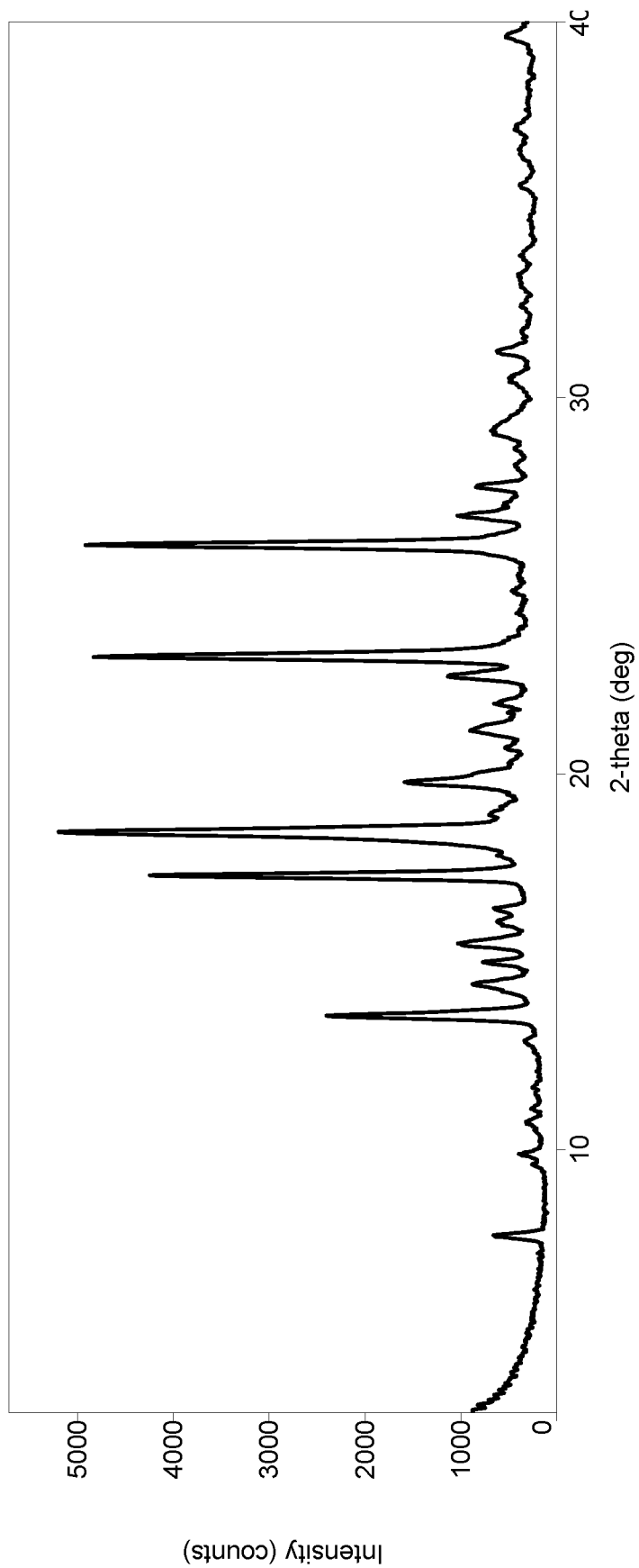
FIG. 2 provides a representative XRPD pattern for crystalline Form B of Compound 3.

An XRPD analysis of the resulting crystalline Form B of Compound 3 was performed. The XRPD pattern of crystalline Form B is illustrated in FIG. 2 and the reflections comprised in its XRPD pattern are listed in Table 2.

TABLE 2

XRPD Peak Listing for Crystalline Form B of Compound 3

| No. | Position ± 0.3 [°2θ] | d-spacing ± 0.3 [Å] | Relative Intensity [%] |
|---|---|---|---|
| 1 | 7.7 | 11.47 | 7 |
| 2 | 9.87 | 8.96 | 5 |
| 3 | 10.69 | 8.27 | 4 |
| 4 | 12.88 | 6.87 | 1 |
| 5 | 13.53 | 6.54 | 30 |
| 6 | 14.4 | 6.14 | 12 |
| 7 | 14.97 | 5.91 | 5 |
| 8 | 15.45 | 5.73 | 12 |
| 9 | 16.42 | 5.39 | 3 |
| 10 | 17.27 | 5.13 | 42 |
| 11 | 18.44 | 4.81 | 100 |
| 12 | 18.9 | 4.69 | 3 |
| 13 | 19.73 | 4.5 | 20 |
| 14 | 21.14 | 4.2 | 8 |
| 15 | 21.86 | 4.06 | 2 |
| 16 | 22.56 | 3.94 | 14 |
| 17 | 23.1 | 3.85 | 67 |
| 18 | 26.07 | 3.41 | 72 |
| 19 | 26.84 | 3.32 | 8 |
| 20 | 29.12 | 3.06 | 9 |

Figure 3:
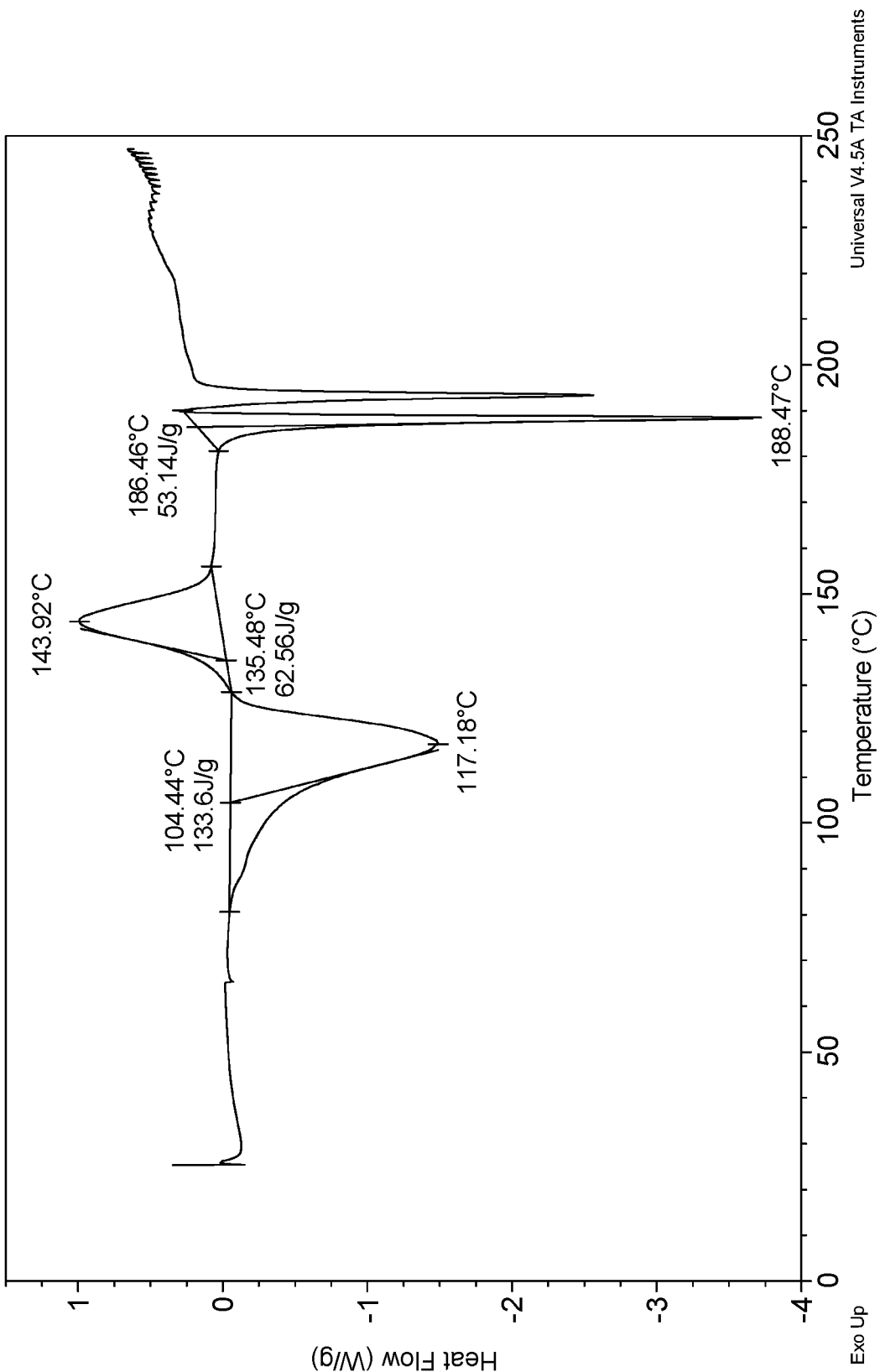
FIG. 3 provides a representative Differential Scanning Calorimetry (DSC) thermogram for crystalline Form B of Compound 3.
Figure 4:
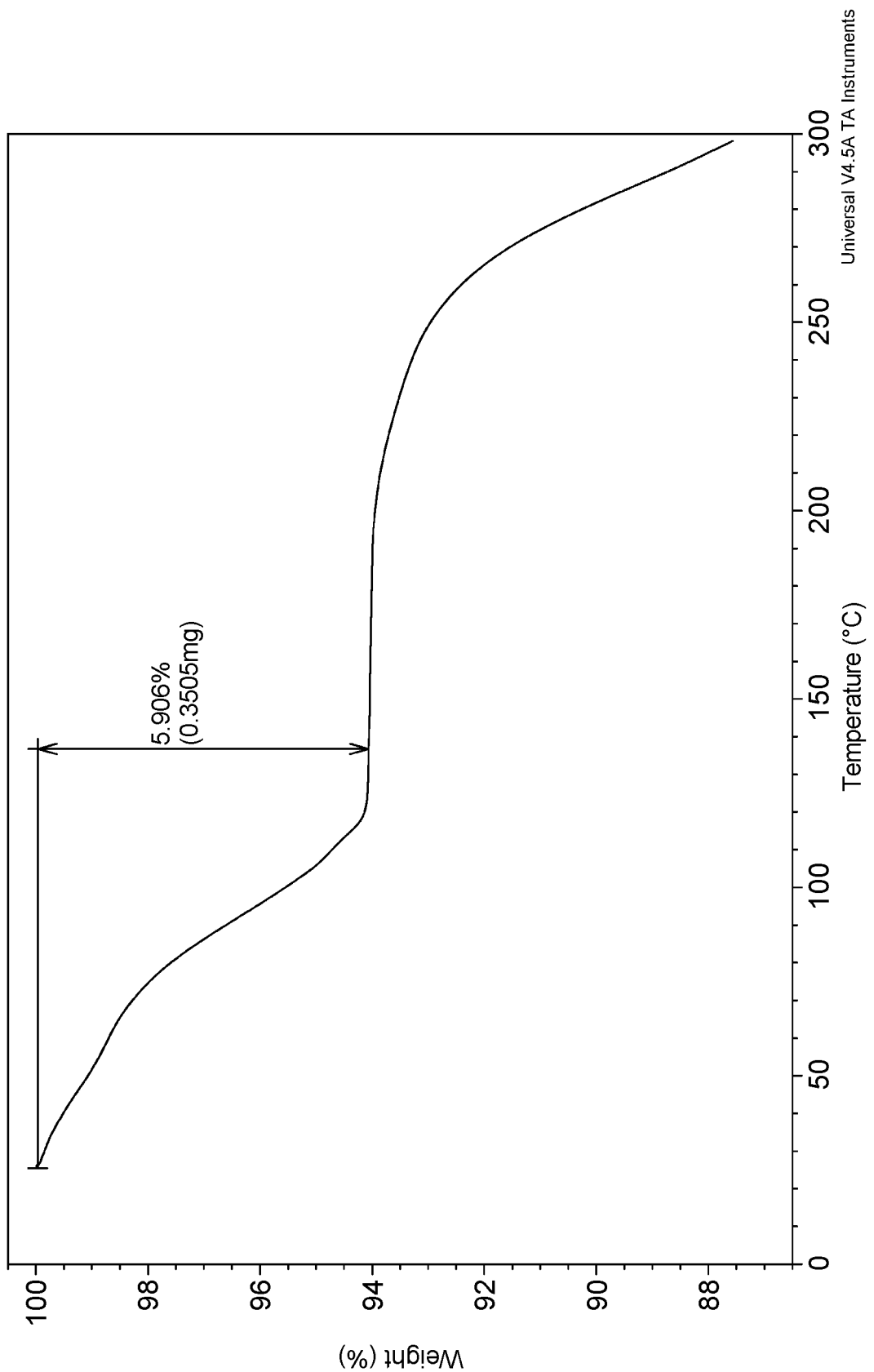
FIG. 4 provides a representative Thermogravimetric Analysis (TGA) thermogram for crystalline Form B of Compound 3.

DSC and TGA were also conducted on crystalline Form B of Compound 3. FIG. 3 shows that the DSC thermogram measured from 25° C. to 250° C., ramped at 10° C./min, was found to exhibit a broad dehydration endothermic event at 117° C. followed by crystallization then the melting of the presumed anhydrous form at 188° C. FIG. 4 shows that the TGA thermogram measured from 25° C. to 300° C., ramped at 10° C./min, was found to exhibit a mass loss of 6% from 25° C. up to 120° C. Presumably, the mass loss corresponds to two water molecules (theoretical weight loss of dihydrate=6.6%), thus making crystalline form B a dihydrate.

Preparation of Mucus-Penetrating Particles Comprising of Crystalline Form B

In accordance to Example 3, mucus-penetrating particles comprising of Crystalline Form B was prepared by wet-milling neat Crystalline Form B. A slurry containing 5% neat crystalline From B of Compound 3 and 5% F127 in DPBS (Dulbecco's Phosphate Buffered Saline) was added to an equal bulk volume of 1-mm ceria-stabilized zirconium oxide beads in a glass vial (e.g. 0.5 mL of slurry for 0.5 mL of beads). A magnetic stir bar was used to agitate the beads, stirring at approximately 500 rpm. The sample was milled for 2 days. Nanoparticles which were approximately 200 nm in diameter (z-averaged), as measured by DLS, were generated. After milling, XRPD analysis (not shown) confirmed that the crystal form was unchanged, which indicates that crystalline Form B remained stable during milling.

Stability of MPP Formulations Containing Crystalline Forms A and/or B

To characterize the stability of the resulting crystalline forms of Compound 3, changes in XRPD profiles following long-term storage were determined. An MPP suspension comprising of crystalline Form A was stored at room temperature for 7 weeks, while a second MPP suspension also comprising of crystalline Form A was stored at room temperature for 7 weeks followed by an additional 1.5 weeks of agitation. Following these periods, XRPD analyses revealed that the compounds still possessed the XRPD profile of crystalline Form A, indicating that the material is shelf stable in solution for at least 7 weeks. To further test the potential for longer term storage, two additional MPP samples comprising of Form A, which were formulated at pH 5.8 and pH 7.4 by incorporating different buffers in the milling slurry, were stored at room temperature for 8 months and then analyzed by XRPD. Again, the XRPD analysis (not shown) revealed that the crystals still possessed the XRPD profile of crystalline Form A, indicating that the materials are shelf stable as suspensions for at least 8 months.

Figure 5:
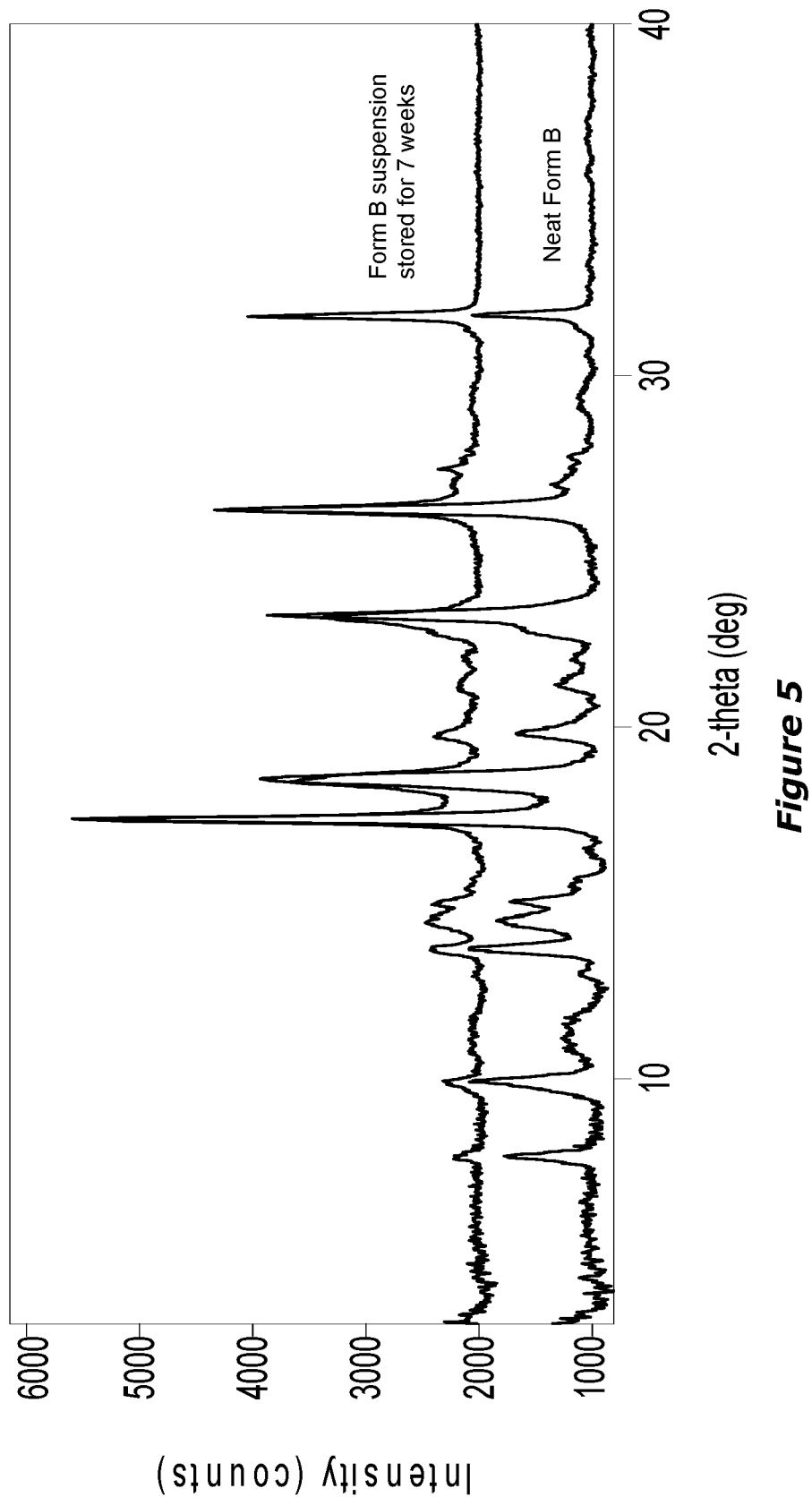
FIG. 5 provides an XRPD pattern for crystalline Form B of Compound 3 after its formation (bottom trace) and after being held in suspension for 7 weeks (top trace).

To confirm long-term stability, an MPP suspension of crystalline Form B was stored for 7 weeks at room temperature and then was characterized by XRPD. The results of that analysis are shown in FIG. 5, which provides the XRPD pattern of the original crystalline Form B material in the bottom trace and the XRPD pattern of the material after seven weeks of storage in the top trace. The material remained as crystalline Form B, which demonstrates that crystalline Form B is physically stable during storage.

Seeding Crystalline Form B During Milling of Amorphous Compound 3

Figure 6:
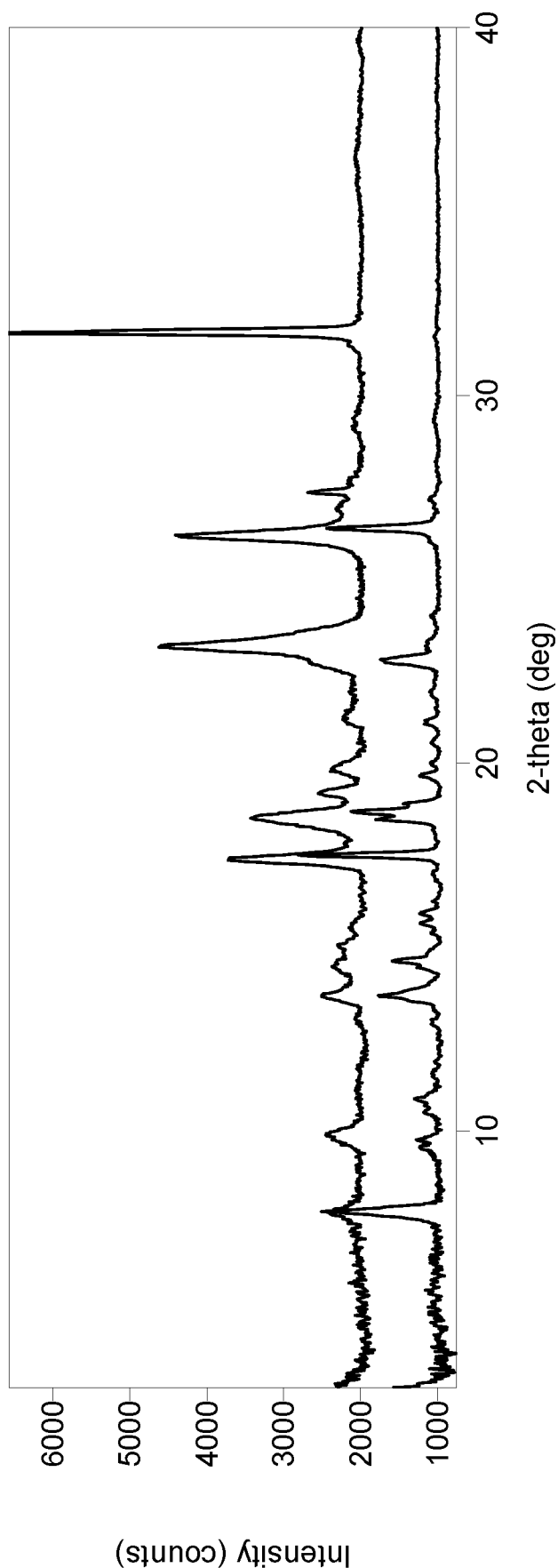
FIG. 6 provides an XRPD pattern for crystalline Form B of Compound 3 (bottom trace) and an XRPD pattern of a milling mixture of amorphous Compound 3 and crystalline Form B of Compound 3 (top trace).

In the absence of crystalline material, the amorphous material from Example 2 becomes crystalline Form A during milling, as described above. As such, the inventors wished to determine whether the presence of crystalline Form B during milling would seed the formation of crystalline Form B from amorphous Compound 3 during milling. A mixture of crystalline Form B and amorphous material was milled as follows: milling media, specifically 1-mm ceria-stabilized zirconium oxide beads, was added to a glass scintillation vial. Separately, a milling slurry was generated containing 2.5% crystalline Form B of Compound 3, 2.5% amorphous Compound 3, and 5% F127 in DPBS (Dulbecco's Phosphate Buffered Saline). The milling slurry was then added to the glass vial at an equal bulk volume to the beads (e.g. 0.5 mL of slurry for 0.5 mL of beads). A magnetic stir bar was used to agitate the beads, stirring at approximately 500 rpm. The sample was milled for 3 days. Nanoparticles which were approximately 150 nm (z-averaged) in diameter, as measured by DLS, were generated. After milling, XRPD analysis was performed, the results of which are shown in FIG. 6, which provides the XRPD pattern of crystalline Form B of Compound 3 in the bottom trace and the XRPD pattern of the milling mixture of amorphous and crystalline Form B of Compound 3 in the top trace. This analysis confirmed that, when some crystalline Form B was present during the milling process, the amorphous material converted to crystalline Form B as opposed to crystalline Form A during milling.

Figure 7:
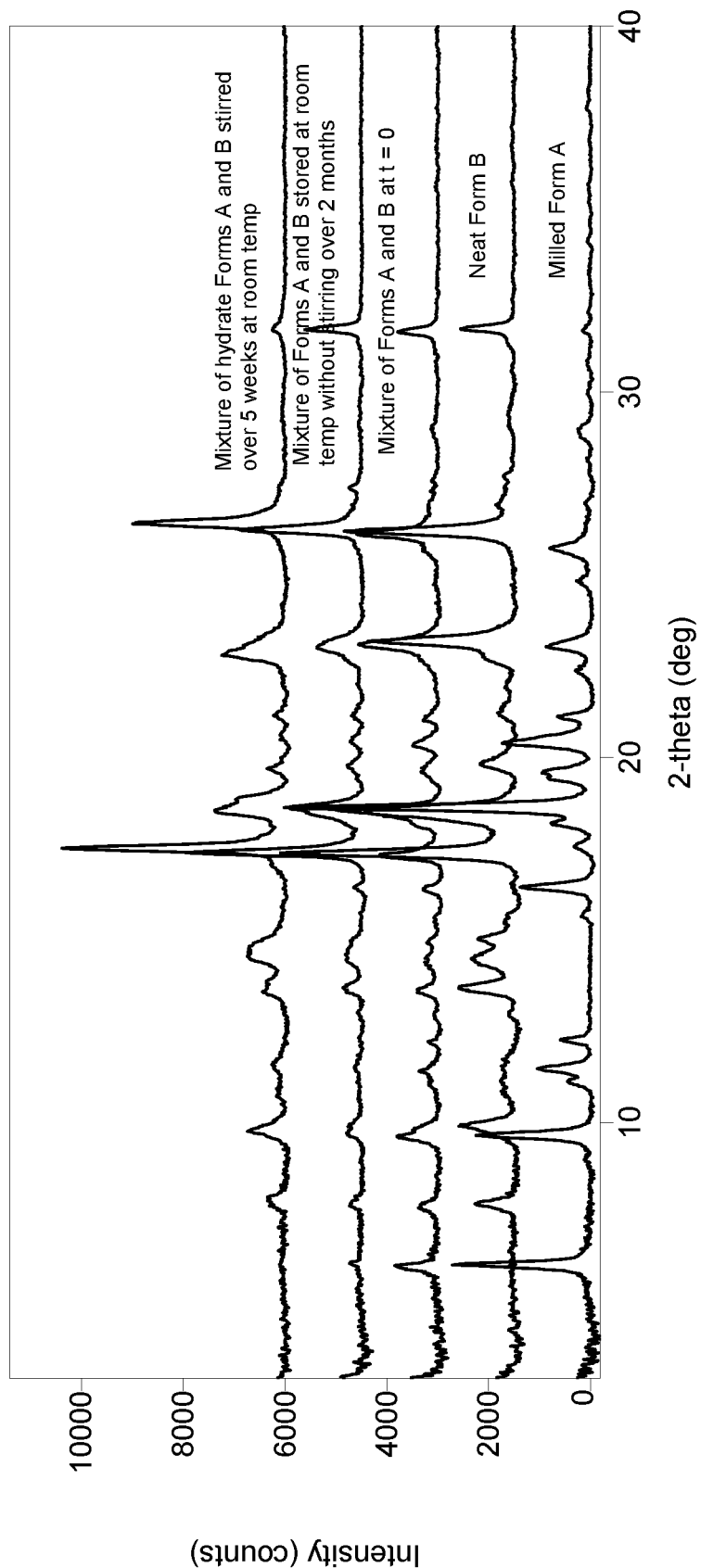
FIG. 7 provides XRPD patterns, from bottom to top, for: crystalline Form A of Compound 3, crystalline Form B of Compound 3, a mixture of crystalline Forms A and B that were milled separately and then combined (t=0), a mixture of crystalline Forms A and B that were milled separately and then combined and stored at room temperature for >2 months, and a mixture of crystalline Forms A and B that were milled separately and then combined and stirred at room temperature for 5 weeks.

Competition Between Crystalline Forms A and B to Determine the More Stable or Preferred MPP Form In order to assign one form as more stable, or more preferred, under the current formulation conditions, a competition experiment was performed. A suspension of nanoparticles of crystalline Form A was generated as described via wet milling the amorphous material. A suspension of nanoparticles of Form B was generated via wet milling of neat Form B crystals as described. The two suspensions were mixed in 1:1 ratio and incubated at room temperature. After 11 days, an XRPD analysis was performed, which estimated that the ratio of Forms A and B was unchanged in the mixture (not shown). A fraction of the mixture was then stirred using a magnetic stir bar to provide an increased energy input in order to accelerate the outcome of the competition experiment. After 5 weeks of stirring, the Compound 3 in the stirred formulation converted to crystalline Form B whereas the crystals in the unstirred formulation remained a mixture, as shown in FIG. 7. This result indicates that crystalline Form B is more stable under the current formulation conditions.

Example 5

Back of the Eye Drug Exposure from Topical Instillation of an MPP Comprising Crystalline Form A of Compound 3

A pharmacokinetic (PK) study of the crystalline Form A of Compound 3 formulated as MPP in accordance with Example 4 was performed in order to demonstrate that topical instillation of MPP formulations of these compounds results in drug exposure at the back of the eye. The study design is shown in Table 3.

TABLE 3

Study design for PK evaluation of Compound 3, Form A MPP

| Group | Test Article | Number of Animals (n/time point) | Dose Volume | Frequency/ Duration | Terminal Time Points (hours) |
|---|---|---|---|---|---|
| 1 | 3, Form A MPP, 2.0% | 3 | 35 µL | BID/5 days | 0.5 |
| 2 | 3, Form A MPP, 2.0% | 3 | 35 µL | BID/5 days | 1 |
| 3 | 3, Form A MPP, 2.0% | 3 | 35 µL | BID/5 days | 2 |
| 4 | 3, Form A MPP, 2.0% | 3 | 35 µL | BID/5 days | 4 |

BID = twice a day

Female Gottingen mini-pigs were used in these studies. Animals received a single topical ocular dose in the right eye twice daily, approximately 12 hours apart (±1 hour), for 4 consecutive days; on the fifth day animals received a single topical ocular dose in the a.m. only for a total of 9 doses over the study duration.

All animals were euthanized with sodium pentobarbital and blood collected via cardiac puncture into tubes containing $K_2EDTA$ and centrifuged to obtain plasma. Then, both eyes were enucleated, flash frozen and stored at −70° C. for at least 2 hours. Within approximately 2 days, the frozen matrices were collected as right and left eye for choroid and retina.

Figure 8:
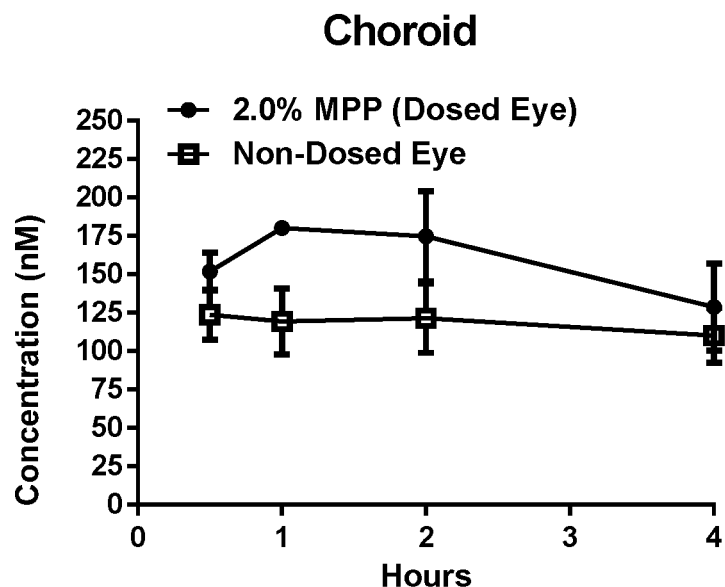
FIG. 8 is a PK profile for Compound 3 in choroid tissue of Gottingen mini-pig after topical administration.
Figure 9:
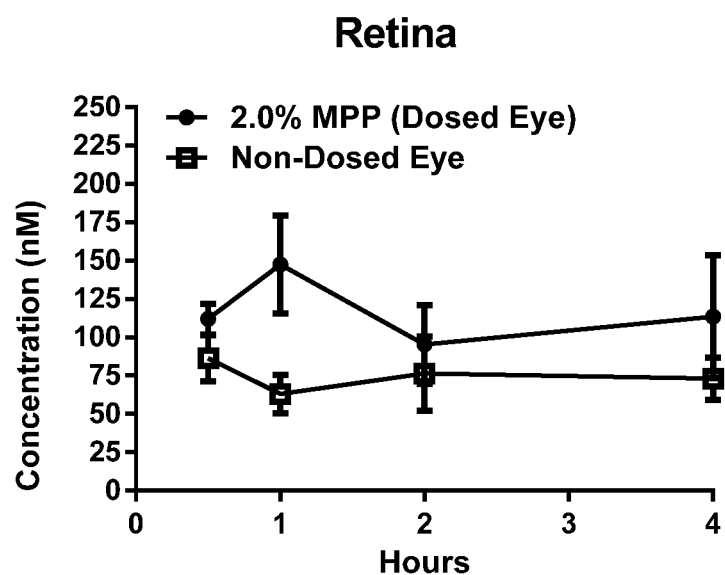
FIG. 9 is a PK profile for Compound 3 in retina tissue of Gottingen mini-pig after topical administration.
Figure 10:
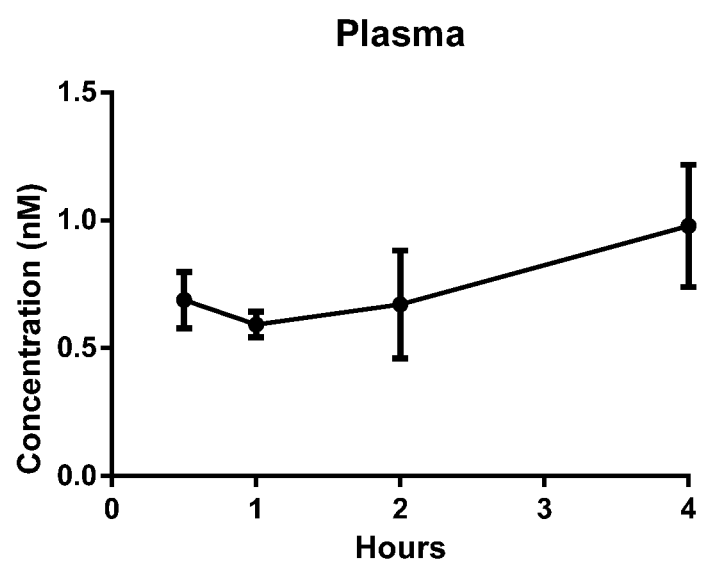
FIG. 10 is a PK profile for Compound 3 in plasma of Gottingen mini-pig after topical administration.

The resulting drug exposures in plasma and in the back of the eye are shown in FIGS. 8-10. These results demonstrate that topical instillation of crystalline Form A of Compound 3 as MPP results in drug exposure in the retina and choroid in vivo.

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A method of inhibiting aberrant vascular endothelial growth factor (VEGF) signaling comprising administering to a subject in need thereof a therapeutically effective amount of crystalline form A of 7-(3-(4-(4-fluoro-2-methyl-1H-indol-5-yloxy)-6-methoxyquinazolin-7-yloxy)propyl)-2-oxa-7-azaspiro[3.5]nonane having an X-ray powder diffraction (XRPD) pattern with peaks at about 6.11±0.3, 9.63±0.3, 9.87±0.3, 11.10±0.3, 11.46±0.3, 12.26±0.3, 12.88±0.3, 14.40±0.3, 15.45±0.3, 15.66±0.3, 16.41±0.3, 17.54±0.3, 18.16±0.3, 18.60±0.3, 19.51±0.3, 20.36±0.3, 21.12±0.3, 21.14±0.3, 22.31±0.3, 23.01±0.3, 24.79±0.3, 25.71±0.3, 26.84±0.3, and 28.90±0.3 degrees two theta.

2. The method of claim 1, wherein the crystalline form is administered topically, by injection, to the eye, orally, or by inhalation.

3. The method of claim 1, wherein the inhibition of aberrant VEGF signaling treats an ocular disease.

4. The method of claim 3, wherein the ocular disease is retinopathy, age-related macular degeneration, corneal neovascularization, diabetic macular edema, or retinal vein occlusion.

5. The method of claim 1, wherein the aberrant signaling of VEGF is associated with cancer.

6. A method of inhibiting aberrant vascular endothelial growth factor (VEGF) signaling comprising administering to a subject in need thereof a therapeutically effective amount of crystalline form A of 7-(3-(4-(4-fluoro-2-methyl-1H-indol-5-yloxy)-6-methoxyquinazolin-7-yloxy)propyl)-2-oxa-7-azaspiro[3.5]nonane having an X-ray powder diffraction (XRPD) pattern with peaks at about 7.70±0.3, 13.53±0.3, 9.87±0.3, 10.69±0.3, 12.88±0.3, 14.40±0.3, 15.45±0.3, 16.42±0.3, 17.27±0.3, 18.44±0.3, 18.90±0.3, 19.73±0.3, 21.14±0.3, 22.56±0.3, 23.10±0.3, 26.07±0.3, 26.84±0.3, and 29.12±0.3 degrees two theta.

7. The method of claim 6, wherein the crystalline form is administered topically, by injection, to the eye, orally, or by inhalation.

8. The method of claim 6, wherein the inhibition of aberrant VEGF signaling treats an ocular disease.

9. The method of claim 3, wherein the ocular disease is retinopathy, age-related macular degeneration, corneal neovascularization, diabetic macular edema, or retinal vein occlusion.

10. The method of claim 6, wherein the aberrant signaling of VEGF is associated with cancer.

* * * * *